(12) United States Patent
Madsen et al.

(10) Patent No.: US 6,706,744 B2
(45) Date of Patent: Mar. 16, 2004

(54) GLUCAGON ANTAGONISTS/INVERSE AGONISTS

(75) Inventors: Peter Madsen, Bagsvaerd (DK); Jesper Lau, Farum (DK); Anthony Ling, San Diego, CA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/996,023

(22) Filed: Nov. 16, 2001

(65) Prior Publication Data

US 2003/0065031 A1 Apr. 3, 2003

Related U.S. Application Data

(60) Provisional application No. 60/252,343, filed on Nov. 20, 2000.

(30) Foreign Application Priority Data

Nov. 17, 2000 (DK) .......................... 2000 01731

(51) Int. Cl.$^7$ ..................... A61K 31/428; C07D 277/82
(52) U.S. Cl. ............... 514/367; 514/562; 514/567; 514/364; 514/417; 514/445; 514/452; 514/366; 514/381; 514/375; 548/481; 548/131; 548/180; 548/163; 548/151; 548/224; 548/253; 549/63; 549/365; 549/366; 562/430; 562/439
(58) Field of Search ................. 562/430, 439; 548/481, 131, 180, 163, 151, 224, 253; 549/63, 365, 366; 514/562, 567, 364, 417, 445, 452, 367, 366, 381, 375

(56) References Cited

U.S. PATENT DOCUMENTS

| | | | |
|---|---|---|---|
| 4,359,474 A | 11/1982 | Anderson et al. | 424/273 |
| 4,374,130 A | 2/1983 | Barcza | 424/184 |
| 5,776,954 A | 7/1998 | de Laszlo et al. | 514/340 |
| 5,837,719 A | 11/1998 | de Laszlo et al. | 514/343 |
| 5,880,139 A | 3/1999 | Chang | 514/326 |
| 6,503,949 B1 * | 1/2003 | Lau et al. | 514/617 |

FOREIGN PATENT DOCUMENTS

| | | |
|---|---|---|
| WO | WO 94/14426 | 7/1994 |
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 98/24780 | 6/1998 |
| WO | WO 98/24782 | 6/1998 |
| WO | WO 99/01423 | 1/1999 |
| WO | WO 99/24404 | 5/1999 |
| WO | WO 99/32448 | 7/1999 |
| WO | WO 00/39088 | 7/2000 |
| WO | WO 00/69810 | 11/2000 |

OTHER PUBLICATIONS

C.L. Brand et al., "Immunoneutralization of endogenous glucagons with Monoclonal glucagons antibody normalizes hyperglycaemia in moderately Streptozotocin–diabetic rats–"Diabetologia, vol. 37 pp. 985–993 (1994).
C.L Brand et al [535] Diabetes 43, [suppl 1], 172A (1994).
C.L. Brand et al., Am J. Physiol. 269, E469–E477 (1995).
C.L Brand et al [492] Diabetes 44 [suppl 1], 134A (1995).
C.L. Brand et al., "Evidence for a Major Role for Glucagon in Regulation of Plasma Glucose in Conscious, Nondiabetic, and Alloxan Induced Diabetic Rabbits", Diabetes vol. 45, pp. 1076–1083 (1996).
L.J. Jelinek et al., "Expression Cloning and Signaling Properties of the Rat Glucagon Receptor" Science vol. 259, pp. 1614–1616 (1993).
J.L. Collins et al., "CP–99, 711: A Non–Peptide Glucagon Receptor Antagonist"Bioorganic & Med.Chem. Ltr. vol.2, No.9, pp. 915–918(1992).
P. Madsen et al., "Discovery and Structure–Activity Relationship of the First Non–Peptide Competitive Human Glucagon Receptor Antagonists" J. Med.Chem vol. 41, pp. 5150–5157 (1998).

* cited by examiner

*Primary Examiner*—Laura L. Stockton
(74) *Attorney, Agent, or Firm*—Reza Green, Esq.; Richard W. Boak, Esq.; Marc A. Began, Esq.

(57) ABSTRACT

Novel compounds, which act to antagonize the action of the glucagon hormone on the glucagon receptor. Owing to their antagonizing effect of the glucagon receptor the compounds may be suitable for the treatment and/or prevention of any diseases and disorders, wherein a glucagon antagonistic action is beneficial, such as hyperglycemia, Type 1 diabetes, Type 2 diabetes, disorders of the lipid metabolism and obesity.

6 Claims, No Drawings

GLUCAGON ANTAGONISTS/INVERSE AGONISTS

CROSS-REFERENCE TO RELATED APPLICATIONS

This application claims priority under 35 U.S.C. 119 of Danish application PA 2000 01731 filed Nov. 17, 2000, and of U.S. application 60/252,343 filed Nov. 20, 2000, the contents of both of which are fully incorporated herein by reference.

FIELD OF THE INVENTION

The present invention relates to agents that act to antagonize the action of the glucagon peptide hormone on the glucagon receptor. More particularly, it relates to glucagon antagonists or inverse agonists.

BACKGROUND OF THE INVENTION

Glucagon is a key hormonal agent that, in co-operation with insulin, mediates homeostatic regulation of the amount of glucose in the blood. Glucagon primarily acts by stimulating certain cells (mostly liver cells) to release glucose when blood glucose levels fall. The action of glucagon is opposite to that of insulin, which stimulates cells to take up and store glucose whenever blood glucose levels rise. Both glucagon and insulin are peptide hormones.

Glucagon is produced in the alpha islet cells of the pancreas and insulin in the beta islet cells. Diabetes mellitus is a common disorder of glucose metabolism. The disease is characterized by hyperglycemia and may be classified as Type 1 diabetes, the insulin-dependent form, or Type 2 diabetes, which is non-insulin-dependent in character. Subjects with Type 1 diabetes are hyperglycemic and hypoinsulinemic, and the conventional treatment for this form of the disease is to provide insulin. However, in some patients with Type 1 or Type 2 diabetes, absolute or relative elevated glucagon levels have been shown to contribute to the hyperglycemic state. Both in healthy control animals as well as in animal models of Type 1 and Type 2 diabetes, removal of circulating glucagon with selective and specific anti-bodies has resulted in reduction of the glycemic level (Brand et al., Diabetologia 37, 985 (1994); Diabetes 43, [suppl 1], 172A (1994); Am. J. Physiol. 269, E469–E477 (1995); Diabetes 44 [suppl 1], 134A (1995); Diabetes 45, 1076 (1996)). These studies suggest that glucagon suppression or an action that antagonizes glucagon could be a useful adjunct to conventional treatment of hyperglycemia in diabetic patients. The action of glucagon can be suppressed by providing an antagonist or an inverse agonist, i.e. substances that inhibit or prevent glucagon-induced responses. The antagonist can be peptidic or non-peptidic in nature.

Native glucagon is a 29 amino acid peptide having the sequence:

His-Ser-Glu-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH.

Glucagon exerts its action by binding to and activating its receptor, which is part of the Glucagon-Secretin branch of the 7-transmembrane G-protein coupled receptor family (Jelinek et al., Science 259, 1614, (1993)). The receptor functions by activating the adenylyl cyclase second messenger system and the result is an increase in cAMP levels.

Peptide antagonists of peptide hormones are often quite potent. However, they are generally known not to be orally available because of degradation by physiological enzymes, and poor distribution in vivo. Therefore, orally available non-peptide antagonists of peptide hormones are generally preferred. Among the non-peptide glucagon antagonists, a quinoxaline derivative, (2-styryl-3-[3-(dimethylamino) propylmethylamino]-6,7-dichloroquinoxaline was found to displace glucagon from the rat liver receptor (Collins, J. L. et al., Bioorganic and Medicinal Chemistry Letters 2(9) :915–918 (1992)). WO 94114426 (The Wellcome Foundation Limited) discloses use of skyrin, a natural product comprising a pair of linked 9,10-anthracenedione groups, and its synthetic analogues, as glucagon antagonists. U.S. Pat. No. 4,359,474 (Sandoz) discloses the glucagon inhibiting properties of 1-phenyl pyrazole derivatives. U.S. Pat. No. 4,374,130 (Sandoz) discloses substituted disilacyclohexanes as glucagon inhibiting agents. WO 98/04528 (Bayer Corporation) discloses substituted pyridines and biphenyls as glucagon antagonists. U.S. Pat. No. 5,776,954 (Merck & Co., Inc.) discloses substituted pyridyl pyrroles as glucagon antagonists and WO 98121957, WO 98/22108, WO 98122109 and U.S. Pat. No. 5,880,139 (Merck & Co., Inc.) disclose 2,4-diaryl-5-pyridylimidazoles as glucagon antagonists. Furthermore, WO 97/16442 and U.S. Pat. No. 5,837, 719 (Merck & Co., Inc.) disclose 2,5-substituted aryl pyrroles as glucagon antagonists. WO 98/24780, WO 98/24782, WO 99/24404 and WO 99/32448 (Amgen Inc.) disclose substituted pyrimidinone and pyridone compounds and substituted pyrimidine compounds, respectively, which are stated to possess glucagon antagonistic activity. Madsen et al. (J. Med. Chem. 1998 (41) 5151–7) discloses a series of 2-(benzimidazol-2-ylthio)-1-(3,4-dihydroxyphenyl)-1-ethanones as competitive human glucagon receptor antagonists. WO 99/01423 and WO 00/39088 (Novo Nordisk A/S) disclose different series of alkylidene hydrazides as glucagon antagonists/inverse agonists. These known glucagon antagonists differ structurally from the present compounds.

DESCRIPTION OF THE INVENTION

The present invention is based on the unexpected observation that compounds belonging to the series of the compounds disclosed below have a high binding affinity for the glucagon receptor and act to antagonize the action of glucagon.

The present invention relates to a compound selected from:

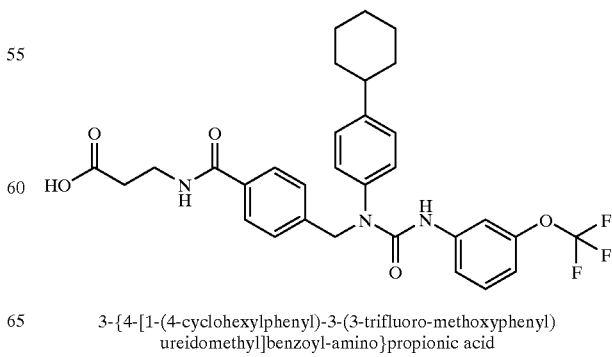

3-{4-[1-(4-cyclohexylphenyl)-3-(3-trifluoro-methoxyphenyl) ureidomethyl]benzoyl-amino}propionic acid -continued

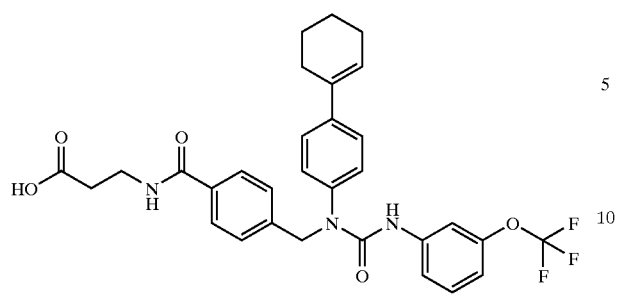

3-{4-[1-(4-cyclohex-1-enylphenyl)-3-(3-tri-fluoromethoxyphenyl)
ureidomethyl]-benzoylamino}propionic acid

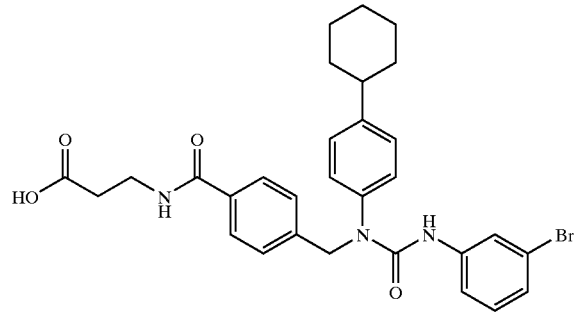

3-{4-[1-(4-cyclohexylphenyl)-3-(3-bromo-phenyl)
ureidomethyl]benzoylamino}propionic acid

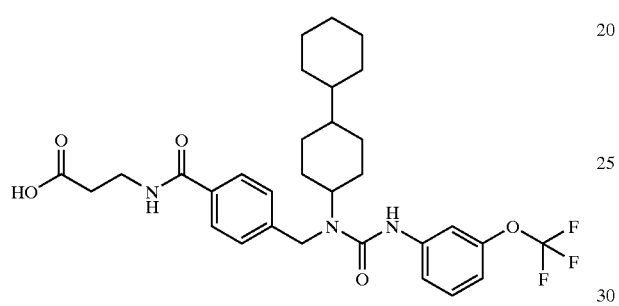

3-{4-[1-(4-cyclohexylcyclohexly)-3-(3-tri-fluoromethoxyphenyl)
ureidomethyl]-benzoylamino}propionic acid

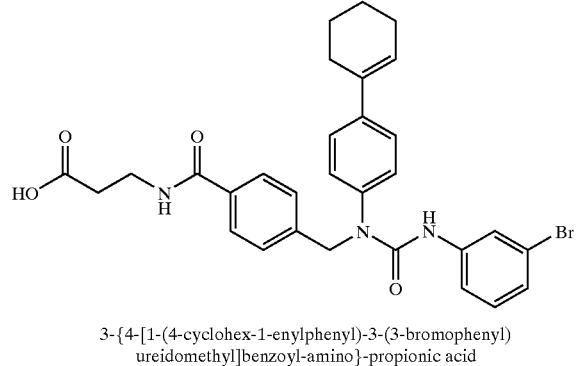

3-{4-[1-(4-cyclohex-1-enylphenyl)-3-(3-bromophenyl)
ureidomethyl]benzoyl-amino}-propionic acid

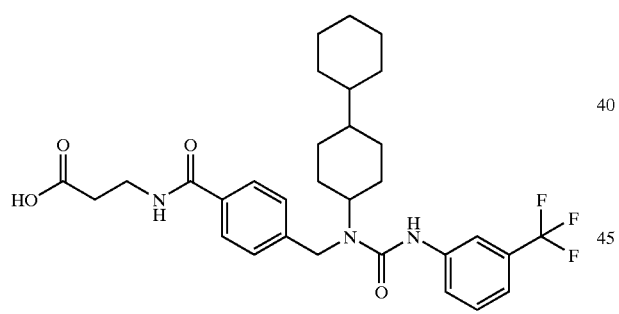

3-{4-[1-(4-cyclohexylcyclohexly)-3-(3-tri-fluoromethylphenyl)
ureidomethyl]benzoyl-amino}propionic acid

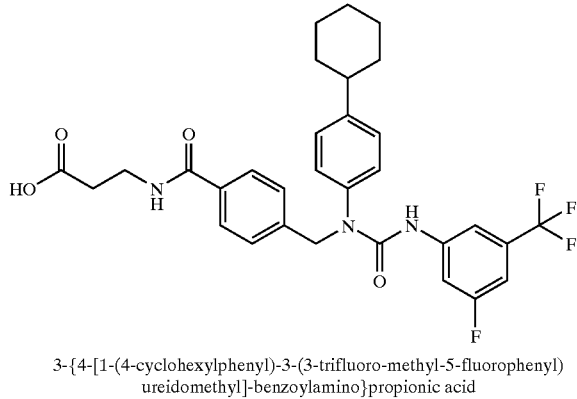

3-{4-[1-(4-cyclohexylphenyl)-3-(3-trifluoro-methyl-5-fluorophenyl)
ureidomethyl]-benzoylamino}propionic acid

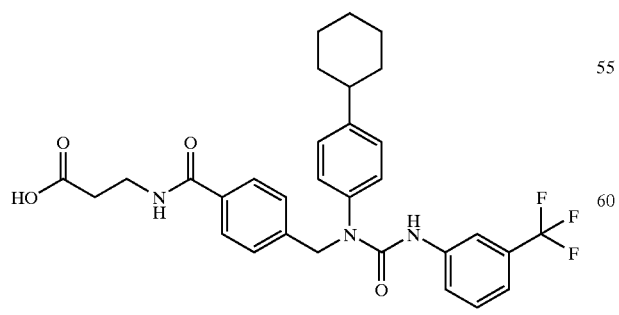

3-{4-[1-(4-cyclohexylphenyl)-3-(3-trifluoro-methylphenyl)
ureidomethyl]benzoyl-amino}propionic acid

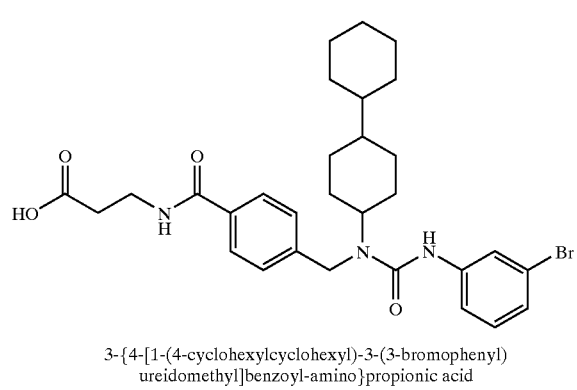

3-{4-[1-(4-cyclohexylcyclohexyl)-3-(3-bromophenyl)
ureidomethyl]benzoyl-amino}propionic acid -continued

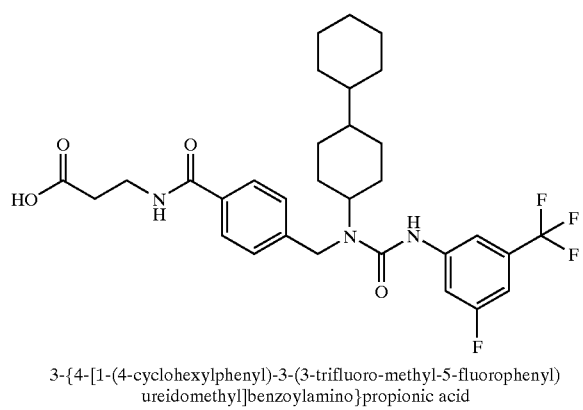

3-{4-[1-(4-cyclohexylphenyl)-3-(3-trifluoro-methyl-5-fluorophenyl)
ureidomethyl]benzoylamino}propionic acid

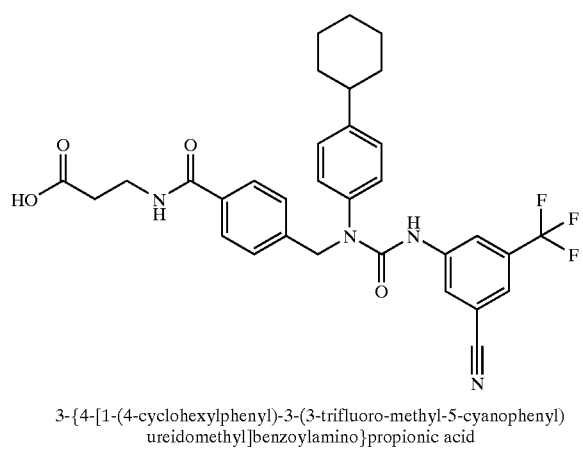

3-{4-[1-(4-cyclohexylphenyl)-3-(3-trifluoro-methyl-5-cyanophenyl)
ureidomethyl]benzoylamino}propionic acid

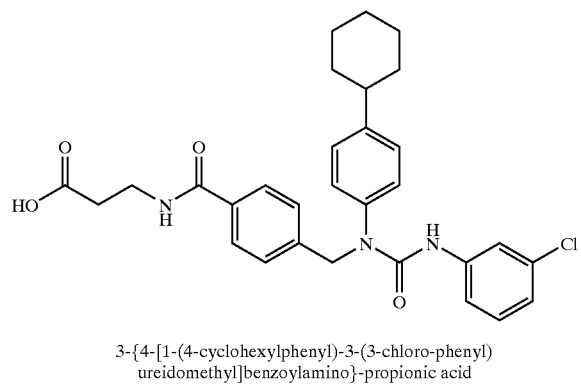

3-{4-[1-(4-cyclohexylphenyl)-3-(3-chloro-phenyl)
ureidomethyl]benzoylamino}-propionic acid

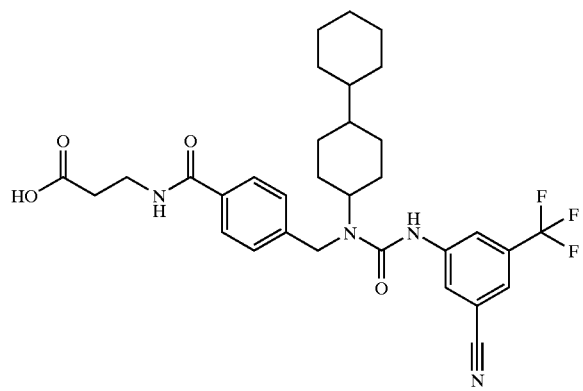

3-{4-[1-(4-cyclohexylcyclohexyl)-3-(3-tri-fluoromethyl-5-cyanophenyl)-
ureidomethyl]benzoylamino}propionic acid -continued

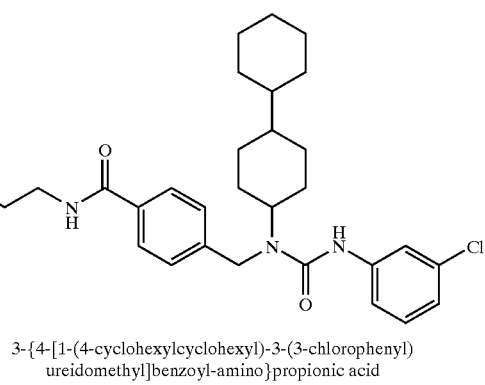

3-{4-[1-(4-cyclohexylcyclohexyl)-3-(3-chlorophenyl)
ureidomethyl]benzoyl-amino}propionic acid

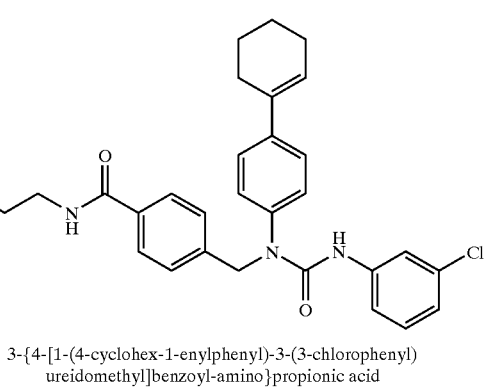

3-{4-[1-(4-cyclohex-1-enylphenyl)-3-(3-chlorophenyl)
ureidomethyl]benzoyl-amino}propionic acid

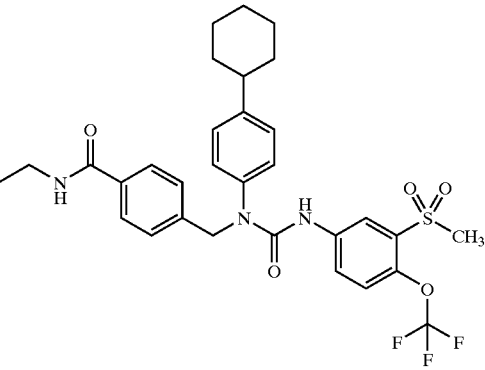

3-{4-[1-(4-cyclohexylphenyl)-3-(3-methyl-sulfonyl-4-
trifluoromethoxyphenyl)ureido-methyl]benzoylamino}propionic acid

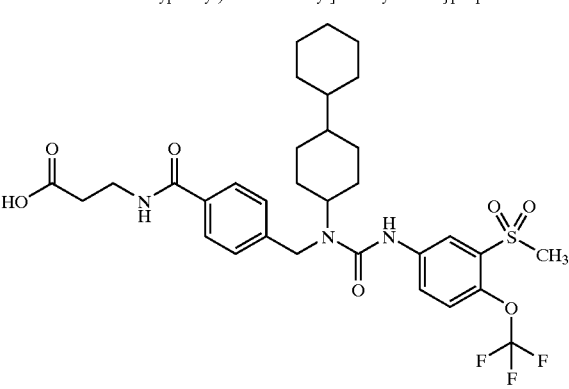

3-{4-[1-(4-cyclohexylcyclohexyl)-3-(3-methylsulfonyl-4-
trifluoromethoxyphenyl)-ureidomethyl]benzoylamino}propionic acid

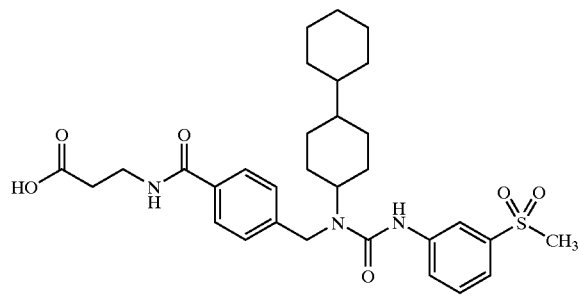

3-{4-[1-(4-cyclohexylcyclohexyl)-3-(3-methylsulfonylphenyl)ureidomethyl]-benzoylamino}propionic acid

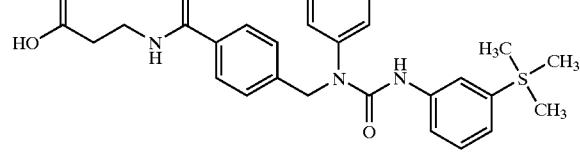

3-{4-[1-(4-cyclohex-1-enylphenyl)-3-(3-tert-butylphenyl)ureidomethyl]benzoyl-amino}propionic acid

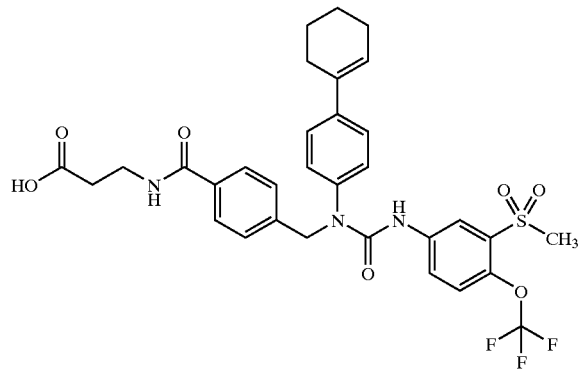

3-{4-[1-(4-cyclohex-1-enylphenyl)-3-(3-methylsulfonyl-4-trifluoromethoxyphenyl)-ureidomethyl]benzoylamino}propionic acid

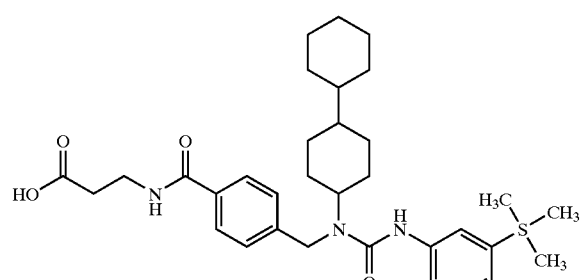

3-{4-[1-(4-cyclohexylcyclohexyl)-3-(3-tert-butylphenyl)ureidomethyl]benzoylamino}-propionic acid

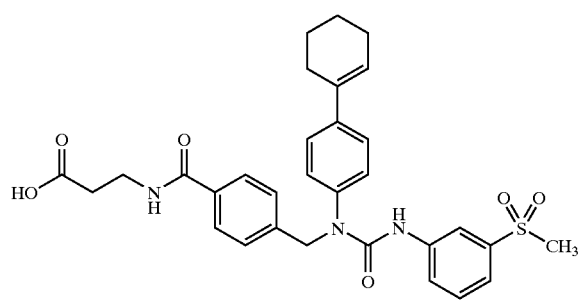

3-{4-[1-(4-cyclohex-1-enylphenyl)-3-(3-methylsulfonylphenyl)ureidomethyl]-benzoylamino}propionic acid

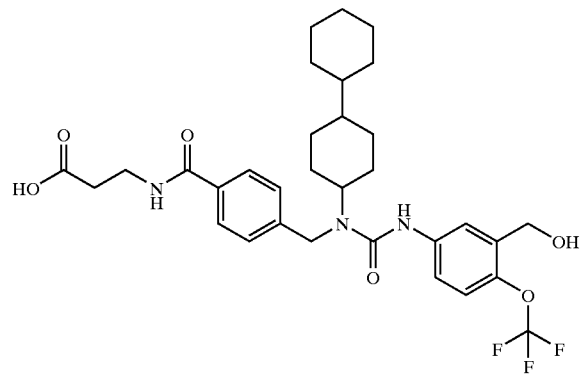

3-{4-[1-(4-cyclohexylcyclohexyl)-3-(3-hydroxymethyl-4-trifluoromethoxyphenyl)-ureidomethyl]benzoylamino}propionic acid

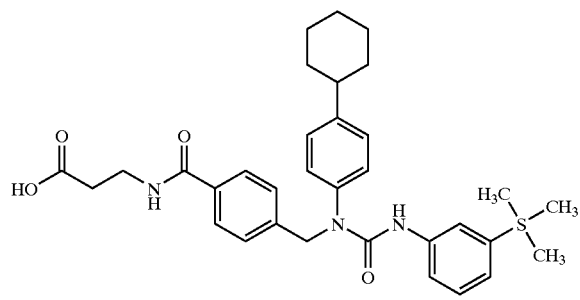

3-{4-[1-(4-cyclohexylphenyl)-3-(3-tert-butylphenyl)ureidomethyl]benzoylamino}propionic acid

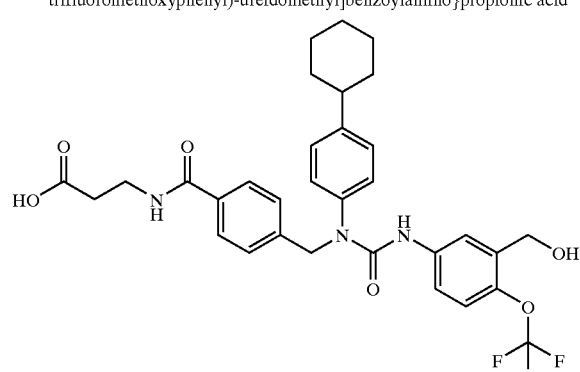

3-{4-[1-(4-cyclohexylphenyl)-3-(3-hydroxy-methyl-4-trifluoromethoxyphenyl)ureido-methyl]benzoylamino}propionic acid -continued

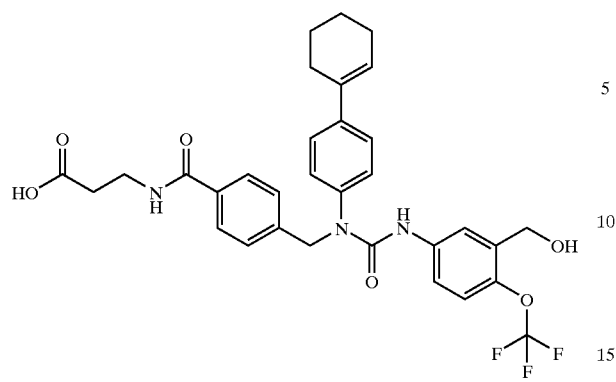

3-{4-[1-(4-cyclohex-1-enylphenyl)-3-(3-hydroxymethyl-4-trifluoromethoxyphenyl)-ureidomethyl]benzoylamino}propionic acid

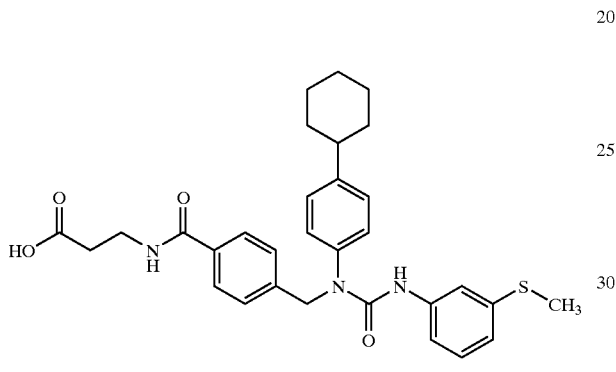

3-{4-[1-(4-cyclohexylphenyl)-3-(3-methylthiophenyl)ureidomethyl]benzoyl-amino}propionic acid

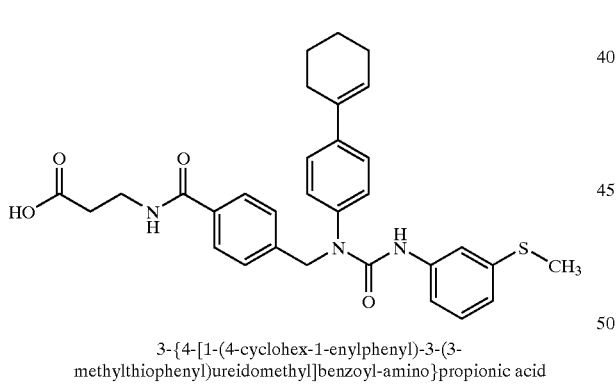

3-{4-[1-(4-cyclohex-1-enylphenyl)-3-(3-methylthiophenyl)ureidomethyl]benzoyl-amino}propionic acid

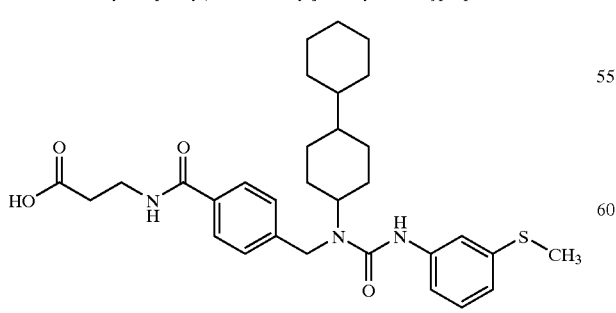

3-{4-[1-(4-cyclohexylcyclohexyl)-3-(3-methylthiophenyl)ureidomethyl]benzoyl-amino}propionic acid -continued

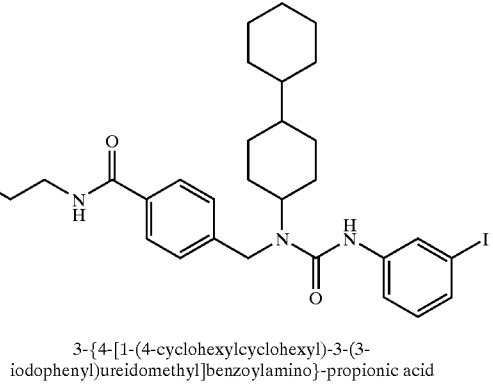

3-{4-[1-(4-cyclohexylcyclohexyl)-3-(3-iodophenyl)ureidomethyl]benzoylamino}-propionic acid

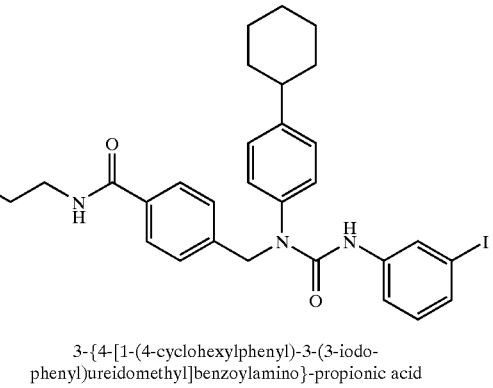

3-{4-[1-(4-cyclohexylphenyl)-3-(3-iodo-phenyl)ureidomethyl]benzoylamino}-propionic acid

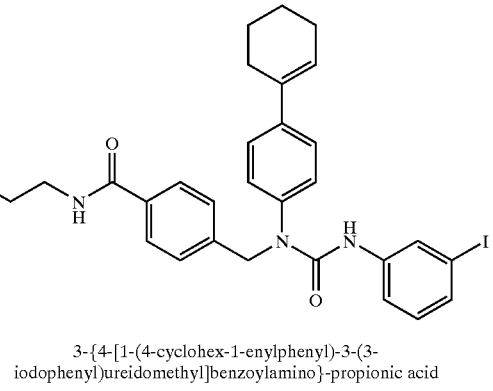

3-{4-[1-(4-cyclohex-1-enylphenyl)-3-(3-iodophenyl)ureidomethyl]benzoylamino}-propionic acid

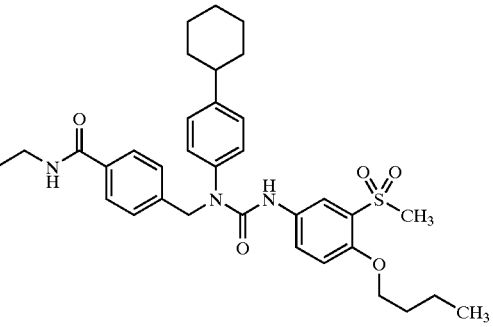

3-{4-[1-(4-cyclohexylphenyl)-3-(3-methyl-sulfony-4-butoxyphenyl)ureidomethyl]-benzoylamino}propionic acid

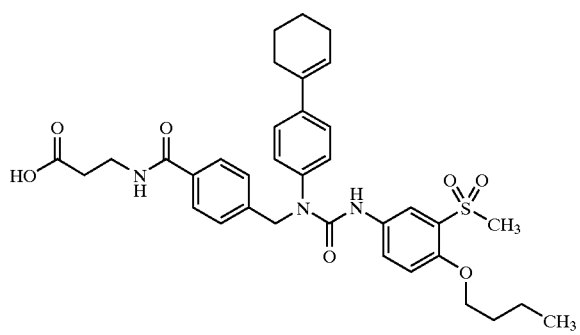

3-{4-[1-(4-cyclohex-1-enylphenyl)-3-(3-methylsulfony-4-butoxyphenyl)ureido-methyl]benzoylamino}propionic acid

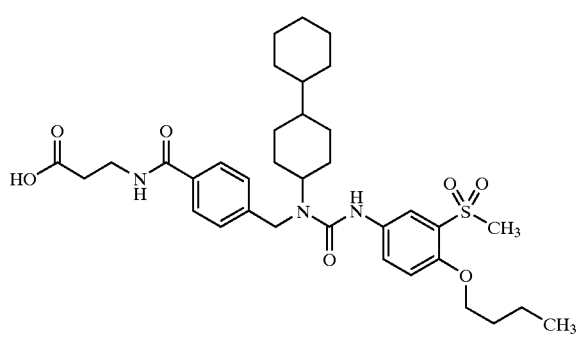

3-{4-[1-(4-cyclohexylcyclohexyl)-3-(3-methylsulfony-4-butoxyphenyl)ureido-methyl]benzoylamino}propionic acid

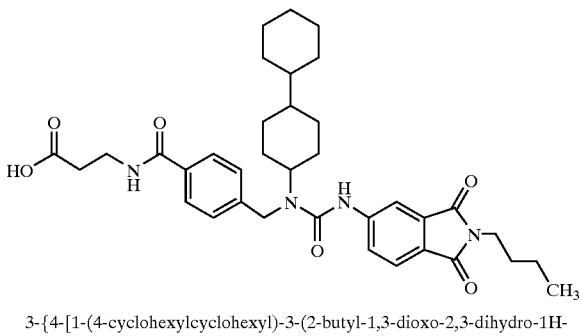

3-{4-[1-(4-cyclohexylcyclohexyl)-3-(2-butyl-1,3-dioxo-2,3-dihydro-1H-isoindol-5-yl)-ureidomethyl]benzoylamino}propionic acid

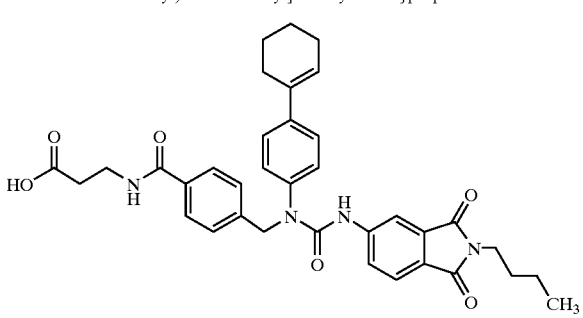

3-{4-[1-(4-cyclohex-1-enylphenyl)-3-(2-butyl-1,3-dioxo-2,3-dihydro-1H-isoindol-5-yl)ureidomethyl]benzoylamino}propionic acid

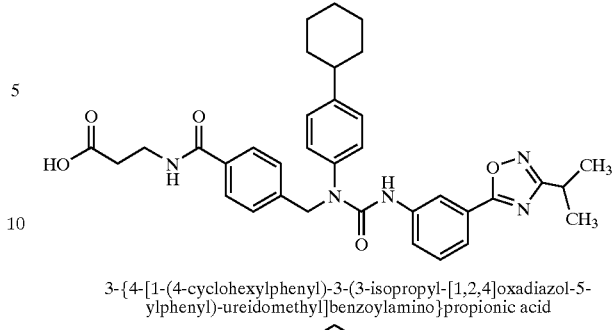

3-{4-[1-(4-cyclohexylphenyl)-3-(3-isopropyl-[1,2,4]oxadiazol-5-ylphenyl)-ureidomethyl]benzoylamino}propionic acid

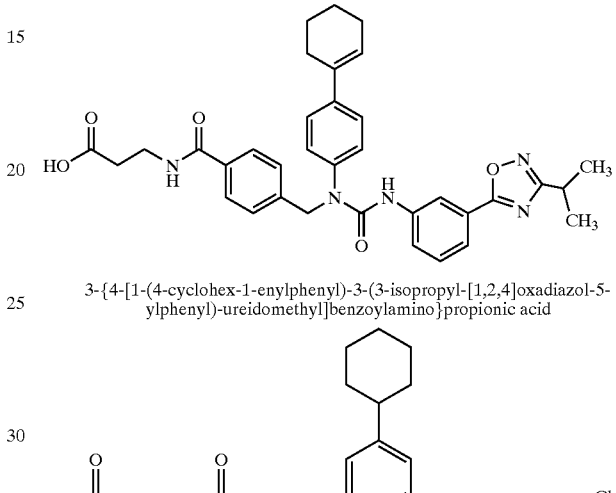

3-{4-[1-(4-cyclohex-1-enylphenyl)-3-(3-isopropyl-[1,2,4]oxadiazol-5-ylphenyl)-ureidomethyl]benzoylamino}propionic acid

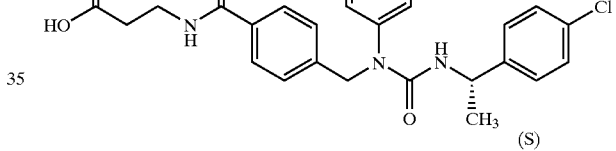

3-{4-[3-[1(S)-(4-chlorophenyl)ethyl]-1-(4-cyclohexylphenyl)ureidomethyl]benzoyl-amino}propionic acid

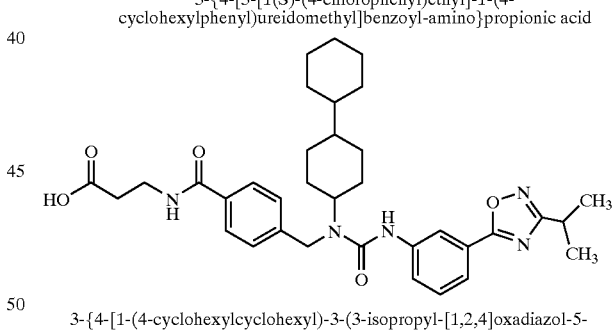

3-{4-[1-(4-cyclohexylcyclohexyl)-3-(3-isopropyl-[1,2,4]oxadiazol-5-ylphenyl)-ureidomethyl]benzoylamino}propionic acid

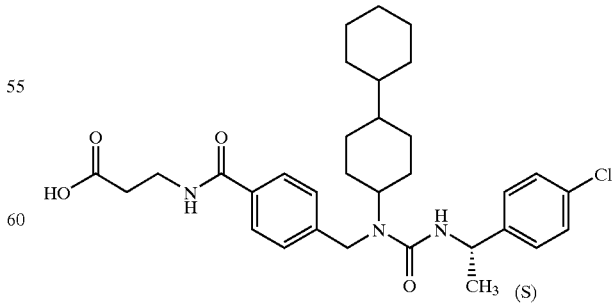

3-{4-[3-[1(S)-(4-chlorophenyl)ethyl]-1-(4-cyclohexylcyclohexyl)ureidomethyl]-benzoylamino}propionic acid

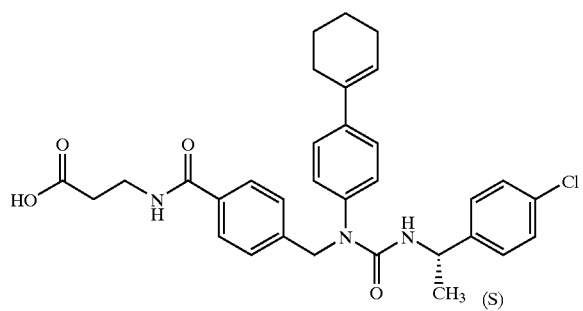

3-{4-[3-[1(S)-(4-chlorophenyl)ethyl]-1-(4-cyclohex-1-enylphenyl)ureidomethyl-benzoylamino}propionic acid

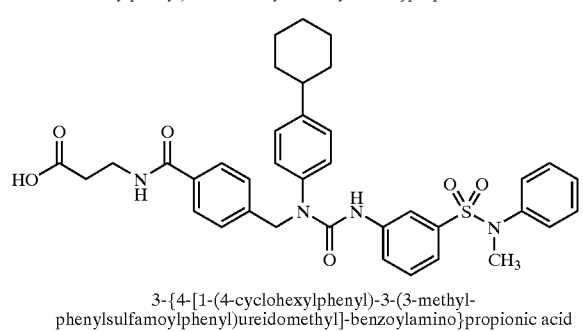

3-{4-[1-(4-cyclohexylphenyl)-3-(3-methyl-phenylsulfamoylphenyl)ureidomethyl]-benzoylamino}propionic acid

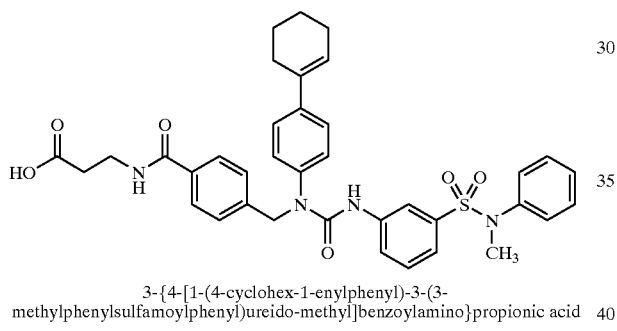

3-{4-[1-(4-cyclohex-1-enylphenyl)-3-(3-methylphenylsulfamoylphenyl)ureido-methyl]benzoylamino}propionic acid

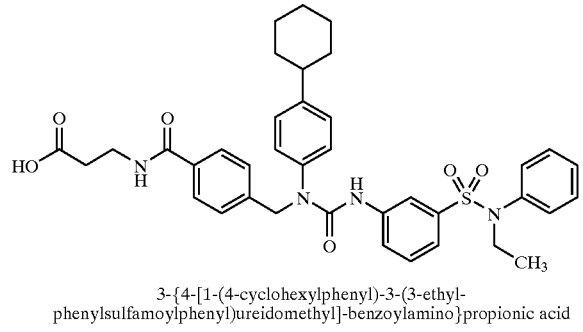

3-{4-[1-(4-cyclohexylphenyl)-3-(3-ethyl-phenylsulfamoylphenyl)ureidomethyl]-benzoylamino}propionic acid

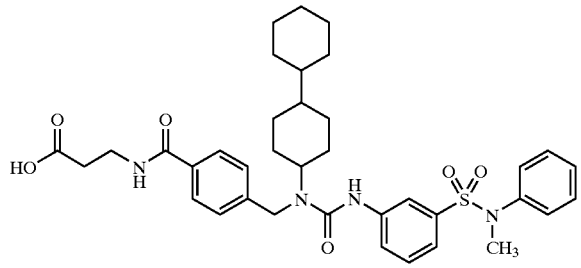

3-{4-[1-(4-cyclohexylcyclohexyl)-3-(3-methylphenylsulfamoylphenyl)ureido-methyl]benzoylamino}propionic acid

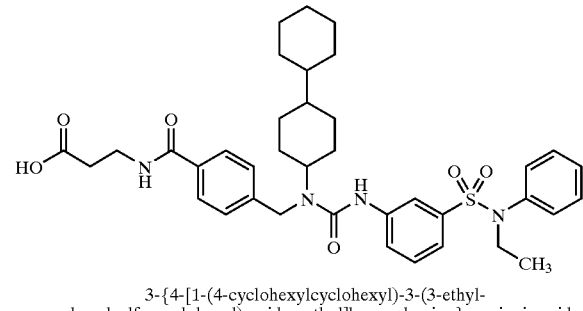

3-{4-[1-(4-cyclohexylcyclohexyl)-3-(3-ethyl-phenylsulfamoylphenyl)ureidomethyl]benzoylamino}propionic acid

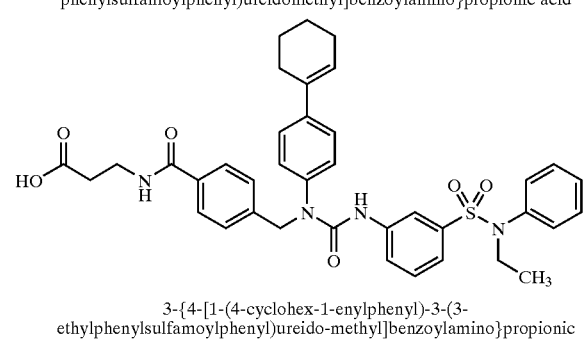

3-{4-[1-(4-cyclohex-1-enylphenyl)-3-(3-ethylphenylsulfamoylphenyl)ureido-methyl]benzoylamino}propionic acid

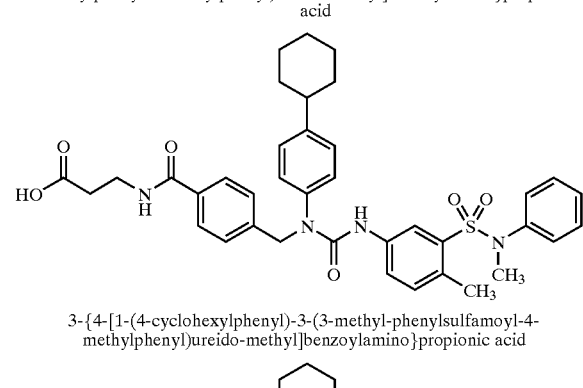

3-{4-[1-(4-cyclohexylphenyl)-3-(3-methyl-phenylsulfamoyl-4-methylphenyl)ureido-methyl]benzoylamino}propionic acid

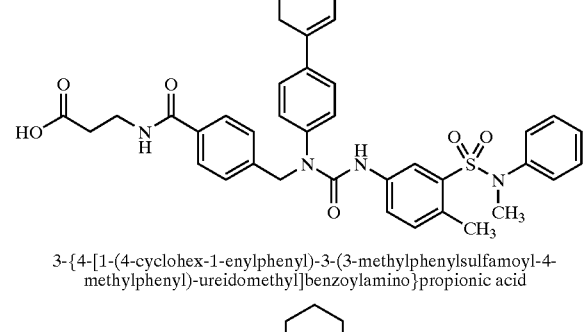

3-{4-[1-(4-cyclohex-1-enylphenyl)-3-(3-methylphenylsulfamoyl-4-methylphenyl)-ureidomethyl]benzoylamino}propionic acid

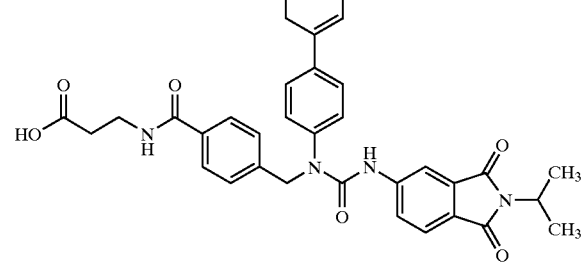

3-{4-[1-(4-cyclohex-1-enylphenyl)-3-(2-iso-propyl-1,3-dioxo-2,3-dihydro-1H-isoindol-5-yl)ureidomethyl]benzoylamino}propionic acid

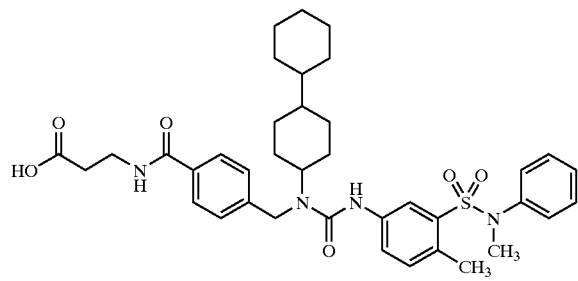

3-{4-[1-(4-cyclohexylcyclohexyl)-3-(3-methylphenylsulfamoyl-4-methylphenyl)-ureidomethyl]benzoylamino}propionic acid

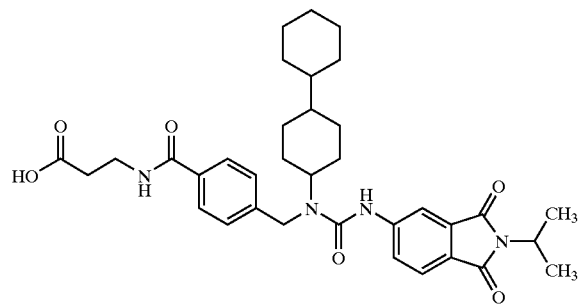

3-{4-[1-(4-cyclohexylcyclohexyl)-3-(2-iso-propyl-1,3-dioxo-2,3-dihydro-1H-isoindol-5-yl)ureidomethyl]benzoylamino}propionic acid

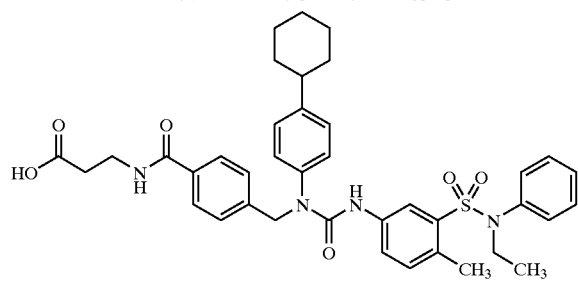

3-{4-[1-(4-cyclohexylphenyl)-3-(3-ethyl-phenylsulfamoyl-4-methylphenyl)ureidomethyl]benzoylamino}propionic acid

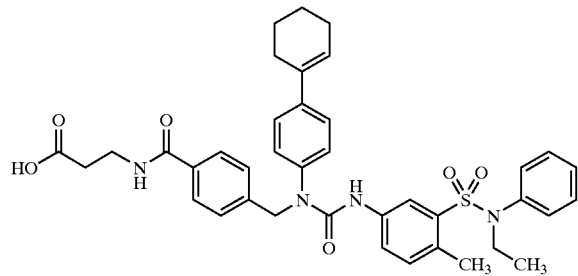

3-{4-[1-(4-cyclohex-1-enylphenyl)-3-(3-ethylphenylsulfamoyl-4-methylphenyl)-ureidomethyl]benzoylamino}propionic acid

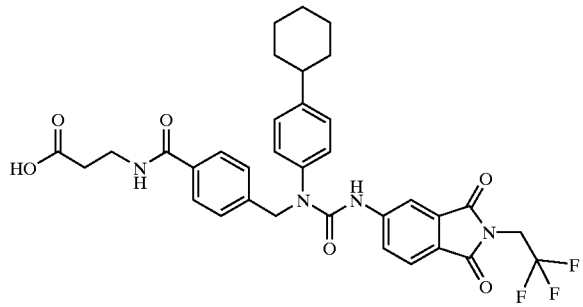

3-{4-[1-(4-cyclohexylphenyl)-3-(2-[2,2,2-trifluoroethyl]-1,3-dioxo-2,3-dihydro-1H-isoindol-5-yl)ureidomethyl]benzoylamino}-propionic acid

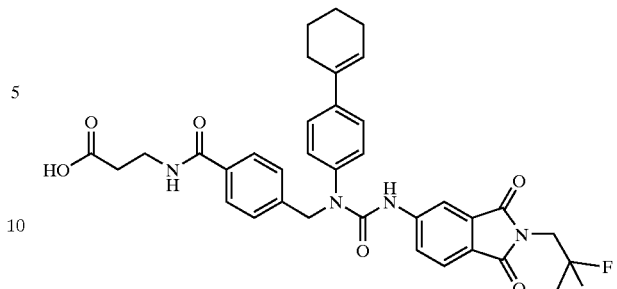

3-{4-[1-(4-cyclohex-1-enylphenyl)-3-(2-[2,2,2-trifluoroethyl]-1,3-dioxo-2,3-dihydro-1H-isoindol-5-yl)ureidomethyl]benzoyl-amino}propionic acid

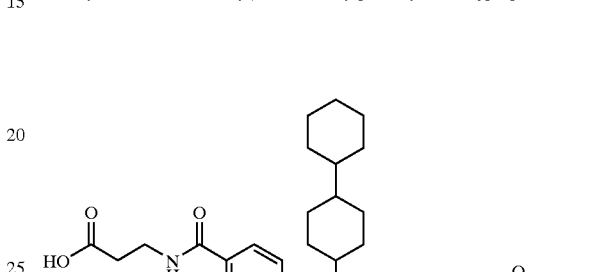

3-{4-[1-(4-cyclohexylcyclohexyl)-3-(2-[2,2,2-trifluoroethyl]-1,3-dioxo-2,3-dihydro-1H-isoindol-5-yl)ureidomethyl]benzoyl-amino}propionic acid

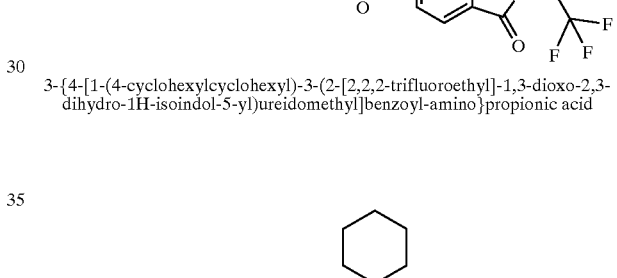

3-{4-[1-(4-cyclohexylcyclohexyl)-3-(5-methylsulfonylthiophen-2-yl)ureidomethyl]-benzoylamino}propionic acid

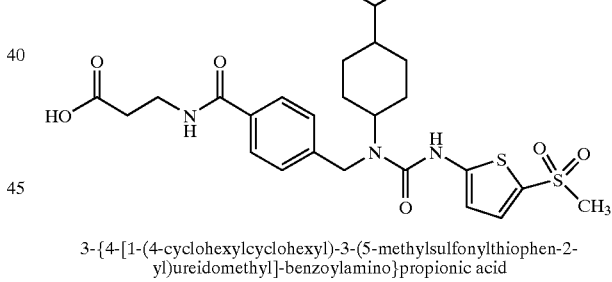

3-{4-[1-(4-cyclohexylphenyl)-3-(5-methyl-sulfonylthiophen-2-yl)ureidomethyl]-benzoylamino}propionic acid -continued

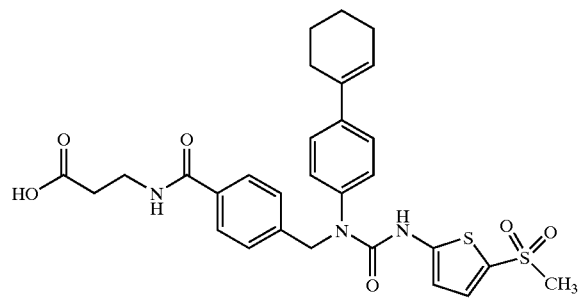

3-{4-[1-(4-cyclohex-1-enylcyclohexyl)-3-(5-methylsulfonylthiophen-2-yl)ureidomethyl]-benzoylamino}propionic acid

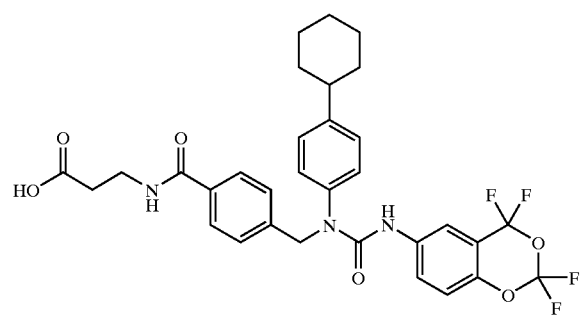

3-{4-[1-(4-cyclohexylphenyl)-3-(2,2,4,4-tetra-fluorobenzo[1,3]dioxin-6-yl)ureidomethyl]-benzoylamino}propionic acid

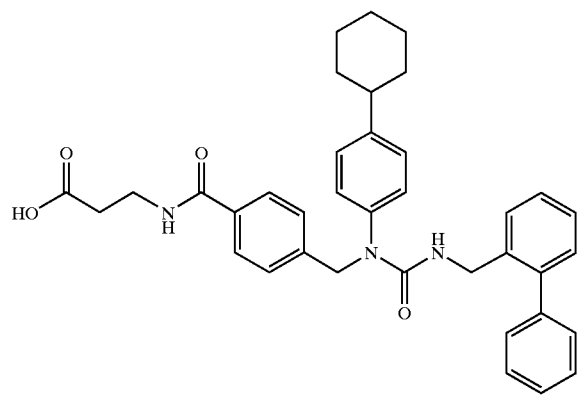

3-{4-[3-biphenyl-2-ylmethyl-1-(4-cyclohexylphenyl)ureidomethyl]benzoylamino}-propionic acid

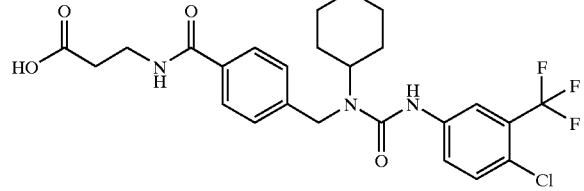

3-{4-[1-(4-cyclohexylcyclohexyl)-3-(3-trifluoromethyl-4-chlorophenyl)ureido-methyl]benzoylamino}propionic acid

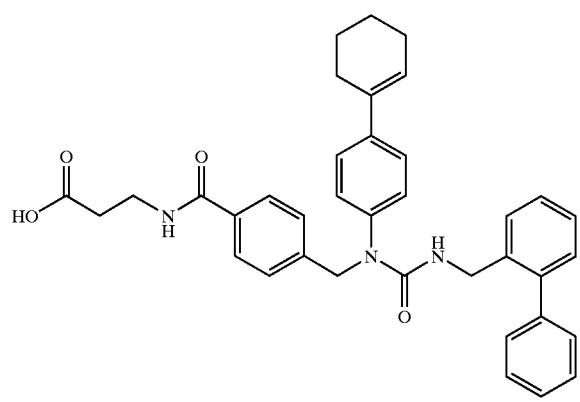

3-{4-[3-biphenyl-2-ylmethyl-1-(4-cyclohex-1-enylphenyl)ureidomethyl]benzoylamino}-propionic acid

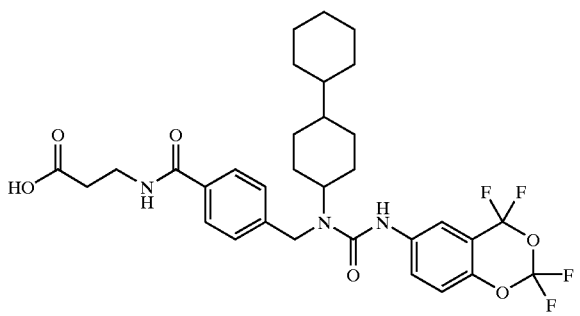

3-{4-[1-(4-cyclohexylcyclohexyl)-3-(2,2,4,4-tetrafluorobenzo[1,3]diox in-6-yl)ureidomethyl]-benzoylamino}propionic acid

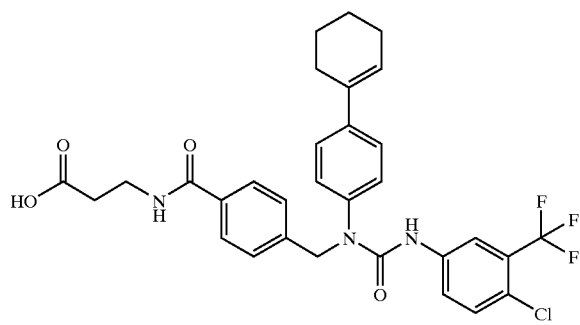

3-{4-[1-(4-cyclohex-1-enylphenyl)-3-(3-tri-fluoromethyl-4-chlorophenyl)ureido-methyl]benzoylamino}propionic acid

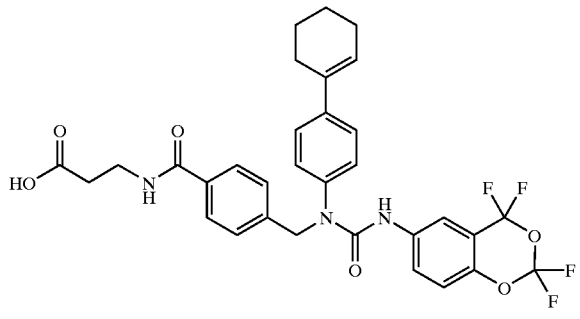

3-{4-[1-(4-cyclohex-1-enylphenyl)-3-(2,2,4,4-tetrafluorobenzo[1,3]diox in-6-yl)ureidomethyl]benzoylamino}propionic acid -continued

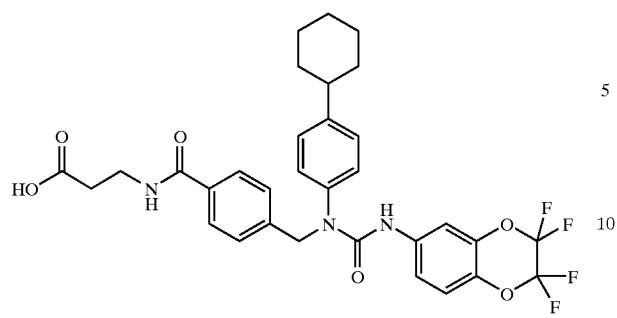

3-{4-[1-(4-cyclohexylphenyl)-3-(3,3,4,4-tetra-fluorobenzo[1,4]dioxin-6-yl)ureidomethyl]-benzoylamino}propionic acid

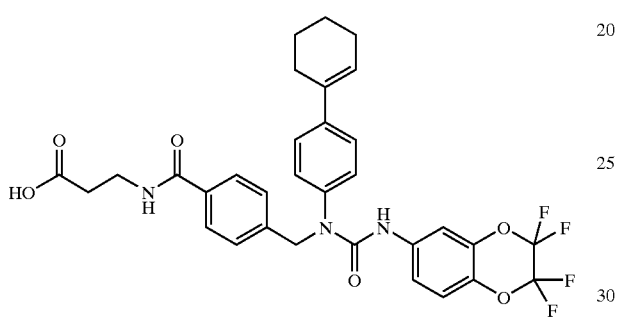

3-{4-[1-(4-cyclohex-1-enylphenyl)-3-(3,3,4,4-tetrafluorobenzo[1,4]dioxin-6-yl)ureidomethyl]benzoylamino}propionic acid

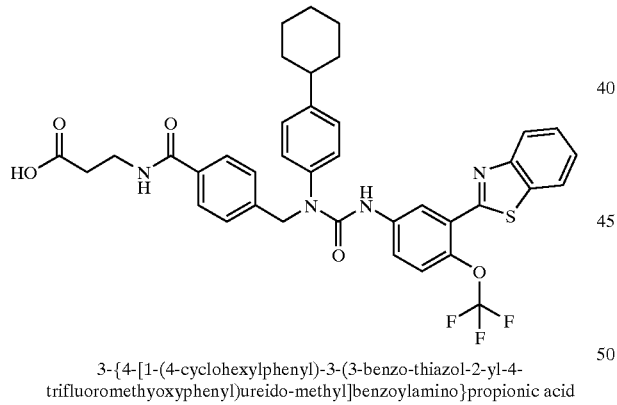

3-{4-[1-(4-cyclohexylphenyl)-3-(3-benzo-thiazol-2-yl-4-trifluoromethyoxyphenyl)ureido-methyl]benzoylamino}propionic acid

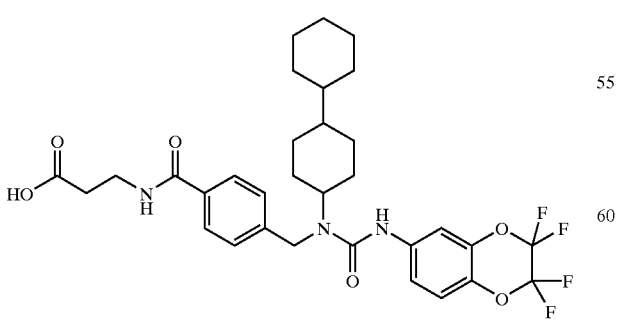

3-{4-[1-(4-cyclohexylcyclohexyl)-3-(3,3,4,4-tetrafluorobenzo[1,4]diox in-6-yl)ureidomethyl]benzoylamino}propionic acid -continued

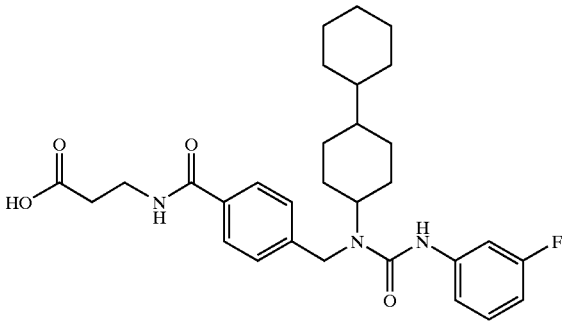

3-{4-[1-(4-cyclohexylcyclohexyl)-3-(3-fluoro-phenyl)ureidomethyl]benzoylamino}propionic acid

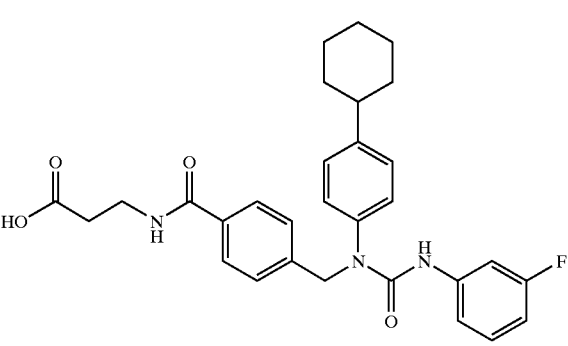

3-{4-[1-(4-cyclohexylphenyl)-3-(3-fluoro-phenyl)ureidomethyl]benzoylamino}-propionic acid

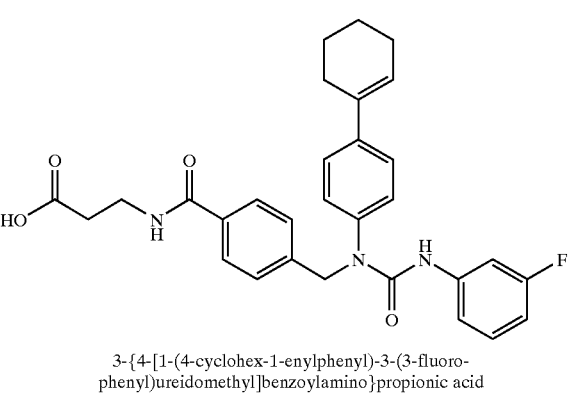

3-{4-[1-(4-cyclohex-1-enylphenyl)-3-(3-fluoro-phenyl)ureidomethyl]benzoylamino}propionic acid

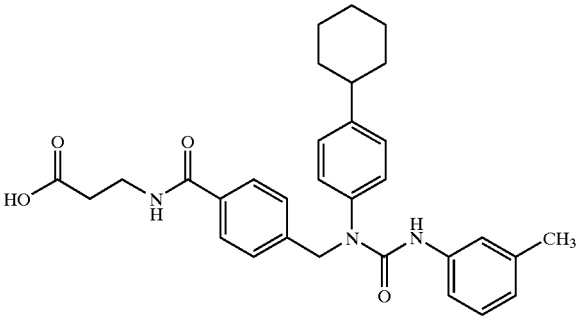

3-{4-[1-(4-cyclohexylphenyl)-3-(3-methyl-phenyl)ureidomethyl]benzoylamino}-propionic acid -continued

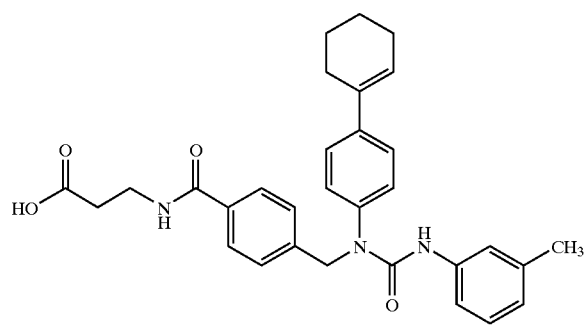

3-{4-[1-(4-cyclohex-1-enylphenyl)-3-(3-methylphenyl)ureidomethyl]benzoylamino}-propionic acid

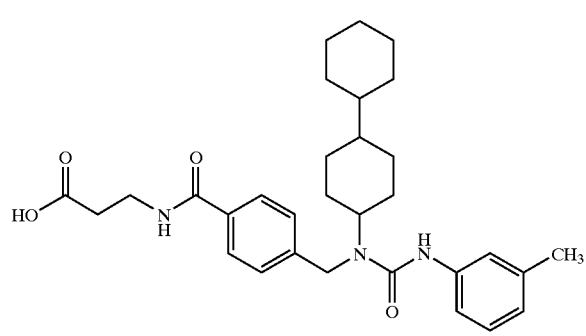

3-{4-[1-(4-cyclohexylcyclohexyl)-3-(3-methylphenyl)ureidomethyl]benzoyl-amino}propionic acid

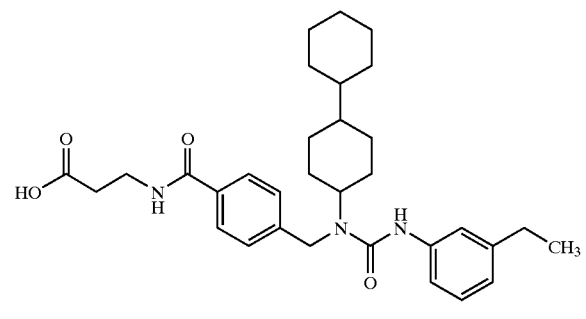

3-{4-[1-(4-cyclohexylcyclohexyl)-3-(3-ethyl-phenyl)ureidomethyl]benzoylamino}propionic acid

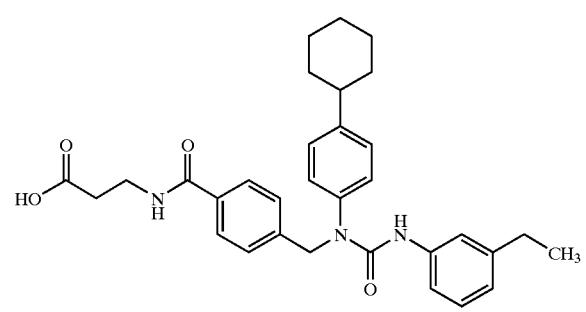

3-{4-[1-(4-cyclohexylphenyl)-3-(3-ethyl-phenyl)ureidomethyl]benzoylamino}-propionic acid -continued

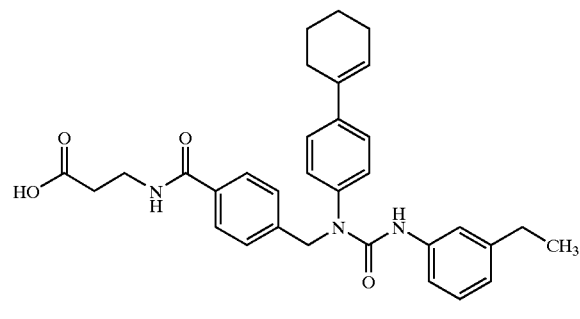

3-{4-[1-(4-cyclohex-1-enylphenyl)-3-(3-ethyl-phenyl)ureidomethyl]benzoylamino}propionic acid

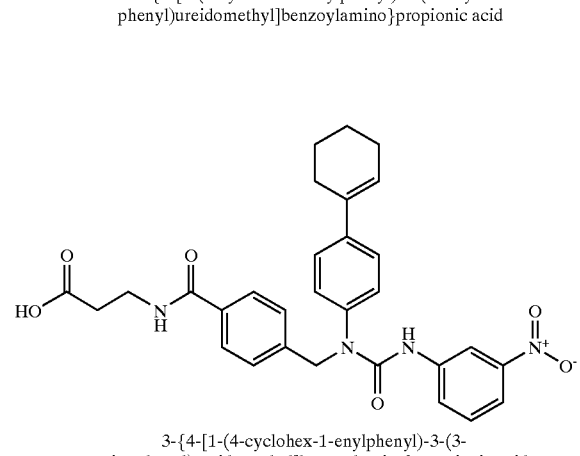

3-{4-[1-(4-cyclohex-1-enylphenyl)-3-(3-nitrophenyl)ureidomethyl]benzoylamino}-propionic acid

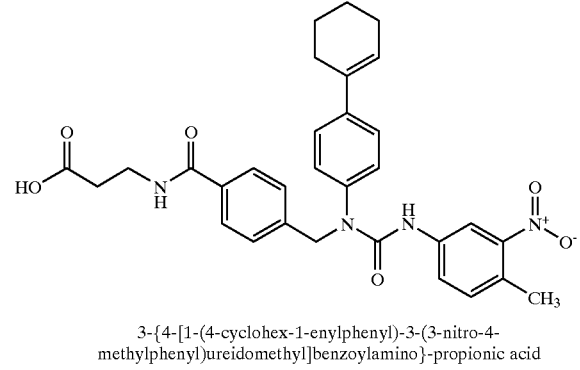

3-{4-[1-(4-cyclohex-1-enylphenyl)-3-(3-nitro-4-methylphenyl)ureidomethyl]benzoylamino}-propionic acid

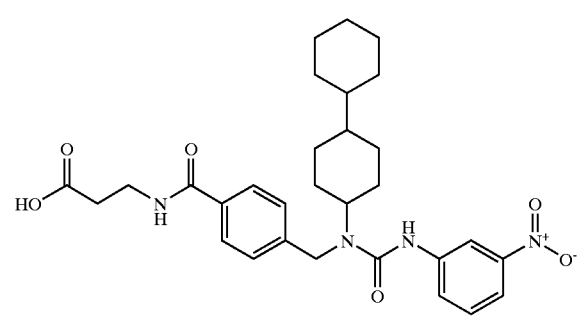

3-{4-[1-(4-cyclohexylcyclohexyl)-3-(3-nitrophenyl)ureidomethyl]benzoylamino}-propionic acid

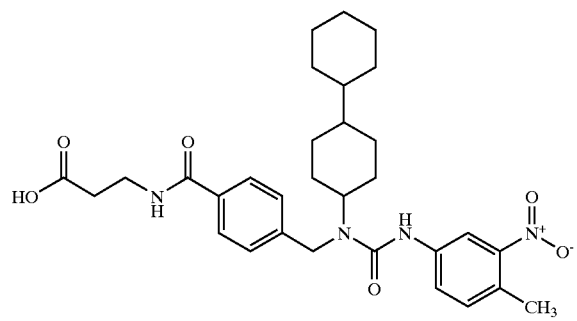

3-{4-[1-(4-cyclohexylcyclohexyl)-3-(3-nitro-4-methylphenyl)ureidomethyl]benzoylamino}-propionic acid

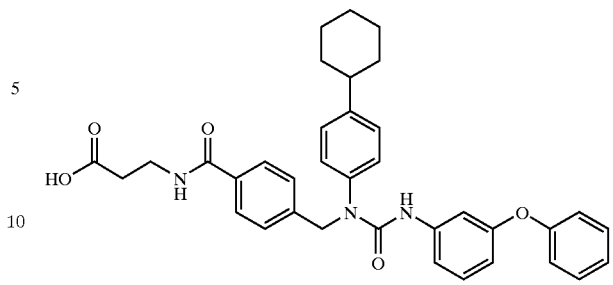

3-{4-[1-(4-cyclohexylphenyl)-3-(3-phenoxyphenyl)ureidomethyl]benzoylamino}propionic acid

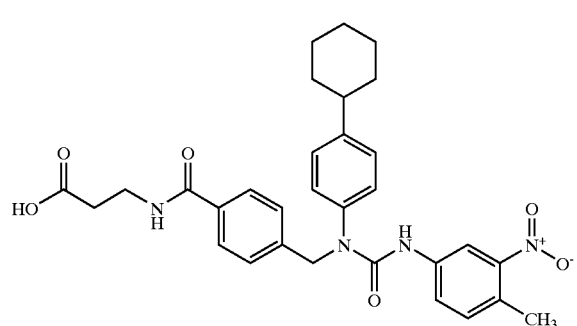

3-{4-[1-(4-cyclohexylphenyl)-3-(3-nitro-4-methylphenyl)ureidomethyl]benzoyl-amino}propionic acid

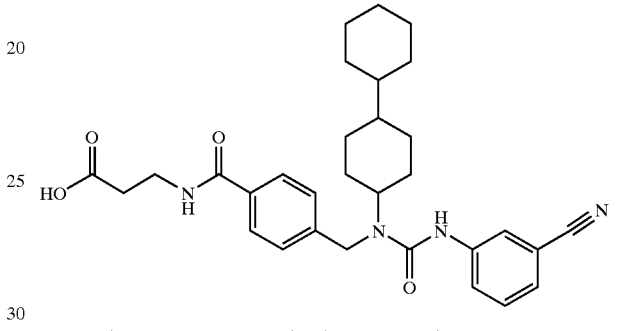

3-{4-[1-(4-cyclohexylcyclohexyl)-3-(3-cyanophenyl)ureidomethyl]benzoyl-amino}propionic acid

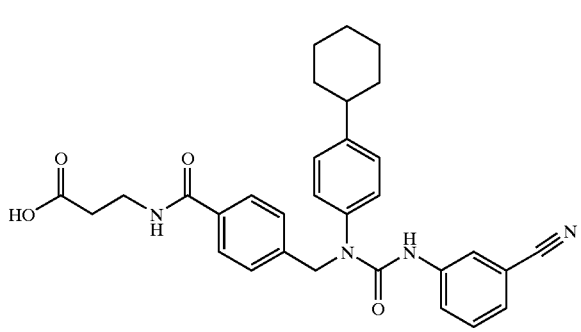

3-{4-[1-(4-cyclohexylphenyl)-3-(3-cyanophenyl)ureidomethyl]benzoylamino}propionic acid

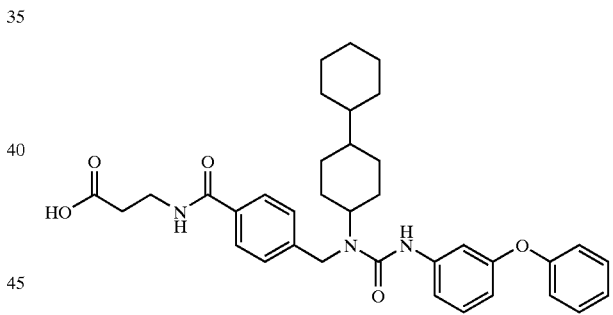

3-{4-[1-(4-cyclohexylcyclohexyl)-3-(3-phenoxyphenyl)ureidomethyl]benzoylamino}-propionic acid

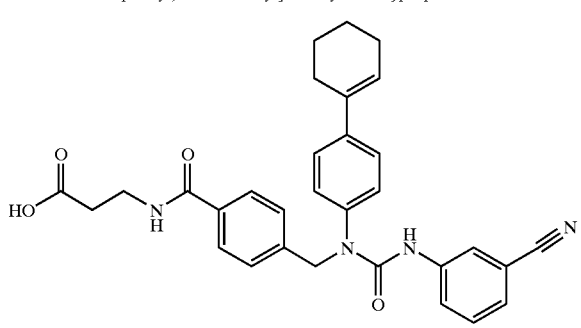

3-{4-[1-(4-cyclohex-1-enylphenyl)-3-(3-cyanophenyl)ureidomethyl]benzoyl-amino}propionic acid

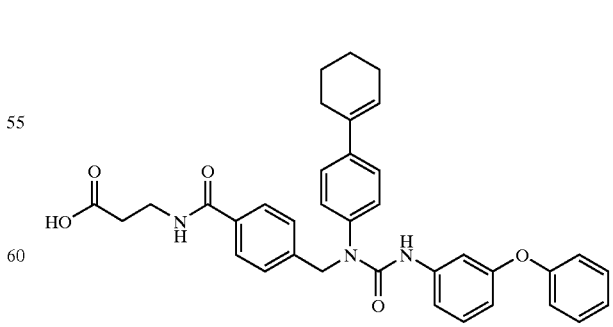

3-{4-[1-(4-cyclohex-1-enylphenyl)-3-(3-phenoxyphenyl)ureidomethyl]benzoyl-amino}propionic acid

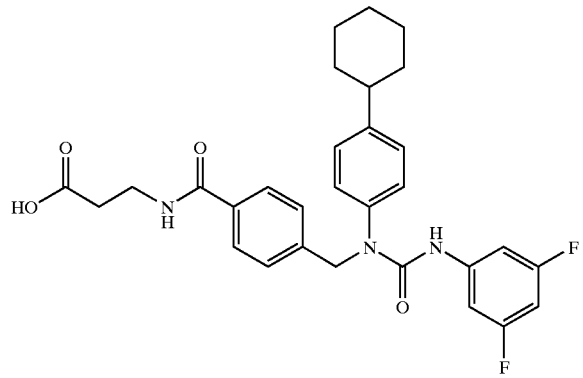

3-{4-[1-(4-cyclohexylphenyl)-3-(3,5-difluoro-phenyl)ureidomethyl]benzoylamino}propionic acid

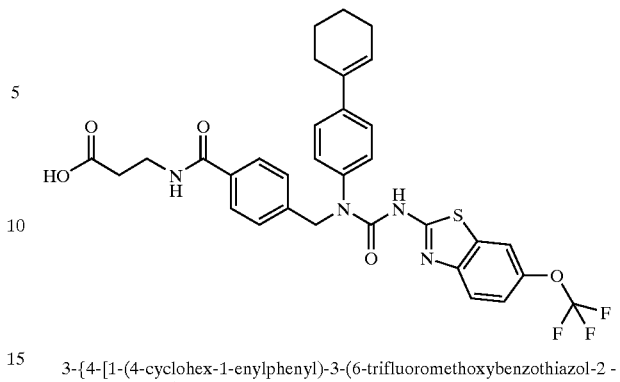

3-{4-[1-(4-cyclohex-1-enylphenyl)-3-(6-trifluoromethoxybenzothiazol-2-yl)ureido-methyl]benzoylamino}propionic acid

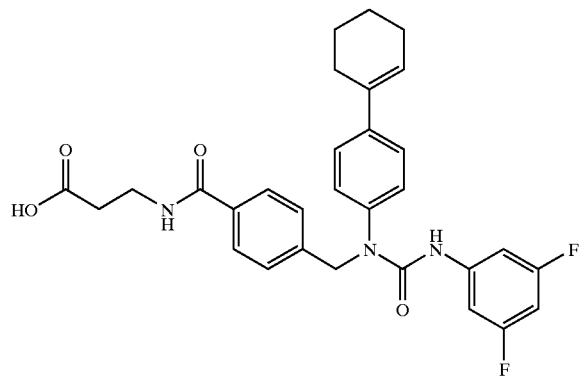

3-{4-[1-(4-cyclohex-1-enylphenyl)-3-(3,5-difluorophenyl)ureidomethyl]benzoyl-amino}propionic acid

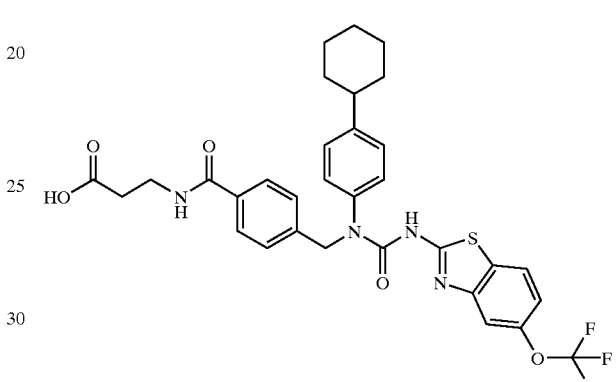

3-{4-[1-(4-cyclohexylphenyl)-3-(5-trifluoro-methoxybenzothiazol-2-yl)ureidomethyl]-benzoylamino}propionic acid

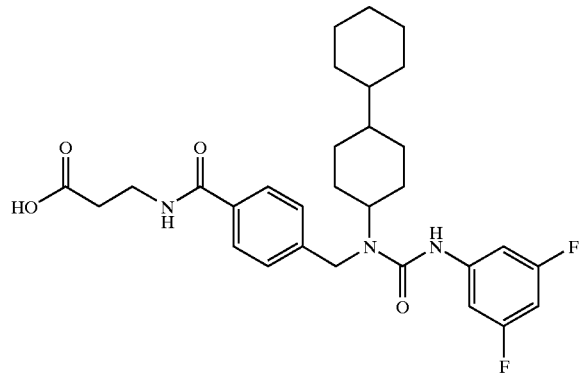

3-{4-[1-(4-cyclohexylcyclohexyl)-3-(3,5-difluorophenyl)ureidomethyl]benzoylamino}-propionic acid

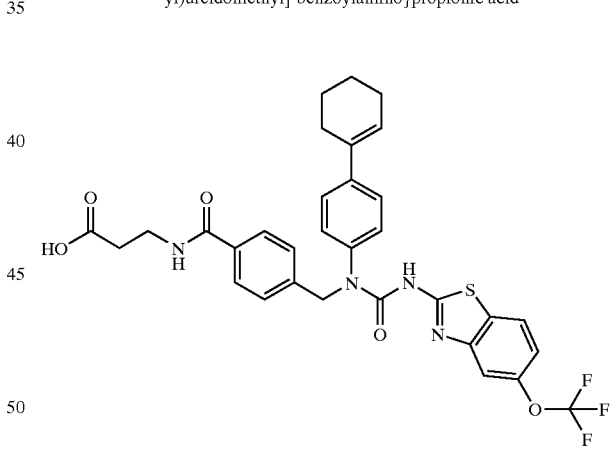

3-{4-[1-(4-cyclohex-1-enylphenyl)-3-(5-trifluoromethoxybenzothiazol-2-yl)ureido-methyl]benzoylamino}propionic acid

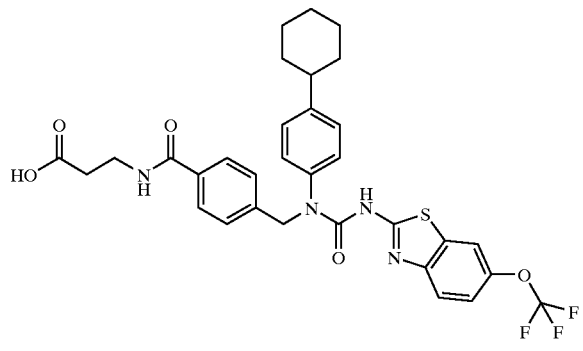

3-{4-[1-(4-cyclohexylphenyl)-3-(6-trifluoro-methoxybenzothiazol-2-yl)ureidomethyl]-benzoylamino}propionic acid

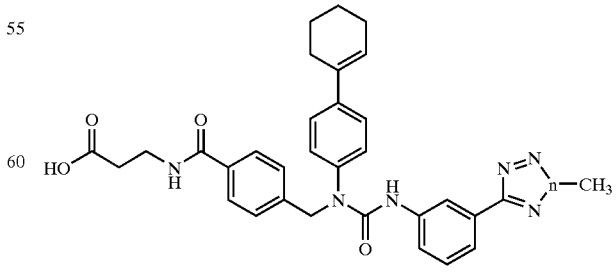

3-{4-[1-(4-cyclohex-1-enylphenyl)-3-(3-(2-methyl-2H-tetrazol-5-yl)phenyl)ureidomethyl]-benzoylamino}propionic acid

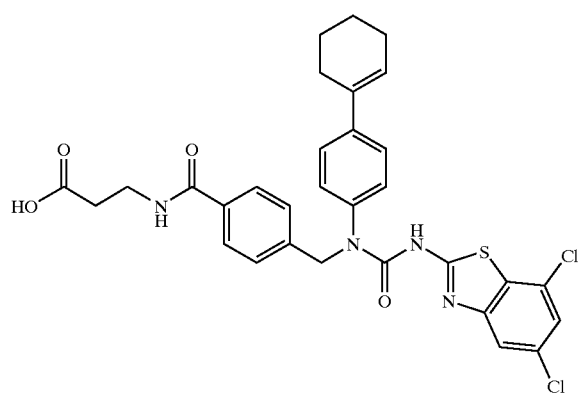

3-{4-[1-(4-cyclohex-1-enylphenyl)-3-(5,7-dichlorobenzothiazol-2-yl)ureidomethyl]-benzoylamino}propionic acid

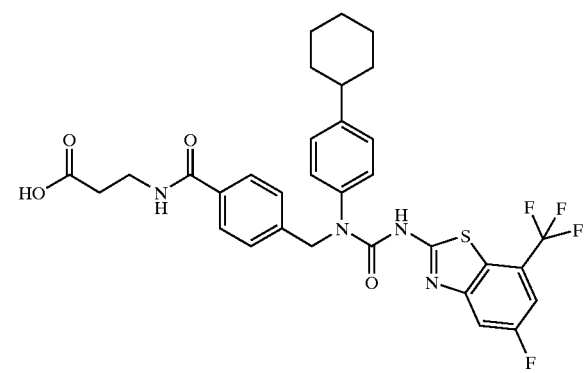

3-{4-[1-(4-cyclohexylphenyl)-3-(5-fluoro-7-trifluoromethylbenzothiazol-2-yl)ureido-methyl]benzoylamino}propionic acid

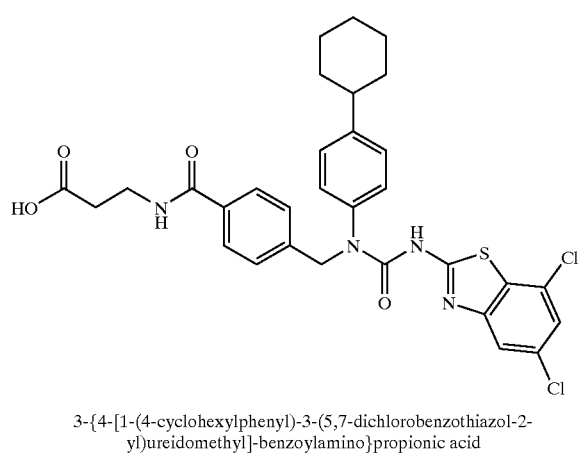

3-{4-[1-(4-cyclohexylphenyl)-3-(5,7-dichlorobenzothiazol-2-yl)ureidomethyl]-benzoylamino}propionic acid

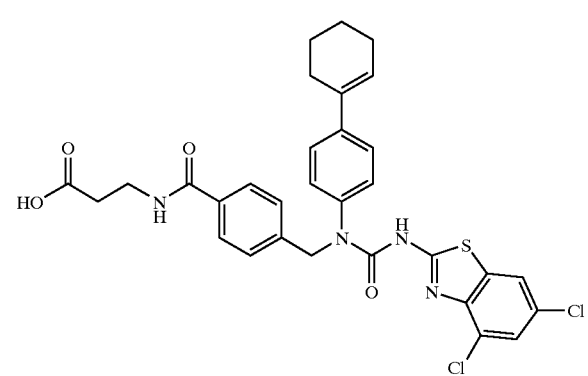

3-{4-[1-(4-cyclohex-1-enylphenyl)-3-(4,6-di-chlorobenzothiazol-2-yl)ureidomethyl]benzoyl-amino}propionic acid

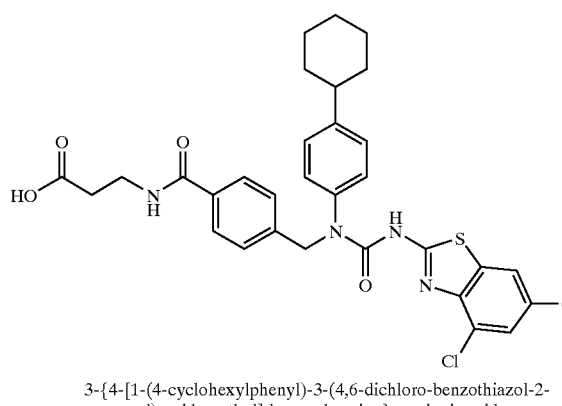

3-{4-[1-(4-cyclohexylphenyl)-3-(4,6-dichloro-benzothiazol-2-yl)ureidomethyl]-benzoyl-amino}propionic acid

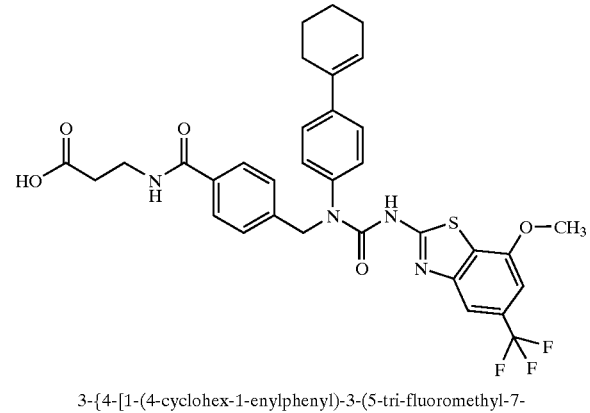

3-{4-[1-(4-cyclohex-1-enylphenyl)-3-(5-tri-fluoromethyl-7-methoxybenzothiazol-2-yl)ureidomethyl]benzoylamino}propionic acid

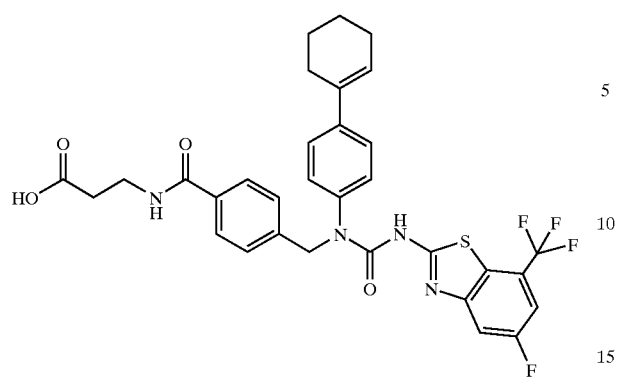

3-{4-[1-(4-cyclohex-1-enylphenyl)-3-(5-fluoro-7-trifluoromethylbenzothiazol-2-yl)ureido-methyl]benzoylamino}propionic acid

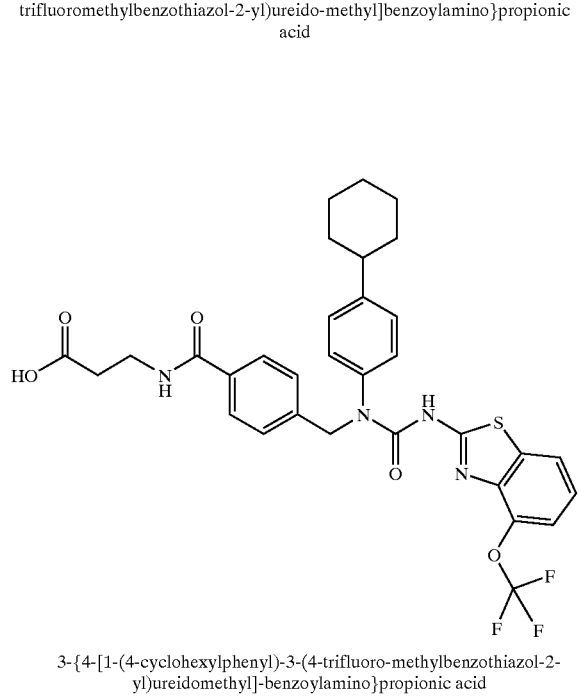

3-{4-[1-(4-cyclohexylphenyl)-3-(4-trifluoro-methylbenzothiazol-2-yl)ureidomethyl]-benzoylamino}propionic acid 3-{4-[1-(4-cyclohex-1-enylphenyl)-3-(4-tri-fluoromethoxybenzothiazol-2-yl)ureido-methyl]benzoylamino}propionic acid

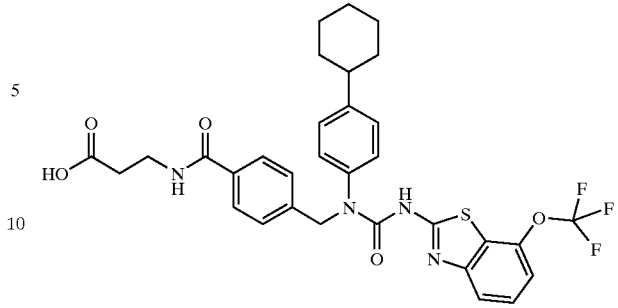

3-{4-[1-(4-cyclohexylphenyl)-3-(7-trifluoro-methoxybenzothiazol-2-yl)ureidomethyl]benzoylamino}propionic acid

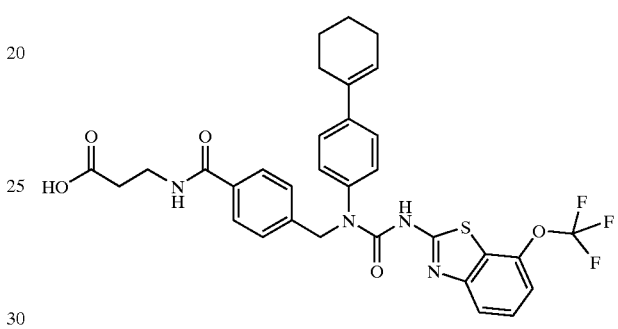

3-{4-[1-(4-cyclohex-1-enylphenyl)-3-(7-tri-fluoromethoxybenzothiazol-2-yl)ureido-methyl]benzoylamino}propionic acid

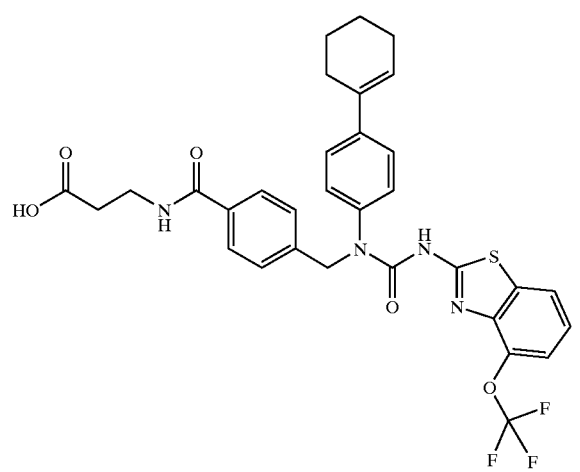

3-{4-[1-(4-cyclohexylphenyl)-3-(4-fluro-6-trifluoromethylbenzothiazol-2-yl)ureido-methyl]benzoylamino}propionic acid

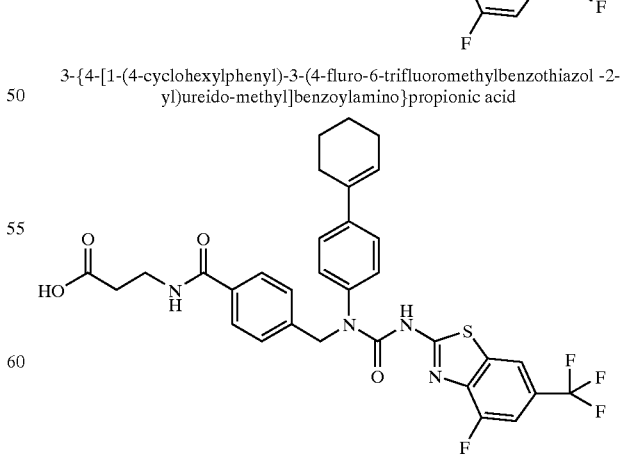

3-{4-[1-(4-cyclohex-1-enylphenyl)-3-(4-fluro-6-trifluoromethylbenzothiazol-2-yl)ureido-methyl]benzoylamino}propionic acid

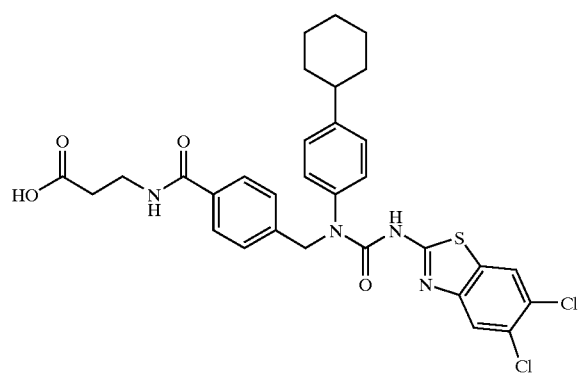

3-{4-[1-(4-cyclohexylphenyl)-3-(5,6-dichlorobenzothiazol-2-yl)ureidomethyl]-benzoylamino}propionic acid

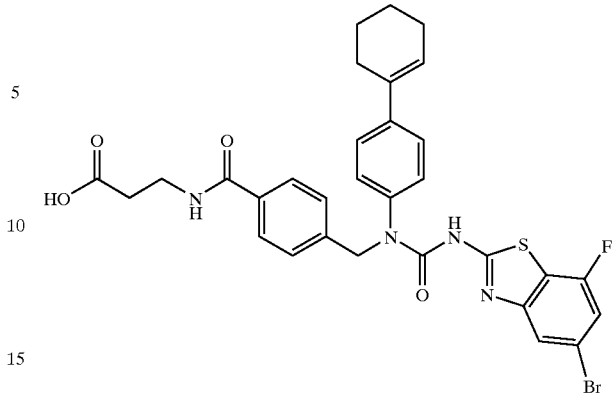

3-{4-[1-(4-cyclohex-1-enylphenyl)-3-(5-bromo-7-fluorobenzothiazol-2-yl)ureidomethyl]-benzoylamino}propionic acid

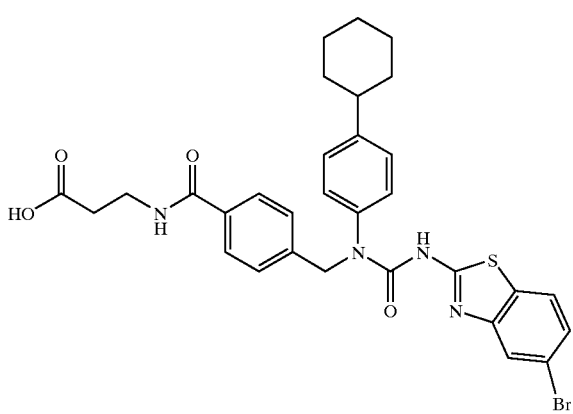

3-{4-[1-(4-cyclohexylphenyl)-3-(5-bromo-benzothiazol-2-yl)ureidomethyl]-benzoyl-amino}propionic acid

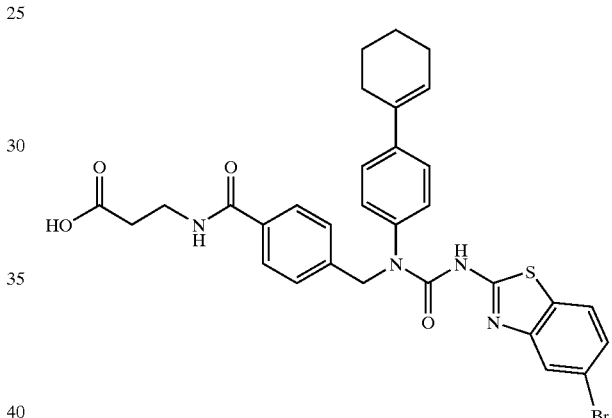

3-{4-[1-(4-cyclohex-1-enylphenyl)-3-(5-bromobenzothiazol-2-yl)ureidomethyl]-benzoylamino}propionic acid

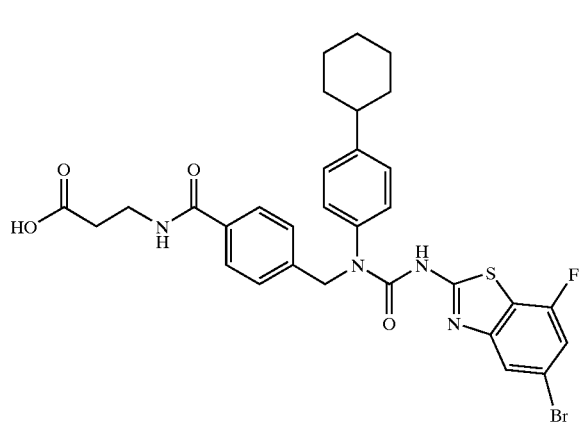

3-{4-[1-(4-cyclohexylphenyl)-3-(5-bromo-7-fluorobenzothiazol-2-yl)ureidomethyl]-benzoylamino}propionic acid

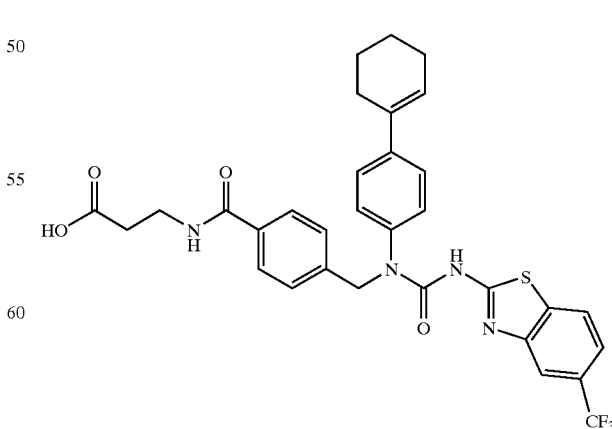

3-{4-[1-(4-cyclohex-1-enylphenyl)-3-(5-trifluoromethylbenzothiazol-2-yl)ureido-methyl]benzoylamino}propionic acid

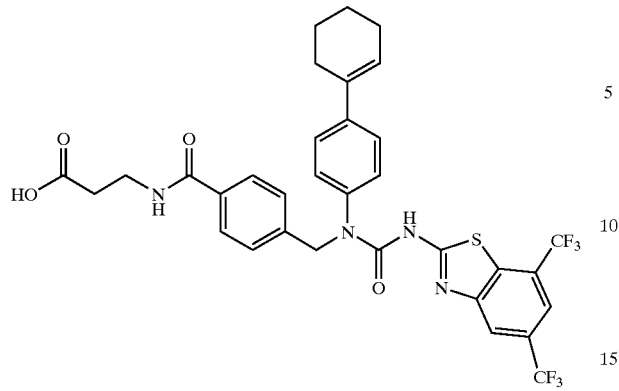

3-{4-[1-(4-cyclohex-1-enylphenyl)-3-(5,7-bis(trifluoromethyl)benzothiazol-2-yl)ureidomethyl]benzoylamino}propionic acid

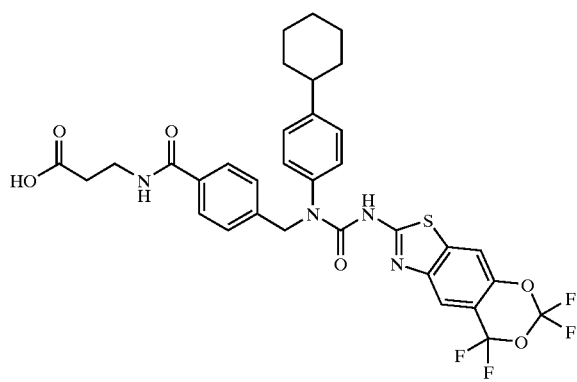

3-{4-[1-(4-cyclohexylphenyl)-3-(6,6,8,8-tetra-fluoro-6H-dioxino[5,4-f]benzothiazol-2-yl)ureidomethyl]benzoylamino}propionic acid

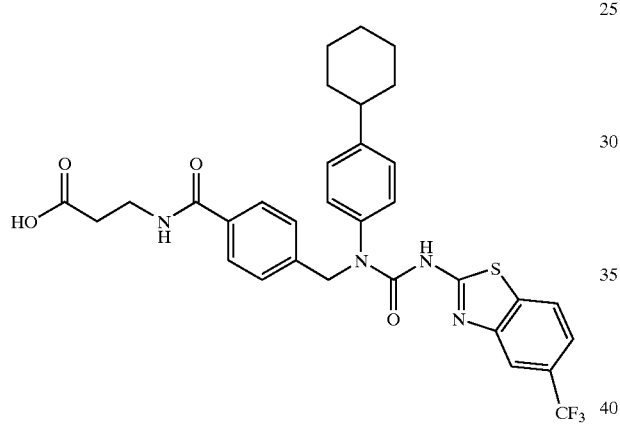

3-{4-[1-(4-cyclohexylphenyl)-3-(5-trifluoro-methylbenzothiazol-2-yl)ureidomethyl]-benzoylamino}propionic acid

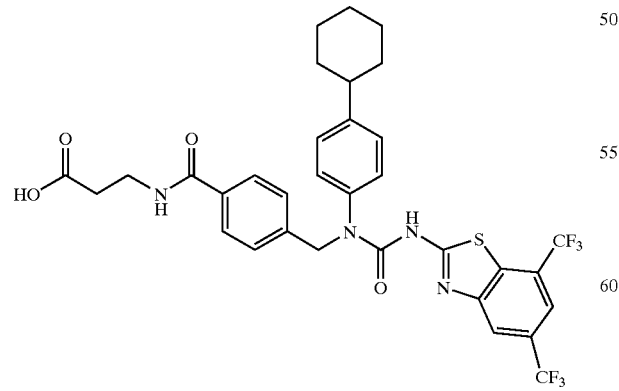

3-{4-[1-(4-cyclohex-1-enylphenyl)-3-(6,6,8,8-tetrafluoro-6H-dioxino[5,4-f]benzothiazol-2-yl)ureidomethyl]benzoyl-amino}propionic acid

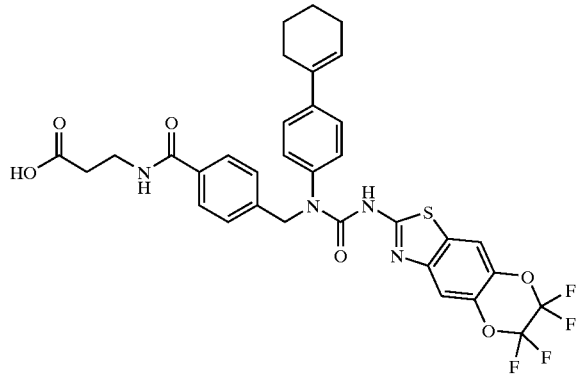

3-{4-[1-(4-cyclohexylphenyl)-3-(5,7-bis(trifluoromethyl)benzothiazol-2-yl)ureidomethyl]benzoylamino}propionic acid 3-{4-[1-(4-cyclohex-1-enylphenyl)-3-(5,6-(tetrafluoroethylenedioxo)benzothiazol-2-yl)ureidomethyl]benzoylamino}propionic acid

35
-continued

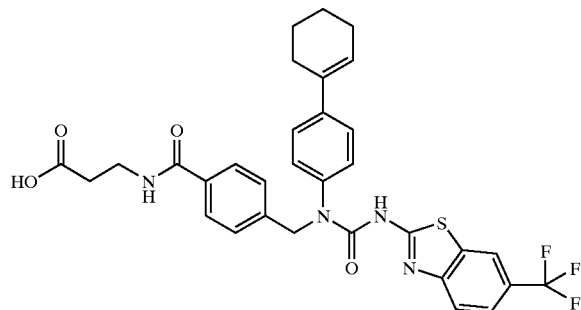

3-{4-[1-(4-cyclohex-1-enylphenyl)-3-(5-fluoro-6-trifluoromethylbenzothiazol-2-yl)ureidomethyl]benzoylamino}propionic acid

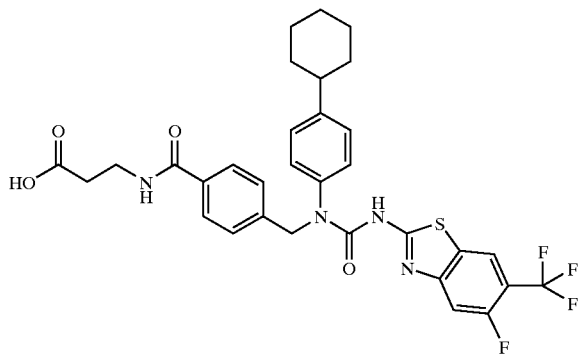

3-{4-[1-(4-cyclohexylphenyl)-3-(5-fluoro-6-tri-fluoromethylbenzothiazol-2-yl)ureidomethyl]-benzoylamino}propionic acid

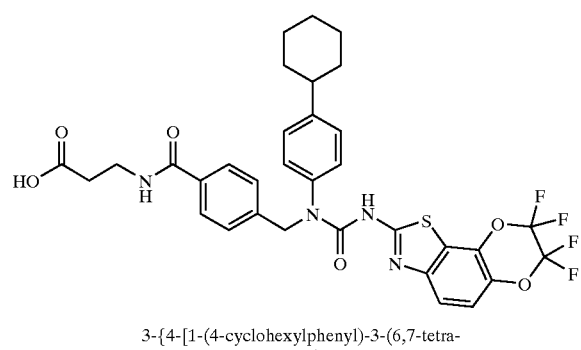

3-{4-[1-(4-cyclohexylphenyl)-3-(6,7-tetra-fluoroethylenedioxo)benzothiazol-2-yl)ureidomethyl]benzoylamino}propionic acid

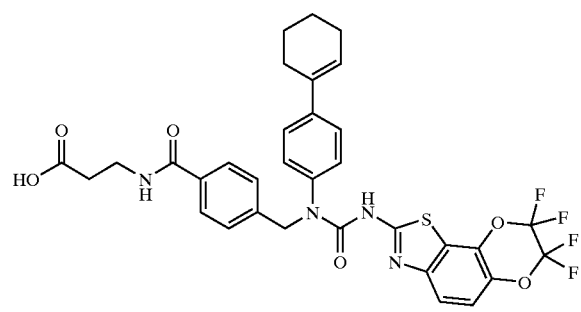

3-{4-[1-(4-cyclohex-1-enylphenyl)-3-(6,7-(tetrafluoroethylenedioxo)benzothiazol-2-yl)ureidomethyl]benzoylamino}propionic acid

36
-continued

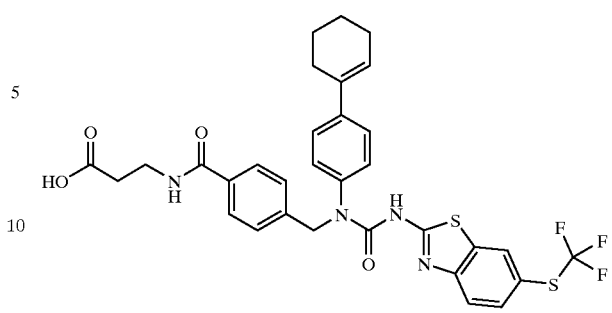

3-{4-[1-(4-cyclohex-1-enylphenyl)-3-(6-trifluoromethylthiobenzothiazol-2-yl)ureidomethyl]benzoylamino}propionic acid

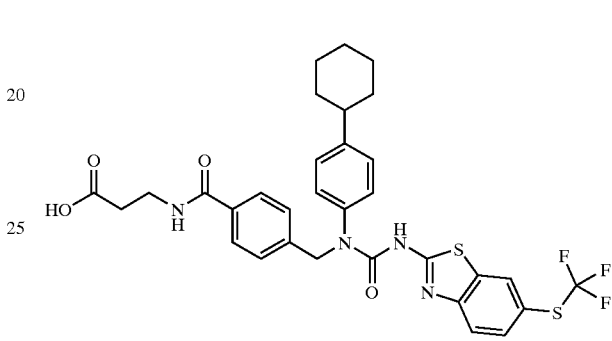

3-{4-[1-(4-cyclohexylphenyl)-3-(6-trifluoro-methylthiobenzothiazol-2-yl)ureidomethyl]-benzoylamino}propionic acid

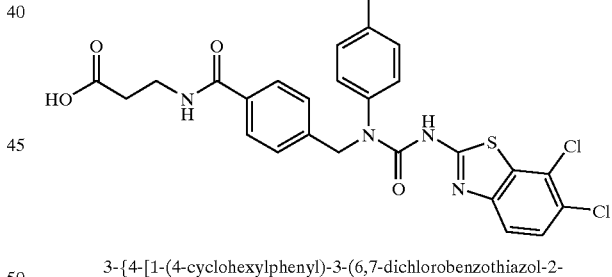

3-{4-[1-(4-cyclohexylphenyl)-3-(6,7-dichlorobenzothiazol-2-yl)ureidomethyl]-benzoylamino}propionic acid

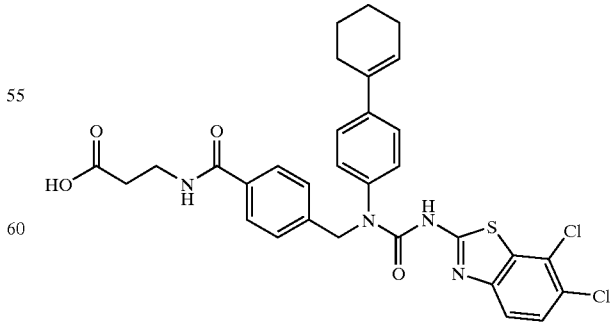

3-{4-[1-(4-cyclohex-1-enylphenyl)-3-(6,7-di-chlorobenzothiazol-2-yl)ureidomethyl]benzoyl-amino}propionic acid

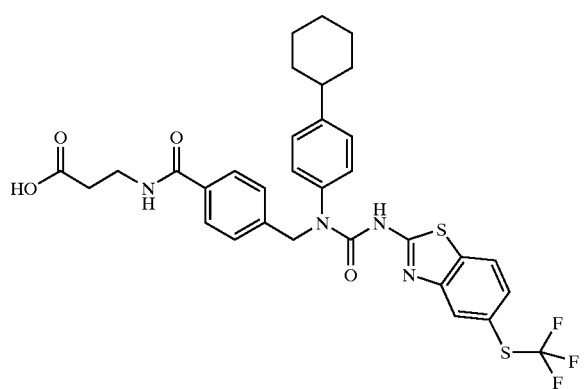

3-{4-[1-(4-cyclohexylphenyl)-3-(5-trifluoro-methylthiobenzothiazol-2-yl)ureido-methyl]benzoylamino}propionic acid

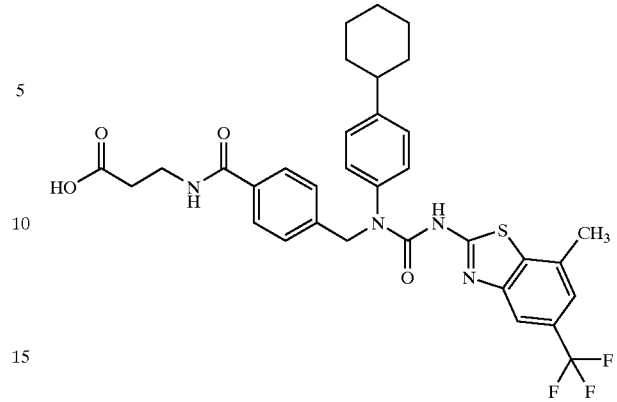

3-{4-[1-(4-cyclohexylphenyl)-3-(5-trifluoro-methyl-7-methylbenzothiazol-2-yl)ureido-methyl]benzoylamino}propionic acid

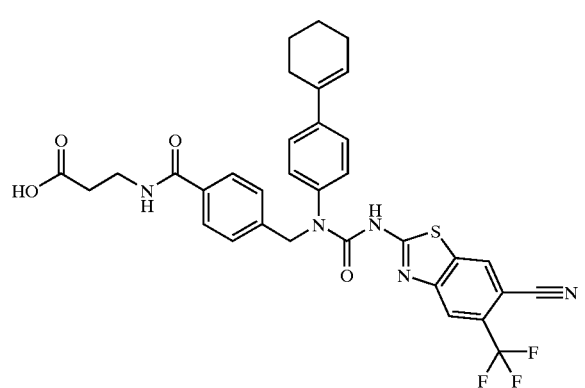

3-{4-[1-(4-cyclohex-1-enylphenyl)-3-(5-tri-fluoromethyl-6-cyanobenzothiazol-2-yl)ureido-methyl]benzoylamino}propionic acid

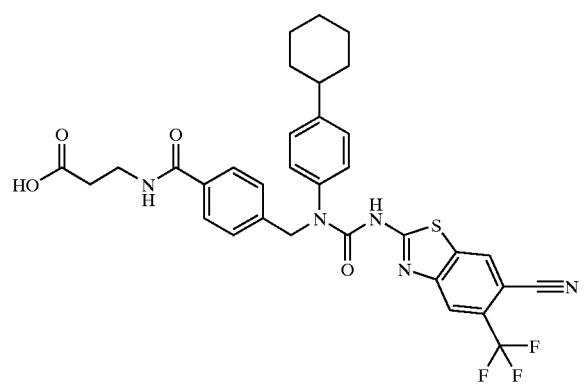

3-{4-[1-(4-cyclohex-1-enylphenyl)-3-(5-tri-fluoromethyl-7-methylbenzothiazol-2-yl)ureidomethyl]benzoylamino}propionic acid

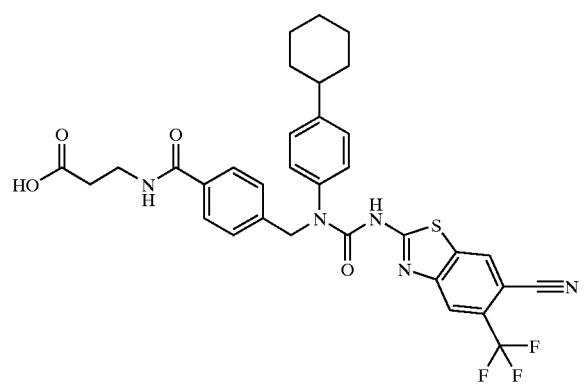

3-{4-[1-(4-cyclohexylphenyl)-3-(5-trifluoro-methyl-6-cyanobenzothiazol-2-yl)ureido-methyl]benzoylamino}propionic acid

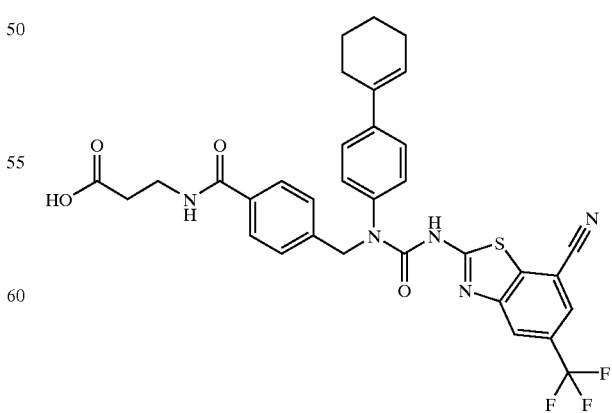

3-{4-[1-(4-cyclohex-1-enylphenyl)-3-(5-tri-fluoromethyl-7-cyanobenzothiazol-2-yl)ureido-methyl]benzoylamino}propionic acid

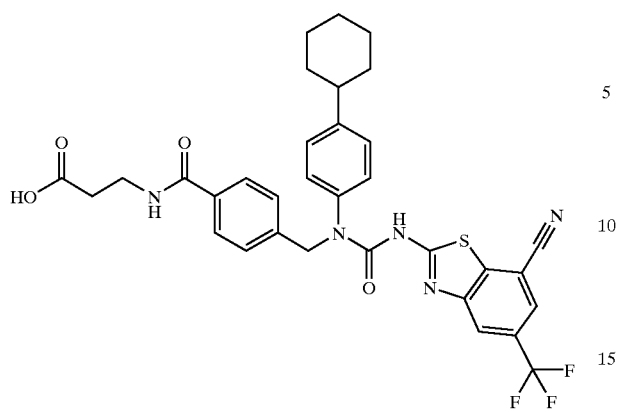

3-{4-[1-(4-cyclohexylphenyl)-3-(5-trifluoro-methyl-7-cyanobenzothiazol-2-yl)ureido-methyl]benzoylamino}propionic acid

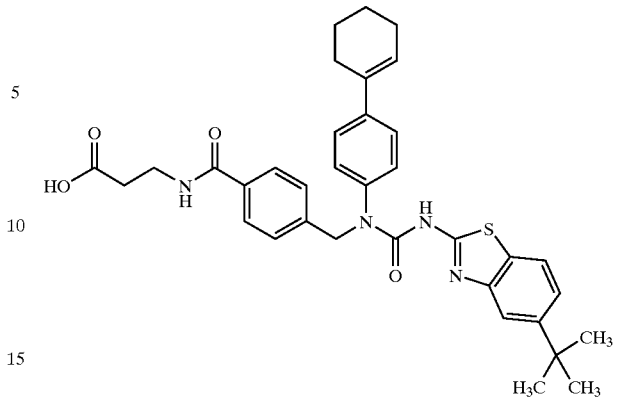

3-{4-[1-(4-cyclohex-1-enylphenyl)-3-(5-tert-butylbenzothiazol-2-yl)ureidomethyl]benzoylamino}propionic acid

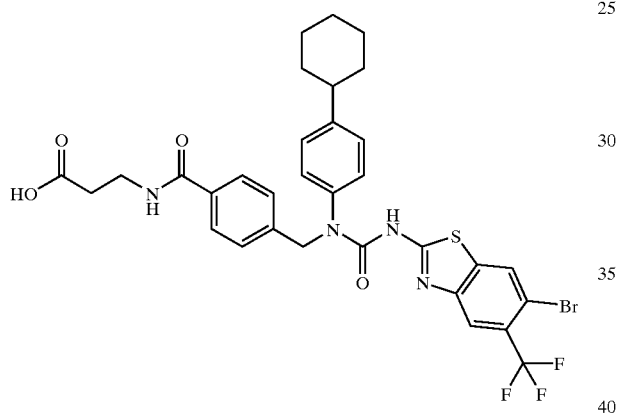

3-{4-[1-(4-cyclohexylphenyl)-3-(5-trifluoro-methyl-6-bromobenzothiazol-2-yl)ureido-methyl]benzoylamino}propionic acid

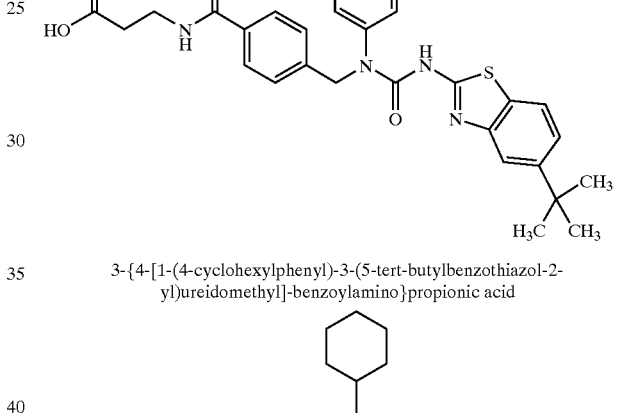

3-{4-[1-(4-cyclohexylphenyl)-3-(5-tert-butylbenzothiazol-2-yl)ureidomethyl]-benzoylamino}propionic acid

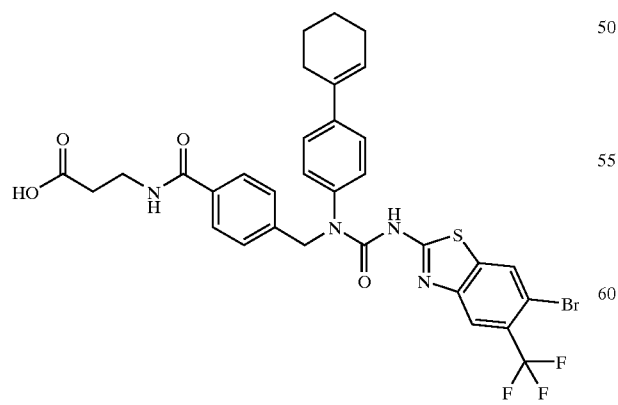

3-{4-[1-(4-cyclohex-1-enylphenyl)-3-(5-trifluoromethyl-6-bromobenzothiazol-2-yl)ureidomethyl]benzoylamino}propionic acid

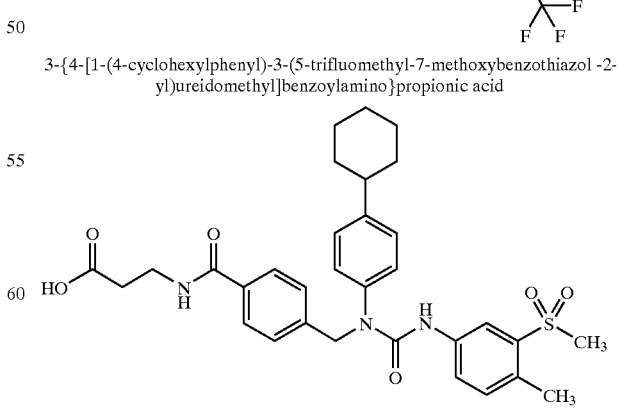

3-{4-[1-(4-cyclohexylphenyl)-3-(5-trifluomethyl-7-methoxybenzothiazol-2-yl)ureidomethyl]benzoylamino}propionic acid 3-{4-[1-(4-cyclohexylphenyl)-3-(3-methyl-sulfonyl-4-methylphenyl)ureido-methyl]benzoylamino}propionic acid

41

-continued

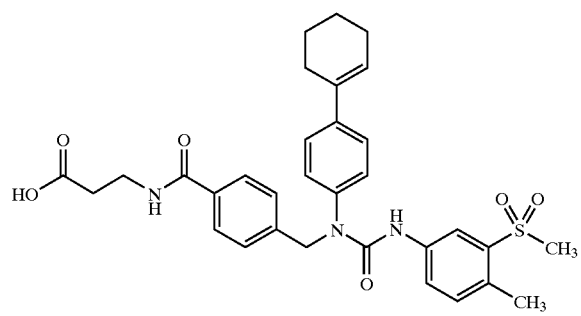

3-{4-[1-(4-cyclohex-1-enylphenyl)-3-(3-methylsulfonyl-4-methylphenyl)ureido-methyl]benzoylamino}propionic acid

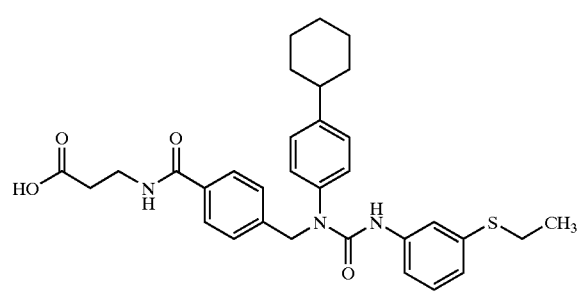

3-{4-[1-(4-cyclohexylphenyl)-3-(3-ethyl-thiophenyl)ureidomethyl]benzoylamino}-propionic acid

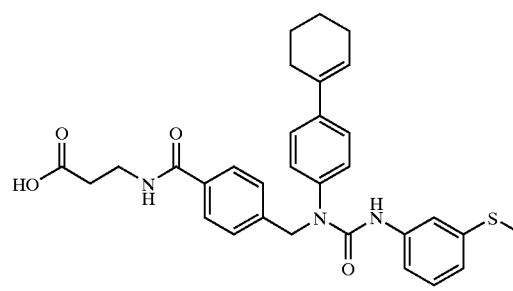

3-{4-[1-(4-cyclohex-1-enylphenyl)-3-(3-ethyl-thiophenyll)ureidomethyl]benzoylamino}-propionic acid

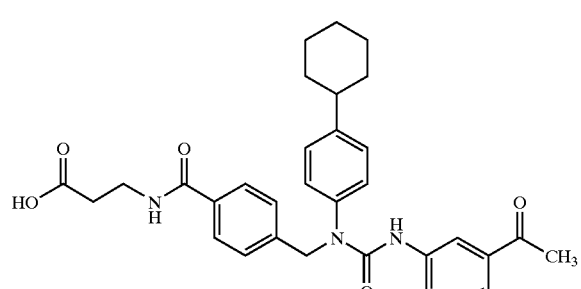

3-{4-[1-(4-cyclohexylphenyl)-3-(3-acetyl-phenyl)ureidomethyl]benzoylamino}-propionic acid

42

-continued

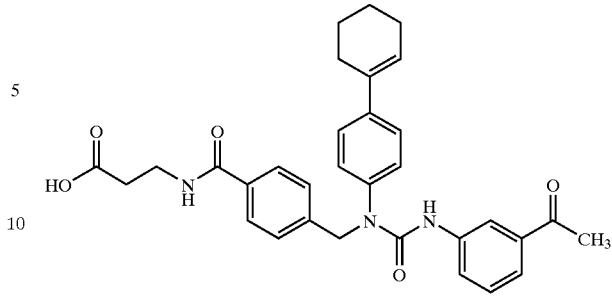

3-{4-[1-(4-cyclohex-1-enylphenyl)-3-(3-acetyl-phenyl)ureidomethyl]benzoylamino}propionic acid

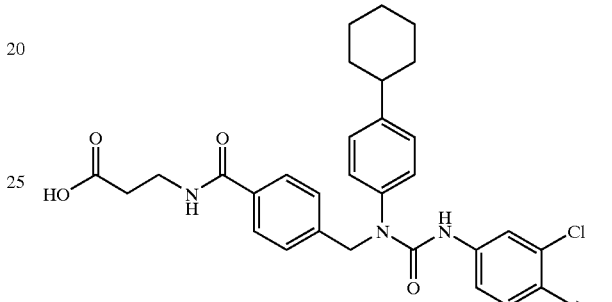

3-{4-[1-(4-cyclohexylphenyl)-3-(3-chloro-4-cyanophenyl)ureidomethyl]benzoyl-amino}propionic acid

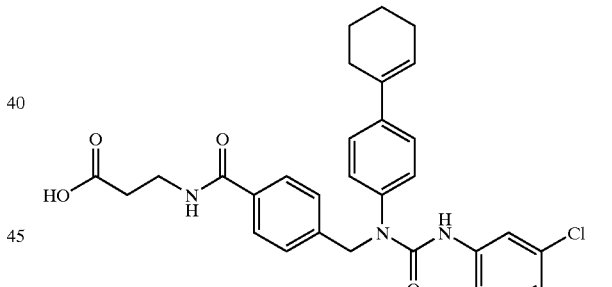

3-{4-[1-(4-cyclohex-1-enylphenyl)-3-(3-chloro-4-cyanophenyl)ureidomethyl]benzoylamino}-propionic acid

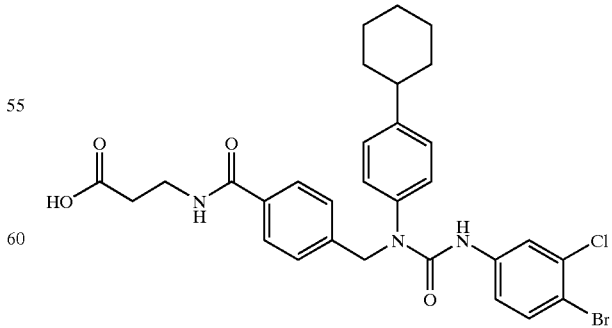

3-{4-[1-(4-cyclohexylphenyl)-3-(3-chloro-4-bromophenyl)ureidomethyl]benzoyl-amino}propionic acid

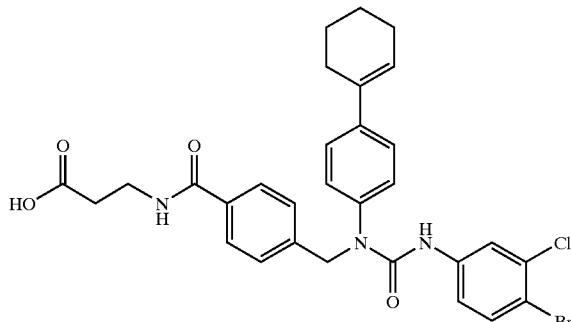

3-{4-[1-(4-cyclohex-1-enylphenyl)-3-(3-chloro-4-bromophenyl)ureidomethyl]benzoylamino}-propionic acid

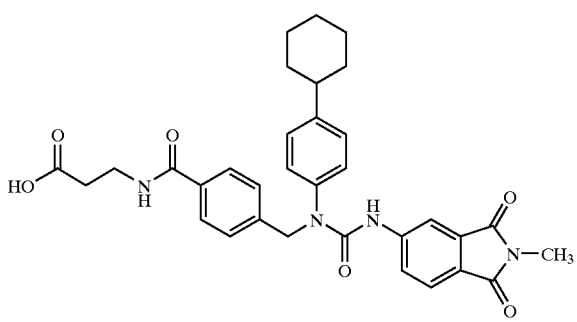

3-{4-[1-(4-cyclohexylphenyl)-3-(2-methyl-1,3-dioxo-2,3-dihydro-1H-isoindol-5-yl)ureidomethyl]benzoylamino}propionic acid

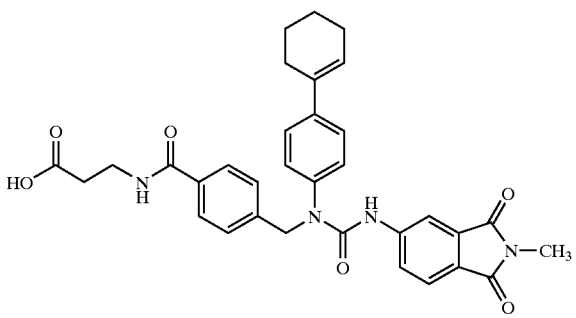

3-{4-[1-(4-cyclohex-1-enylphenyl)-3-(2-methyl-1,3-dioxo-2,3-dihydro-1H-isoindol-5-yl)ureidomethyl]benzoylamino}propionic acid

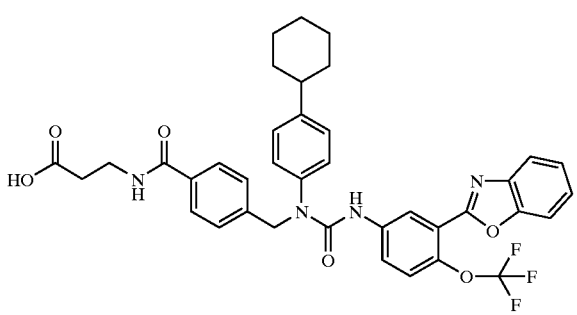

3-{4-[1-(4-cyclohexylphenyl)-3-(3-benzo-oxazol-2-yl-4-trifluoromethoxyphenyl)ureidomethyl]benzoylamino}propionic acid

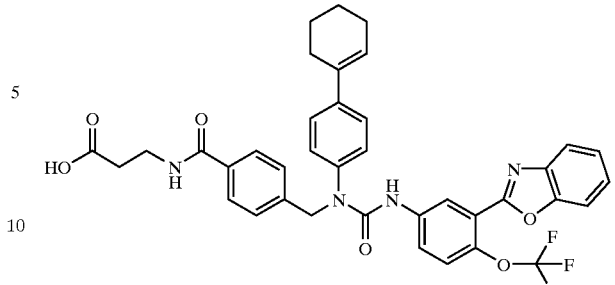

3-{4-[1-(4-cyclohex-1-enylphenyl)-3-(3-benzo-oxazol-2-yl-4-trifluoromethoxyphenyl)ureido-methyl]benzoylamino}propionic acid

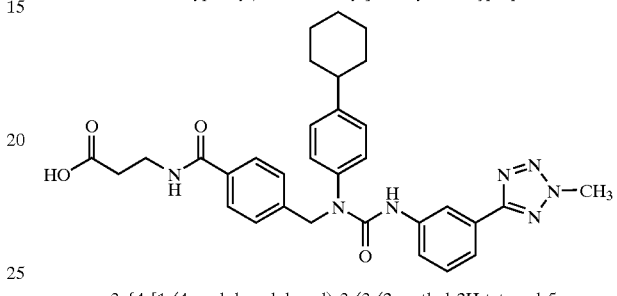

3-{4-[1-(4-cyclohexylphenyl)-3-(3-(2-methyl-2H-tetrazol-5-yl)phenyl)ureido-methyl]benzoylamino}propionic acid

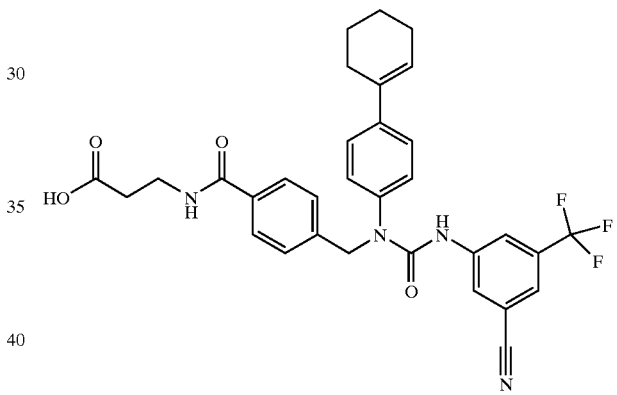

3-{4-[3-(3-cyano-5-trifluoromethylphenyl)-1-(4-cyclohex-1-enylphenyl)ureidomethyl]benzoyl-amino}propionic acid as well as any optical or geometric isomer or tautomeric form thereof including mixtures of these or a pharmaceutically acceptable salt thereof.

In a preferred embodiment of the invention the compound is selected from

- 3-{4-[1-(4-cyclohexylphenyl)-3-(3-trifluoromethoxyphenyl)ureidomethyl]benzoylamino}propionic acid
- 3-{4-[1-(4-cyclohex-1-enylphenyl)-3-(3-trifluoromethoxyphenyl)ureidomethyl]benzoylamino}propionic acid
- 3-{4-[1-(4-cyclohexylphenyl)-3-(3-trifluoromethylphenyl)ureidomethyl]benzoylamino}propionic acid 3-{4-[1-(4-cyclohexylphenyl)-3-(3-bromophenyl)
ureidomethyl]benzoylamino}propionic acid 3-{4-[1-(4-cyclohex-1-enylphenyl)-3-(3-bromophenyl)
ureidomethyl]benzoylamino}propionic acid 3-{4-[1-(4-cyclohexylphenyl)-3-(3-trifluoromethyl-5-fluorophenyl)ureidomethyl]benzoylamino}propionic acid 3-{4-[1-(4-cyclohexylphenyl)-3-(3-trifluoromethyl-5-cyanophenyl)ureidomethyl]benzoylamino}propionic acid 3-{4-[1-(4-cyclohex-1-enylphenyl)-3-(3-methylsulfonyl-4-trifluoromethoxyphenyl)ureidomethyl]benzoylamino}propionic acid 3-{4-[1-(4-cyclohexylphenyl)-3-(3-hydroxymethyl-4-trifluoromethoxyphenyl)ureidomethyl]benzoylamino}propionic acid 3-{4-[1-(4-cyclohex-1-enylphenyl)-3-(3-hydroxymethyl-4-trifluoromethoxyphenyl)ureidomethyl]benzoylamino}propionic acid 3-{4-[1-(4-cyclohexylphenyl)-3-(3-methylthiophenyl)
ureidomethyl]benzoylamino}propionic acid 3-{4-[1-(4-cyclohex-1-enylphenyl)-3-(3-methylthiophenyl)
ureidomethyl]benzoylamino}propionic acid 3-{4-[3-[1(S)-(4-chlorophenyl)ethyl]1-(4-cyclohexylphenyl)ureidomethyl]benzoylamino}propionic acid 3-{4-[3-biphenyl-2-ylmethyl-1-(4-cyclohexylphenyl)
ureidomethyl]benzoylamino}propionic acid 3-{4-[1-(4-cyclohexylphenyl)-3-(2,2,4,4-tetrafluorobenzo[1,3]dioxin-6-yl)ureidomethyl]benzoyl-amino}propionic acid 3-{4-[1-(4-cyclohex-1-enylphenyl)-3-(2,2,4,4-tetrafluorobenzo[1,3]dioxin-6-yl)ureidomethyl]benzoylamino}propionic acid 3-{4-[1-(4-cyclohexylphenyl)-3-(3,3,4,4-tetrafluorobenzo[1,4]dioxin-6-yl)ureidomethyl]benzoyl-amino}propionic acid 3-{4-[1-(4-cyclohex-1-enylphenyl)-3-(3,3,4,4-tetrafluorobenzo[1,4]dioxin-6-yl)ureidomethyl]benzoylamino}propionic acid 3-{4-[1-(4-cyclohexylphenyl)-3-(6-trifluoromethoxybenzothiazol-2-yl)ureidomethyl]benzoyl-amino}propionic acid 3-{4-[1-(4-cyclohex-1-enylphenyl)-3-(6-trifluoromethoxybenzothiazol-2-yl)ureidomethyl]benzoylamino}propionic acid 3-{4-[3-(3-cyano-5-trifluoromethylphenyl)-1-(4-cyclohex-1-enylphenyl)ureidomethyl]benzoyl-amino}propionic acid as well as any optical or geometric isomer or tautomeric form thereof including mixtures of these or a pharmaceutically acceptable salt thereof.

The compounds of the present invention may have one or more asymmetric centers and it is intended that any optical isomers, as separated, pure or partially purified optical isomers or racemic mixtures thereof are included within the scope of the invention.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methyl-, dimethyl-, trimethyl-, ethyl-, hydroxyethyl-, diethyl-, butyl-, tetramethylammonium salts and the like.

Also intended as pharmaceutically acceptable acid addition salts are the hydrates, which the present compounds, are able to form.

Furthermore, the pharmaceutically acceptable salts comprise basic amino acid salts such as lysine, arginine and ornithine.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of present compounds, which are readily convertible in vivo into the required compound. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds according to the present invention act to antagonize the action of glucagon and are accordingly useful for the treatment and/or prevention of disorders and diseases in which such an antagonism is beneficial.

Accordingly, the present compounds may be applicable for the treatment and/or prevention of hyperglycemia, IGT (impaired glucose tolerance), insulin resistance syndromes, syndrome X, Type 1 diabetes, Type 2 diabetes, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc.

Furthermore, they may be applicable as diagnostic agents for identifying patients having a defect in the glucagon receptor, as a therapy to increase gastric acid secretions and to reverse intestinal hypomobility due to glucagon administration.

They may also be useful as tool or reference molecules in labelled form in binding assays to identify new glucagon antagonists.

Accordingly, in a further aspect the invention relates to a compound according to the invention for use as a medicament.

The invention also relates to pharmaceutical compositions comprising, as an active ingredient, at least one compound according to the invention together with one or more pharmaceutically acceptable carriers or excipients.

The pharmaceutical composition is preferably in unit dosage form, comprising from about 0.05 mg to about 1000 mg, preferably from about 0.1 mg to about 500 mg and especially preferred from about 0.5 mg to about 200 mg of the compound according to the invention.

Furthermore, the invention relates to the use of a compound according to the invention for the preparation of a pharmaceutical composition for the treatment and/or prevention of a disorder or disease, wherein a glucagon antagonistic action is beneficial.

The invention also relates to a method for the treatment and/or prevention of disorders or diseases, wherein a glucagon antagonistic action is beneficial the method comprising administering to a
  in need thereof an effective amount of a compound according to the invention.

In a preferred embodiment of the invention the present compounds are used for the preparation of a medicament for the treatment and/or prevention of any glucagon-mediated conditions and diseases.

In a preferred embodiment of the invention the present compounds are used for the preparation of a medicament for the treatment and/or prevention of hyperglycemia.

In yet a preferred embodiment of the invention the present compounds are used for the preparation of a medicament for lowering blood glucose in a mammal. The present compounds are effective in lowering the blood glucose, both in the fasting and the postprandial stage.

In another preferred embodiment of the invention the present compounds are used for the preparation of a pharmaceutical composition for the treatment and/or prevention of IGT.

In still another preferred embodiment of the invention the present compounds are used for the preparation of a pharmaceutical composition for the treatment and/or prevention of Type 2 diabetes.

In yet another preferred embodiment of the invention the present compounds are used for the preparation of a pharmaceutical composition for the delaying or prevention of the progression from IGT to Type 2 diabetes.

In yet another preferred embodiment of the invention the present compounds are used for the preparation of a pharmaceutical composition for the delaying or prevention of the progression from non-insulin requiring Type 2 diabetes to insulin requiring Type 2 diabetes.

In a further preferred embodiment of the invention the present compounds are used for the preparation of a pharmaceutical composition for the treatment and/or prevention of Type 1 diabetes. Such treatment and/or prevention is normally accompanied by insulin therapy.

In a further preferred embodiment of the invention the present compounds are used for the preparation of a pharmaceutical composition for the treatment and/or prevention of obesity.

In yet a further preferred embodiment of the invention the present compounds are used for the preparation of a pharmaceutical composition for the treatment and/or prevention of disorders of the lipid metabolism.

In still a further preferred embodiment of the invention the present compounds are used for the preparation of a pharmaceutical composition for the treatment and/or prevention of an appetite regulation or energy expenditure disorder.

In a further aspect of the invention, treatment of a patient with the present compounds is combined with diet and/or exercise.

In still a further aspect of the invention the present compounds are administered in combination with one or more further active substances in any suitable ratios. Such further active substances may eg be selected from antiobesity agents, antidiabetics, antihypertensive agents, agents for the treatment of complications resulting from or associated with diabetes and agents for the treatment of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

Suitable antidiabetic agents include insulin, insulin analogues and derivatives such as those disclosed in EP 792 290 (Novo Nordisk A/S), eg $N^{\epsilon B29}$-tetradecanoyl des (B30) human insulin, EP 214 826 and EP 705 275 (Novo Nordisk A/S), eg Asp$^{B28}$ human insulin, U.S. Pat. No. 5,504,188 (Eli Lilly), eg Lys$^{B28}$ Pro$^{B29}$ human insulin, EP 368 187 (Aventis), eg Lantus, which are all incorporated herein by reference, GLP-1 and GLP-1 derivatives such as those disclosed in WO 98/08871 (Novo Nordisk A/S), which is incorporated herein by reference, as well as orally active hypoglycaemic agents.

The orally active hypoglycaemic agents preferably comprise imidazolines, sulphonylureas, biguanides, meglitinides, oxadiazolidinediones, thiazolidinediones, insulin sensitizers, insulin secretagogues, such as glimepride, α-glucosidase inhibitors, agents acting on the ATP-dependent potassium channel of the β-cells eg potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00142026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment, the present compounds are administered in combination with insulin or an insulin analogue or derivative, such as $N^{\epsilon B29}$-tetradecanoyl des (B30) human insulin, Asp$^{B28}$ human insulin, Lys$^{B28}$ Pro$^{B29}$ human insulin, Lantus, or a mix-preparation comprising one or more of these.

In a further embodiment of the invention the present compounds are administered in combination with a sulphonylurea eg tolbutamide, chlorpropamide, tolazamide, glibenclamide, glipizide, glimepiride, glicazide or glyburide.

In another embodiment of the invention the present compounds are administered in combination with a biguanide eg metformin.

In yet another embodiment of the invention the present compounds are administered in combination with a meglitinide eg repaglinide or nateglinide.

In still another embodiment of the invention the present compounds are administered in combination with a thiazolidinedione insulin sensitizer eg troglitazone, ciglitazone, pioglitazone, rosiglitazone, isaglitazone, darglitazone, englitazone, CS-011/Cl-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor eg voglibose, emiglitate, miglitol or acarbose.

In another embodiment of the invention the present compounds are administered in combination with an agent acting on the ATP-dependent potassium channel of the β-cells eg tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent eg cholestyramine, colestipol, clofibrate, gemfibrozil, lovastatin, pravastatin, simvastatin, probucol or dextrothyroxine.

In another aspect of the invention, the present compounds are administered in combination with more than one of the above-mentioned compounds eg in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa, 1995.

It should be understood that any suitable combination of the compounds according to the invention with diet and/or exercise, one or more of the above-mentioned compounds and optionally one or more other active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound according to the invention contains a free base such salts are prepared in a conventional manner by treating a solution or suspension of a free base of the compound in question with a chemical equivalent of a pharmaceutically acceptable acid. Representative examples are mentioned above. Physiologically acceptable salts of a compound with a hydroxy group include the anion of said compound in combination with a suitable cation such as sodium or ammonium ion.

For parenteral administration, solutions of the novel compounds according to the invention in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the present compounds and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
| --- | --- |
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the invention may comprise a compound according to the invention in combination with further pharmacologically active substances such as those described in the foregoing.

EXAMPLES

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of the glucagon antagonists of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

Some of the NMR data shown in the following examples are only selected data.

In the examples and pharmacological methods the following terms are intended to have the following meanings:

| | |
|---|---|
| DMF: | N,N-dimethylformamide |
| DMSO: | dimethyl sulphoxide |
| M.p.: | melting point |
| TFA: | trifluoroacetic acid |
| THF: | Tetrahydrofuran |
| EDAC: | 1-ethyl-3-(3-dimethylaminopropyl)carbodiimide hydrochloride |
| HOBt | 1-hydroxybenzotriazole |
| HOAt | 3-hydroxy-3H-[1,2,3]triazolo[4,5-b]pyridine |
| EGTA | ethylene glycol bis($\beta$-aminoethyl ether)N,N,N',N'-tetracetic acid |
| IBMX | isobutylmethylxanthine |

HPLC-MS (Method A)

The following instrumentation was used:

Hewlett Packard series 1100 G1312A Bin Pump

Hewlett Packard series 1100 Column compartment

Hewlett Packard series 1100 G13 15A DAD diode array detector

Hewlett Packard series 1100 MSD

The instrument was controlled by HP Chemstation software.

The HPLC pump was connected to two eluent reservoirs containing:

A 0.01% TFA in water

B 0.01% TFA in acetonitrile

The analysis was performed at 40° C. by injecting an appropriate volume of the sample (preferably 1 $\mu$l) onto the column, which was eluted with a gradient of acetonitrile.

The HPLC conditions, detector settings and mass spectrometer settings used are given in the following table.

| | |
|---|---|
| Column | Waters Xterra MS C-18 × 3 mm id |
| Gradient | 10%–100% acetonitrile lineary during 7.5 min at 1.0 ml/min |
| Detection | UV: 210 nm (analog output from DAD) |
| MS | Ionisation mode: API-ES |
| | Scan 100–1000 amu step 0.1 amu |

HPLC-MS (Method B)

The following instrumentation was used:

Sciex API 100 Single quadropole mass spectrometer

Perkin Elmer Series 200 Quard pump

Perkin Elmer Series 200 autosampler

Applied Biosystems 785A UV detector

Sedex 55 evaporative light scattering detector

A Valco column switch with a Valco actuator controlled by timed events from the pump.

The Sciex Sample control software running on a Macintosh PowerPC 7200 computer was used for the instrument control and data acquisition.

The HPLC pump was connected to four eluent reservoirs containing:

| | |
|---|---|
| A: | Acetonitrile |
| B: | Water |
| C: | 0.5% TFA in water |
| D: | 0.02 M ammonium acetate |

The requirements for the samples are that they contain approximately 500 $\mu$g/ml of the compound to be analysed in an acceptable solvent such as methanol, ethanol, acetonitrile, THF, water and mixtures thereof. (High concentrations of strongly eluting solvents will interfere with the chromatography at low acetonitrile concentrations.)

The analysis was performed at room temperature by injecting 20 $\mu$l of the sample solution on the column, which was eluted with a gradient of acetonitrile in either 0.05% TFA or 0.002 M ammonium acetate. Depending on the analysis method varying elution conditions were used.

The eluate from the column was passed through a flow splitting T-connector, which passed approximately 20 $\mu$l/min through approx. 1 m 75$\mu$ fused silica capillary to the API interface of API 100 spectrometer.

The remaining 1.48 ml/min was passed through the UV detector and to the ELS detector.

During the LC-analysis the detection data were acquired concurrently from the mass spectrometer, the UV detector and the ELS detector.

The LC conditions, detector settings and mass spectrometer settings used for the different methods are given in the following table.

| | | |
|---|---|---|
| Column | YMC ODS-A 120Ås - 5$\mu$ 3 mm × 50 mm id | |
| Gradient | 5%–90% acetonitrile in 0.05% TFA linearly during 7.5 min at 1.5 ml/min | |
| Detection | UV: 214 nm | ELS: 40° C. |
| MS | Experiment: Start: 100 amu Stop: 800 amu Step: 0.2 amu | |
| | Dwell: 0.571 msec | |
| | Method: Scan 284 times = 9.5 min | |

General Procedure (A)

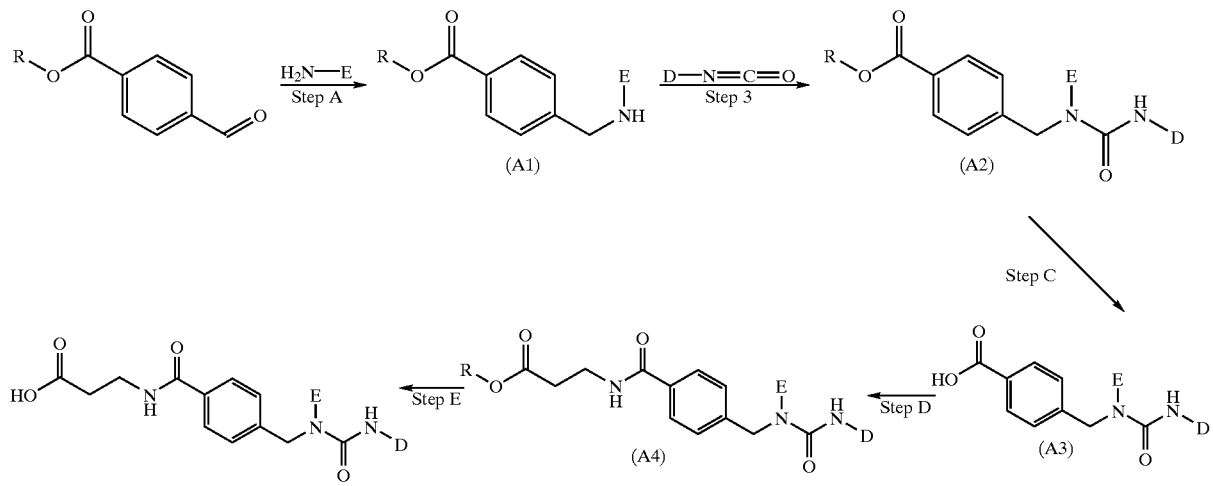

wherein E is 4-cyclohexylphenyl, 4-cyclohex1-enylphenyl or 4-cyclohexylcyclohexyl, D is as defined for the present compounds and R is $C_{1-6}$-alkyl.

The term "$C_{1-6}$-alkyl" as used herein represents a saturated, branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

Intermediates to be Used in Step A

4-Cyclohex-1-enylaniline

This compound was prepared similarly as described in J. v. Braun et al., J. Liebigs Ann. Chem., 472 (1929), 1–89, from refluxing aniline (2 equivalents), cyclohexanone (1 equivalent) in ethanol and 37% hydrochloric acid for 4–5 days, followed by addition of ethyl acetate, water, and sodium hydroxide, neutralisation with 85% phosphoric acid, phase separation, and distillation of the organic phase. The residue was added a catalytic amount of sulfuric acid and distilled (180° C., 5–7 mbar). The distillate was redistilled (120° C., 3 mbar) to afford (in the residue) a 49% yield of the desired 4-cyclohex-1-enylaniline.

$^1$H NMR (DMSO-$d_6$): δ1.50–1.60 (m, 2H), 1.60–1.70 (m, 2H), 2.10–2.15 (m, 2H), 2.20–2.30 (brd s, 2H), 5.00 (s, 2H), 5.90 (t, 1H), 6.50 (d, 2H), 7.10 (d, 2H).

This compound can also be prepared as described in Justus Liebigs Ann. Chem., 472, 1–89, 1929.

4-Cyclohexylaniline is commercially available (e.g. from Lancaster or Avocado)

4-Cyclohexylcyclohexylamine is described in the literature: H. Booth et al., J. Chem. Soc. (B), 1971, 1047–1050.

Step A

To a solution of E-NH$_2$ (eg 4-cyclohexenylaniline, prepared as described above) (0.023 mol) and methyl 4-formylbenzoate (3.77 g, 0.023 mol) in dichloromethane (50 ml) and methanol (15 ml) was added a catalytic amount of acetic acid. After stirring the solution for 3 hours, Na(OAc)$_3$BH (24 g, 0.115 mol) was added. The reaction was allowed to stir at room temperature for 16 hours. The reaction mixture was diluted with ethyl acetate and washed with aqueous sodium bicarbonate (3×), brine (2×), dried over magnesium sulphate, filtered, and concentrated to give a solid. The crude product was purified by column chromatography eluting with mixtures of ethyl acetate and heptane to give 4-[(4-cyclohex-1-enylphenylamino)-methyl]benzoic acid methyl ester (Al) (5 g, 0.015 mol).

$^1$H NMR (DMSO-$d_6$): δ1.56 (m, 2H), 1.67 (m, 2H), 2.11 (m, 2H), 2.25 (m, 2H), 3.81 (s, 3H), 4.34 (d, 2H), 5.89 (t, 1H), 6.34 (t, 1H), 6.49 (d, 2H), 7.10 (d, 2H), 7.47 (d, 2H), 7.90 (d, 2H).

Step B

The above 4-[(4-cyclohex-1-enylphenylamino)methyl] benzoic acid methyl ester (5 g, 0.015 mol) was dissolved in anhydrous dichloromethane and diisopropylethylamine (5.8 g, 0.045 mol) was added. To this solution was added an isocyanate (D—N=C=O) (0.018 mol). After stirring the reaction mixture for 3 hours, the solution was diluted with ethyl acetate and washed with 1N hydrochloric acid (2×), water, brine, dried over magnesium sulphate, filtered and concentrated in vacuo. The residue was purified by column chromatography eluting with mixtures of ethyl acetate and heptane to give (A2).

Step C

To a solution of (A2) (2 mmol) in THF (30 ml) and methanol (10 ml) was added an excess of 2 M lithium hydroxide (10 ml). After stirring the reaction mixture for 3 hours, the solution was concentrated. The residue was taken up in ethyl acetate and washed with 1 N hydrochloric acid (2×), water (2×), brine, and dried over magnesium sulphate. Evaporation of the solvent gave (A3).

Step D

To a solution of (A3) (0.81 mmol) in DMF (4 ml) were added 3-[(dimethyliminium)-(dimethylamino)methyl]-1,2,3-benzotriazol-1-ium-1-olate hexafluorophosphate (HBTU) (0.37 g, 0.90 mmol), diisopropylethylamine (0.30 g, 2.4 mmol), and ethyl 3-aminopropanoate hydrochloride (0.30 g, 2.4 mmol). After stirring the solution for 16 hours, the reaction was diluted with ethyl acetate and washed with 1N hydrochloric acid (3×), brine (3×), dried over magnesium sulphate, filtered, and concentrated. The residue was purified by column chromatography and eluted with mixtures of ethyl acetate and heptane to afford (A4).

Step E (A4) was dissolved in THF (6 ml) and methanol (3 ml). A solution of 2 M lithium hydroxide (3 ml) was then added and the reaction was stirred at room temperature for 30 min. The solvents were evaporated under reduced pressure. The residue was taken up in ethyl acetate and washed with 1 N hydrochloric acid (2×), brine (2×), dried over magnesium sulphate, filtered, and concentrated in vacuo to afford the title compound.

General Procedure (B)

The compounds of the invention may also be prepared according to the following general procedure (B):

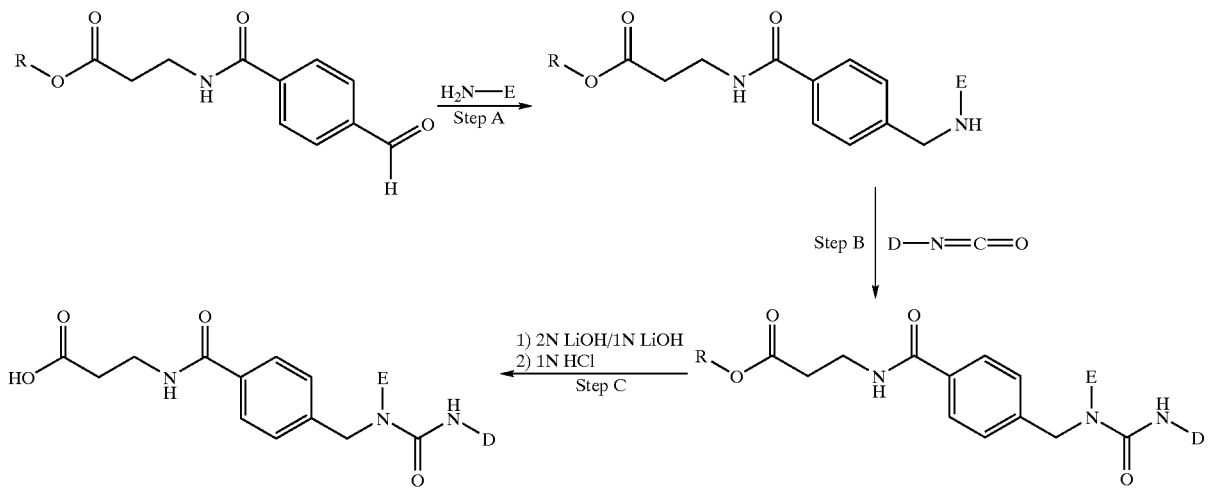

wherein E is 4-cyclohexylphenyl, 4-cyclohex1-enylphenyl or 4-cyclohexylcyclohexyl, D is as defined for the present compounds and R is $C_{1-6}$-alkyl.

Preparation of methyl 3-[(4-formylbenzoyl)amino] propionate as Starting Material To a solution of the 4-formylbenzoic acid in a suitable solvent such as dichloromethane, DMF or THF was added diisopropylethylamine (3 eq) and 3-[(dimethyliminium)-(dimethylamino)methyl]-1,2,3-benzotriazol-1-ium-1-olate hexafluorophosphate (HBTU) (1.1 eq). The reaction was allowed to stir for 30 min before ethyl or methyl-3-aminopropionate hydrochloride (1.1 eq) was added. The solution was stirred at room temperature for 4 hours. The solvents were evaporated under reduced pressure. The residue was taken up in ethyl acetate and 1N hydrochloric acid. The organic layer was separated and washed with water (2×), aqueous sodium hydrogen carbonate (3×), brine (2×), dried over magnesium sulphate and concentrated to give the desired product.

$^1$H NMR (DMSO-$d_6$): δ2.62 (t, 2H), 3.52 (q, 2H), 3.60 (s, 3H), 8.00 (m, 4H), 8.98 (t, 1H), 10.06 (s, 1H).

The procedure is illustrated in examples 2 to 4 below.

General Procedure (C)

The compounds of the invention may also be prepared on solid support according to the following general procedure (C):

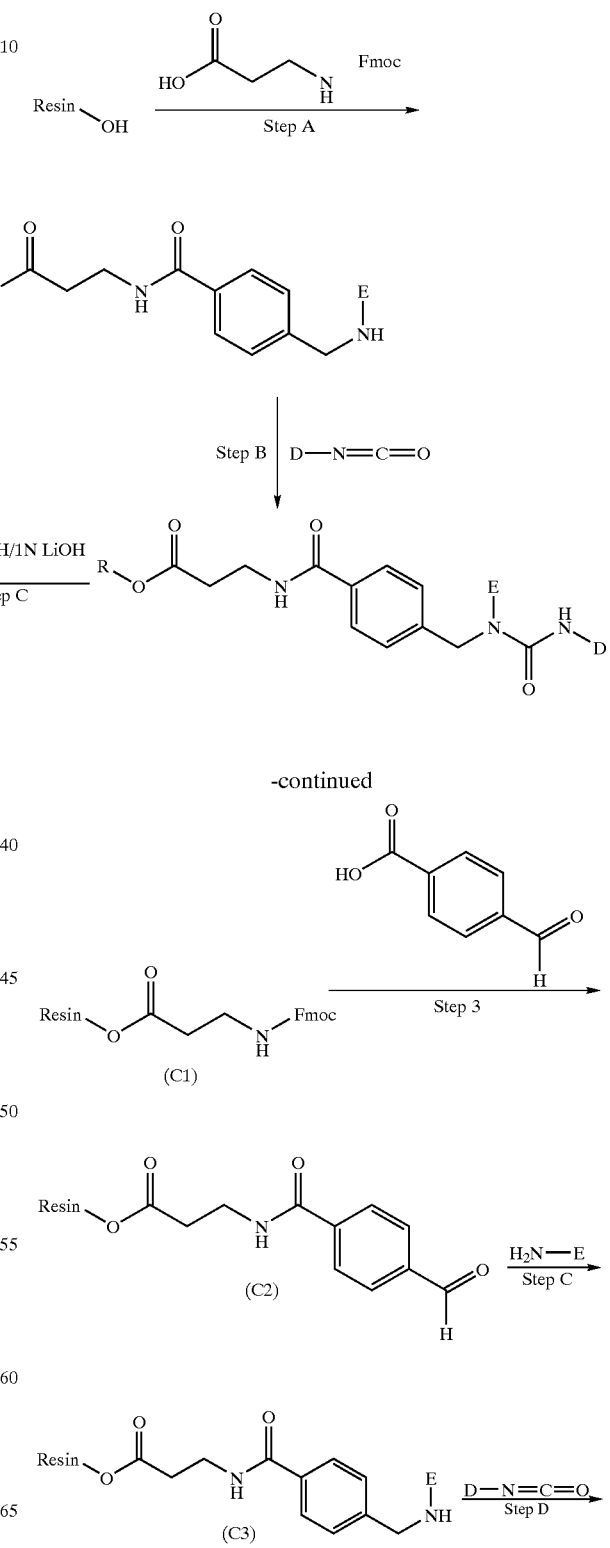

-continued

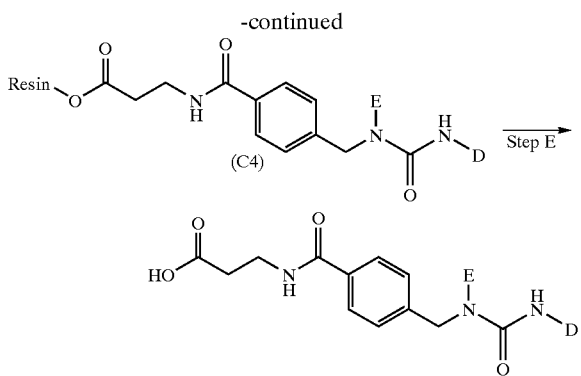

wherein E is 4-cyclohexylphenyl, 4-cyclohex-1-enylphenyl or 4-cyclohexylcyclohexyl, D is as defined for the present compounds and Resin denotes a polystyrene resin with a linker such as the Wang linker:

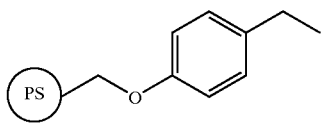

wherein PS denotes polystyrene.

Step A

The reaction is known (Wang S. J., J. Am. Chem. Soc. 95, 1328, 1973) and is generally performed by stirring polystyrene resin loaded with a linker such as the Wang linker with a 4–10 molar excess of Fmoc-protected amino acid activated with a 2–5 molar excess of diisopropylcarbodiimide or dicyclohexylcarbodiimide in the presence of a catalyst such as N,N-4-di-methylaminopyridine. The esterification is carried out in a solvent such as THF, dioxane, toluene, dichloromethane, DMF, N-methylpyrrolidinone or a mixture of two or more of these. The reactions are performed between 0° C. to 80° C., preferably between 20° C. to 40° C. When the esterification is complete excess of reagents is removed by filtration. The resin is successively washed with the solvent used in the reaction, followed by washings with methanol. The resin bound product can be further dried and analyzed.

Step B

The Fmoc protecting group is removed using a solution of 20% piperidine in DMF which is added to the resin and vortexed for 0.5 hours. After draining the resin is washed with DMF containing HOBt (50 mg/ml) and DMF.

The acylation (The combinatorial index, Ed. Bunin, B. A. 1998, Academic Press, p. 78) is performed by adding an excess of acid (III) in a solvent such as DMF, N-methylpyrrolidinone, THF, dichloromethane, 1,2-dichloroethane, acetonitrile, DMSO or a mixture of two or more of these, optionally in the presence of a base such as N-methylmorpholine, triethylamine, diisopropylethylamine, dicyclohexylmethylamine or another tertiary amine, followed by a coupling reagent such as dicyclohexylcarbodiimide, diisopropylcarbodiimide, 1,1'-carbonyldiimidazole, 2-(1H-9-azabenzotriazole-1-yl)-1,1,3,3-tetramethyluronium hexafluorophosphate or bromo-tris-pyrrolidinophosphonium hexafluorophosphate in a solvent such as DMF, N-methylpyrrolidinone, THF, dichloromethane, 1,2-dichloroethane, acetonitrile, DMSO or a mixture of two or more of these, optionally in the presence of a side reaction inhibitor such as 3-hydroxy-4-oxo-3,4-dihydro-1,2,3-benzotriazine, N-hydroxybenzotriazole or 1-hydroxy-7-azabenzotriazole. The reaction is performed between 20° C. and 40° C., preferably at 25° C. Excess reagents are filtered off and the resin is washed several times with the solvent used during the reaction.

Step C

The reaction is generally known (The combinatorial index, Ed. Bunin, B. A. 1998, Academic Press, p. 133) and is generally performed by stirring resin bound aldehyde or ketone with an excess of amine at low pH (by addition of an acid, such as acetic acid or formic acid) in a solvent such as THF, DMF, N-methylpyrrolidinone, methanol, ethanol, DMSO, dichloromethane, 1,2-dichloroethane, trimethyl orthoformate, triethyl orthoformate, or a mixture of two or more of these. As reducing agent sodium cyanoborohydride may be used. The reaction is performed between 20° C. and 120° C., preferably at 25° C.

Step D

The reaction is generally known (Organic synthesis on solid phase. Dörwald, F. Z. 2000, Wiley VCH, p. 331) and is generally performed by stirring resin bound amine with an excess of isocyanate in a solvent such as THF, DMF, N-methylpyrrolidinone, dichloromethane, 1,2-dichloroethane, toluene or a mixture of two or more of these. The reaction is performed between 20° C. and 80° C., preferably at 25° C.

Step E

The reaction is known (The combinatorial index, Ed. Bunin B. A., 1998, Academic press, p. 21) and is generally performed by stirring resin bound intermediate obtained in step D with a 50–95% solution of TFA. The final cleavage is carried out in a solvent such as THF, dichloromethane, 1,2-dichloroethane, 1,3-dichloropropane, toluene or a mixture of two or more of these. The reaction is performed between 0° C. and 80° C., preferably between 20° C. and 40° C. When the reaction is complete the product is removed by filtration. The resin is successively washed with dichloromethane. The product and washings are collected. The solvent is removed and the product is dried in vacuo.

Optionally, the resin can be a 2-chlorotrityl resin. In that case, step A is a nucleophilic reaction of Fmoc-protected beta alanine with 2-chlorotritylchloride resin in the presence of a base, such as triethylamine or N,N-diisopropyl-N-ethylamine. All other steps are identical to those described above with the exception of step E, cleavage from the resin. This can be done with only 5% TFA in dichloromethane.

More specifically, preparation of the compounds of the invention according to the general procedure (C) may be prepared as follows:

Step A: Resin Bound Fmoc β-alanine (C1)

150 μmol Fmoc β-alanine was dissolved in 500 μl of a mixture of DMF and diisopropylethylamine (430:70) and added to 50 mg polystyrene resin functionalised with a Wang linker. 200 μmol PyBrOP dissolved in DMF (500 μl) was added. After shaking the suspension for 4 hours at 25° C., the resin was isolated by filtration and washed with 3×1 ml DMF.

Step B: Resin Bound 3-(4-formylbenzoylamino) propionic Acid (C2)

To the above resin bound Fmoc β-alanine (C1) was added 1000 μl of a 20% solution of piperidine in DMF. Upon shaking for 30 min, the resin was drained and washed with 1 ml DMF containing HOBt (50 mg/ml) and DMF (2×1 ml). Then 200 μmol 4-formylbenzoic acid (30 mg) and diisopropylethylamine (70 μl) were dissolved in DMF (430 μl) and added to the resin followed by 200 μmol PyBrOP dissolved in DMF (500 μl). The mixture was shaken for 4 hours at 25° C. followed by filtration and washing of the resin with DMF (3×1 ml) and trimethylorthoformate (1×1 ml).

Step C: (C3)

The above resin bound 3-(4-formylbenzoylamino) propionic acid (C2) (50 mg) was treated with a solution of E-NH$_2$ (500 μmol) in a mixture of DMF (500 μl) and trimethylorthoformate (500 μl). Glacial acetic acid (100 μl) was added and the mixture was shaked for 1 hour at 25° C. Sodium cyanoborohydride (750 μmol) suspended in a mixture of DMF and trimethylorthoformate (1:1, 1 ml) was added and the mixture was vortexed at 25° C. for 16 hours followed by filtration and washing with a mixture of DMF and water (4:1, 2×1 ml) followed by 3×1 ml DMF and 2×1 ml dichloromethane to afford (C3).

Step D: (C4)

200 μmol isocyanate (D—N=C=O) dissolved in 500 μl dichloromethane was added to (C3) (50 mg). Shaking the mixture for 16 hours at 25° C. followed by filtration and washing of the resin with 4×1 ml DMF, 2×1 ml water, 3×1 ml THF and 5×1 ml dichloromethane afforded (C4).

Step E (C4) (50 mg) was treated with 1 ml 50% TFA in dichloromethane for 1 hour at 25° C. The product was filtered off and the resin was washed with 1 ml dichloromethane. The combined extracts were concentrated in vacuo. The residue was purified by chromatography and/or crystallisation to afford the compounds of the invention.

Substituted benzothiazol-2-ylamines may be prepared from substituted anilines using the general procedure described in Stuckwisch C. G. *J. Am. Chem. Soc.* 1949 71, 3417.

To a suspension of substituted aniline (9 mmol) and sodium thiocyanate (3.5 g, 43 mmol) in acetic acid (16 ml) was added dropwise, with stirring, bromine (1.4 g, 9 mmol) dissolved in acetic acid (7 ml) while the temperature was kept below 35° C. After all the bromine had been added the mixture was stirred for 16 hours and then filtered and the residue washed with water. The combined filtrate and the washings were neutralized with concentrated aqueous ammonia. The substituted benzothiazol-2-ylamines can be collected on a filter, dried and recrystallized from toluene/hexane. Alternatively, the substituted benzothiazol-2-ylamines may be isolated by extraction.

Substituted 2-aminobenzothiazole (1.2 mmol) was suspended in pyridine (4 ml). Di-phosgene (80 μl, 0.66 mmol) was added and the solution was stirred for two hours at room temperature. To this mixture a solution of 3-{4-[(4-cyclohexylphenylamino)methyl]benzoyl-amino}propionic acid methyl ester (0.61 mmol) and N,N-diisopropylethylamine (0.4 ml, 2.4 mmol) in DMF (4 ml) were added and stirring at 80° C. was continued for 2 hours. The mixture was allowed to cool to room temperature and poured into acetonitrile (50 ml), the resulting precipitate was filtered off and the filtrate was then partitioned between ethyl acetate (50 ml) and hydrochloric acid (2×50 ml, 1 N). The organic phase was concentrated in vacuo to give an oil which was redissolved in ethanol (4 ml). Sodium hydroxide (1 ml, 4 N) was added and the reaction mixture was left at room temperature for 30 min. Hydrochloric acid (4 ml, 1 N) was added, and the resulting precipitate was subsequently collected by filtration to afford the compounds of the invention.

Example 1

3-{4-[3-[1(S)-(4-Chlorophenyl)ethyl]1-(4-cyclohexylphenyl)ureidomethyl benzoylamino}propionic acid

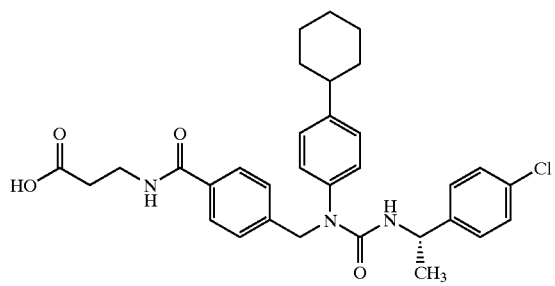

(S)

4-[(4-Cyclohexylphenylamino)methyl]benzoic acid methyl ester

Methyl 4-formylbenzoate (47 g, 285 mmol) was dissolved in methanol (400 ml) and a solution of 4-cyclohexylaniline (50 g, 0.285 mmol) in methanol (200 ml) is slowly added with mechanical stirring. More methanol (1 l) was added and the suspension was stirred at room temperature for 3 days. Filtration, washing and drying in vacuo afforded 90.7 g (99%) of 4-[(4-cyclohexylphenylimino)methyl]benzoic acid methyl ester. This was dissolved in N-methylpyrrolidone (855 ml) and methanol (45 ml). With mechanical stirring sodium borohydride pellets (42.4 g, 1.12 mol) was added in portions keeping the temperature below 40° C. The mixture was then stirred at room temperature for 2 hours and at 40° C. for 16 hours. The mixture was cooled to 5° C. and water (2 l) was slowly added. Then acetone (350 ml) was added and the mixture was stirred at 5° C. for 1 hour. Filtration, washing with water (2×500 ml) and drying in vacuo afforded 78 g (86%) of 4-[(4-cyclohexylphenylamino)-methyl] benzoic acid methyl ester as a solid.

$^1$H NMR (CDCl$_3$): δ1.2–1.4 (5H, m), 1.7–1.85 (5H, m), 2.39 (1H, m), 3.97 (3H, s), 4.04 (1H, bs), 4.39 (2H, s), 6.55 (2H, d), 7.01 (2H, d), 7.44 (2H, d), 8.00 (2H, d).

N-Chlorocarbamoyl-4-[(4-cyclohexylphenylamino) methyl]benzoic acid methyl ester

4-[(4-Cyclohexylphenylamino)methyl]benzoic acid methyl ester (75 g, 0.23 mol) was dissolved in THF (750 ml). Diisopropylethylamine (56.0 ml, 0.32 mmol) and 4-dimethylamino-pyridine (1,0 g, 8.1 mmol) were added. The solution was cooled to 5° C. Bis(trichloromethyl)-carbonate (28.0 g, 0.093 mol) was added in small portions while maintaining the internal reaction temperature below 10° C. The mixture was stirred for a further 2 hours at 10° C., and then transferred to a separatory funnel. Ethyl acetate (800 ml) and water (1000 ml) were added. After mixing, the organic layer was separated, dried with anhydrous sodium sulfate, and concentrated to dryness by rotary evaporation in vacuo. The product was obtained quantitatively as a stable hard crystalline material.

$^1$H NMR (CDCl$_3$): δ7.92 (d, 2H), 7.40 (d, 2H), 7.25 (d, 2H), 7.17 (d, 2H), 4.98 (s, 2H), 3.38 (s, 3H), 2.5 (m, 1H), 1.65–1.80 (m, 5 H), 1.15–1.40 (m, 5 H).

4-[3-[1(S)-(4-Chlorophenyl)ethyl]1-(4-cyclohexylphenyl)ureidomethyl]benzoic acid methyl ester A 2 l reaction flask equipped with mechanical stirring was charged with N-chloro-carbamoyl-4-[(4-cyclohexylphenylamino)methyl]benzoic acid methyl ester (94 g, 0.244 mol), NMP (1.0 l) and triethylamine (68 ml, 0.487 mol). To the clear solution was added drop wise (S)-1-(4-chlorophenyl)ethylamine (38.0 g, 0.244 mol), keeping the internal reaction temperature below 30° C. Stirring was continued for 2 hours, then the reaction mixture was partitioned between water (1.0 l) and ethyl acetate (1.0 l). After extensive mixing, the organic layer was separated, and washed with a 5% aqueous solution of citric acid (500 ml), and saturated ammonium chloride (500 ml), before drying with anhydrous sodium sulfate. Solvent was removed, and the residual oil was evaporated once from acetonitrile. This product was sufficiently pure for further synthesis. Yield: 103 g (84%).

$^1$H NMR (DMSO-d$_6$): δ7.88 (d, 2H), 7.32 (d, 2H), 7.30 (d, 4H), 7.19 (d, 2H), 7.08 (d, 2H), 6.28 (d, 1H), 4.88 (dd, 2H), 4.76 (m, 1H), 3.81 (s, 3H), 2,44 (m, 1H), 1.65–1.80 (m, 5H), 1.15–1.40 (m, 5 H); HPLC-MS (method A): m/z=505 (M+1); Rt=6.17 min.

4-[3-[1(S)-(4-Chlorophenyl)ethyl]1-(4-cyclohexylphenyl)ureidomethyl]benzoic acid 4-[3-[1(S)-(4-Chlorophenyl)ethyl]1-(4-cyclohexylphenyl)ureidomethyl]benzoic acid methyl ester (35.0 g, 69.3 mmol) was dissolved in ethanol (400 ml). 4 N aqueous sodium hydroxide (100 ml) was added and the clear solution was stirred at room temperature for 3 hours. The solution was neutralised with 4 N hydrochloric acid (100 ml), and placed upon an ice bath to initiate crystallization. The crystals were collected, washed extensively with water, and dried in vacuo over night. Yield: 34.25 g (100%).

$^1$H NMR (DMSO-d$_6$): δ12.85 (bs, 1H), 7.85 (d, 2H), 7.32 (d, 2H), 7.30 (d, 4H), 7.19 (d, 2H), 7.08 (d, 2H), 6.27 (d, 1H), 4.85 (m, 3H), 2.45 (m, 1H), 1.65–1.80 (m, 5 H), 1.15–1.40 (m, 5 H); HPLC-MS (method A): m/z=491 (M+1); Rt=5.50 min.

3-{4-[3-[1(S)-(4-Chlorophenyl)ethyl]1-(4-cyclohexylphenyl)ureidomethyl]benzoylamino}propionic acid methyl ester 4-[3-[1(S)-(4-Chlorophenyl)ethyl]1-(4-cyclohexylphenyl)ureidomethyl]benzoic acid (1.0 g, 2.04 mmol) was dissolved in DMF (8 ml) and HOBt (410 mg, 3.05 mmol), and EDAC (580 mg, 3.05 mmol) were added. The solution was stirred at room temperature for 30 min. A solution of 3-aminopropionic acid methyl ester hydrochloride (310 mg, 3.05 mmol) and N,N-diisopropylethylamine (530 µl, 3 mmol) in DMF (2 ml) was added, and the reaction mixture was stirred at ambient temperature over night. The reaction mixture was partitioned between ethyl acetate (70 ml) and water (3×50 ml). The organic phase was dried with anhydrous sodium sulfate and evaporated to dryness to afford 1.17 g (99%) of 3-{4-[3-[1(S)-(4-chloro-phenyl)ethyl]1-(4-cyclohexylphenyl)ureidomethyl]benzoylamino}propionic acid methyl ester. HPLC-MS (method A): m/z=576 (M+1); Rt=5.47 min.

3-{4-[3-[1(S)-(4-Chlorophenyl)ethyl]1-(4-cyclohexylphenyl)ureidomethyl]benzoylamino}propionic acid 3-{4-[3-[1(S)-(4-Chlorophenyl)ethyl]1-(4-cyclohexylphenyl)ureidomethyl]benzoyl-amino}propionic acid methyl ester (1.1 g, 1.9 mmol) was dissolved in methanol (10 ml) and 1N aqueous sodium hydroxide (5.7 ml) was added. The reaction mixture was stirred at room temperature for 2 hours. Then 1N hydrochloric acid was added and the solvent was removed by rotary evaporation in vacuo. The residue was re-dissolved in ethyl acetate and diethyl ether and crystallised using sonication. Concentration in vacuo followed by re-suspension in a aqueous hydrochloric acid and sinication for 30 min afforded after filtration, washing with water and drying in vacuo 0.55 g (51%) of the title compound as a solid.

$^1$H NMR (DMSO-d$_6$): δ1.2–1.4 (9H, m), 1.65–1.8 (5H, m), 3.45 (2H, m), 4.8–4.9 (3H, m), 6.28 (1H, d), 7.08 (2H, d), 7.20 (2H, d), 7.25 (2H, d), 7.30 (2H, d), 7.33 (2H, d), 7.72 (2H, d), 8.45 (1H, t), 12.3 (1H, bs); HPLC-MS (method A): m/z=562 (M+1); Rt=5.08 min.

Example 2

General Procedure (B)

3-{4-[3-(3-Bromophenyl)-1-(4-cyclohex-1-enylphenyl)ureidomethyl]benzoylamino}propionic acid

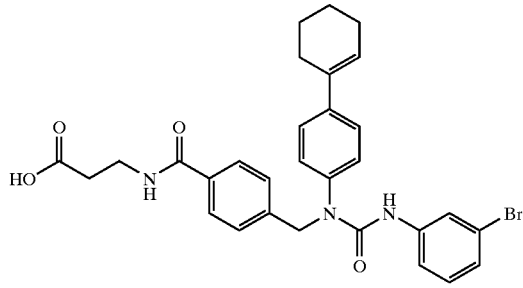

Starting material: 3-(4-formylbenzoylamino) propionic acid methyl ester

4-Formylbenzoic acid (25 g, 0.167 mol) was dissolved in DMF (250 ml) and added HOBt (38.3 g, 0.2 mol) and, in portions, 1-[3-(dimethylamino)propyl]3-ethylcarbodiimide hydrochloride (27.1 g, 0.2 mol) and the resulting mixture was stirred at room temperature for 16 hours. More 1-[3-(dimethylamino)propyl]3-ethylcarbodiimide hydrochloride (11.2 g, 84 mmol) was added and the mixture was stirred at room temperature for 2.5 hours. More 1-[3-(dimethylamino) propyl]3-ethylcarbodiimide hydrochloride (5.5 g, 41 mmol) was added and the mixture was stirred at room temperature for 2 hours. Water (500 ml) was added and the mixture was extracted with ethyl acetate (500 ml). The organic phase was washed with water (2×400 ml), dried (sodium sulphate) and evaporated in vacuo. This afforded 20 g (51%) of 3-(4-formylbenzoylamino)propionic acid methyl ester as a solid.

¹H NMR (CDCl₃): δ2.69 (2H, t), 3.74 (3H, s), 3.77 (2H, q), 7.05 (1H, bt), 7.93 (4H, m), 10.1 (1H, s); HPLC-MS (Method A): m/z=236 (M+1); R$_t$=1.79 min.

Step A: 3-{4-[(4-cyclohex-1-enylphenylamino)methyl]benzoylamino}propionic acid methyl ester 3-(4-Formylbenzoylamino)propionic acid methyl ester (10 g, 42.5 mmol) was dissolved in methanol (100 ml). With mechanical stirring a solution of 4-cyclohex-1-enylaniline (7.4 g, 42.5 mmol) in methanol (15 ml) was added and the resulting suspension was stirred at room temperature for 2.5 hours. Sodium cyano borohydride (4.01 g, 63.8 mmol) was added in portions and the resulting mixture was stirred at room temperature for 4 days. Filtration afforded 7.1 g of a solid and recrystallisation from methanol afforded 3.55 g of 3-{4-[(4-cyclohex-1-enylphenylamino)methyl]benzoylamino}propionic acid methyl ester.

¹H NMR (DMSO-d₆): δ1.55 (2H, m), 1.67 (2H, m), 2.12 (2H, m), 2.25 (2H, m), 2.60 (2H, t), 3.48 (2H, q), 3.60 (3H, s), 4.33 (2H, d), 5.90 (1H, t), 6.32 (1H, t), 6.48 (2H, d, 7.09 (2H, d), 7.40 (2H, d), 7.76 (2H, d), 8.49 (1H, t); HPLC-MS (Method A): m/z=393 (M+1); R$_t$=4.54 min.

Step B

Preparation of 3-bromophenylisocyanate, diphosgene method

3-Bromoaniline (2.63 g, 15.3 mmol) was dissolved in ethyl acetate (100 ml) and 1N dry hydrogen chloride in diethyl ether (15.3 ml) was added and the solvents were removed in vacuo. The residue was stripped twice with toluene and the residue was suspended in toluene (30 ml). Diphosgene (6.1 ml) was added and the mixture was refluxed for 1.5 hour. After cooling, the solution was concentrated in vacuo to afford 2.63 g (87%) 3-bromophenylisocyanate.

3-{4-[3-(3-Bromophenyl)-1-(4-cyclohex-1-enylphenyl)ureidomethyl]benzoylamino}propionic acid methyl ester 3-{4-[(4-Cyclohex-1-enylphenylamino)methyl]benzoylamino}propionic acid methyl ester (0.94 g, 2.34 mmol) was stripped once with toluene and dissolved in DMF (15 ml) and added 0.47 g (2.34 mmol) 3-bromophenylisocyanate. The resulting mixture was stirred at room temperature for 3 days. Ethyl acetate (100 ml) was added and the mixture was washed with water (2×80 ml), and the organic phase was dried (sodium sulphate) and concentrated in vacuo. The residue was purified by column chromatography on silica gel eluting first with a mixture of ethyl acetate and heptane (1:6), then with a mixture of ethyl acetate, heptane and formic acid (1:2:0.3). Pure fractions were concentrated, re-dissolved in ethyl acetate and treated with activated carbon, filtered and concentrated in vacuo. This afforded 0.64 g (43%) of 3-{4-[3-(3-bromophenyl)-1-(4-cyclohex-1-enylphenyl)ureidomethyl]benzoylamino}propionic acid methyl ester as an oil.

¹H NMR (DMSO-d₆): δ1.68 (2H, m), 1.82 (2H, m), 2.25 (2H, m), 2.40 (2H, m), 2.65 (2H, t), 3.70 (5H, m), 4.93 (2H, s), 6.19 (1H, s), 6.32 (1H, s), 6.98 (1H, t), 7.05–7.13 (4H, m), 7.21 (1H, d), 7.32 (2H, d), 7.43 (2H, d), 7.55 (1H, s), 7.69 (2H, d); HPLC-MS (Method A): m/z=592 (M+1); R$_t$=5.42 min.

Step C: 3-{4-[3-(3-Bromophenyl)-1-(4-cyclohex-1-enylphenyl)ureidomethyl]benzoylamino}propionic acid 3-{4-[3-(3-Bromophenyl)-1-(4-cyclohex-1-enylphenyl)ureidomethyl]benzoylamino}propionic acid methyl ester (0.64 g, 1.08 mmol) was dissolved in THF (10 ml) and lithium hydroxide (0.043 g, 1.08 mmol) in water (1 ml) was added and the resulting mixture was stirred at room temperature for 16 hours. More lithium hydroxide (0.043 g, 1.08 mmol) in water (1 ml) was added and, after 4 hours, 1N hydrochloric acid (2.2 ml) was added. The mixture was concentrated in vacuo and the residue was triturated with water, filtered and dried in vacuo at 40° C. to afford 0.378 g (61%) of 3-{4-[3-(3-bromophenyl)-1-(4-cyclohex-1-enylphenyl)ureidomethyl]benzoylamino}propionic acid.

¹H NMR (DMSO-d₆): δ1.60 (2H, m), 1.72 (2H, m), 2.17 (2H, m), 2.34 (2H, m), 2.50 (2H, m, Below DMSO), 3.44 (2H, q), 4.96 (2H, s), 6.18 (1H, m), 7.1–7.2 (4H, m), 7.32 (2H, d), 7.40 (2H, d), 7.45 (1H, d), 7.75 (3H, m), 8.40 (1H, s), 8.49 (1H, t), 12.2 (1H, bs); HPLC-MS (Method A): m/z=578 (M+1); R$_t$=5.02 min.

Example 3

General Procedure (B)

3-{4-[3-(3-Trifluoromethoxyphenyl)-1-(4-cyclohex-1-enylphenyl)ureidomethyl]benzoylamino}propionic acid

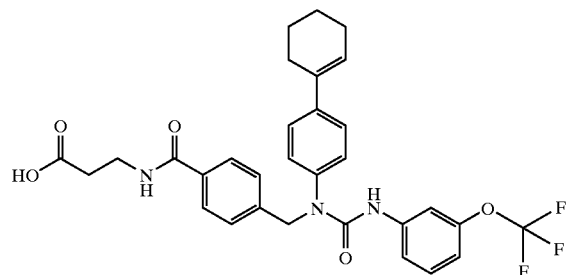

Step B: Di-tert-butyltricarbonate Method

Di-tert-butyltricarbonate (0.26 g, 1 mmol) was dissolved in dichloromethane (1 ml) and a solution of 3-trifluoromethoxyaniline (0.18 g, 1 mmol) in dichloromethane (0.5 ml) was added. The mixture was stirred at room temperature for 15 minutes and 3-{4-[(4-cyclohex-1-enylphenylamino)methyl]benzoylamino}propionic acid methyl ester (0.39 g, 1 mmol) was added and the resulting mixture was stirred at room temperature for 4 days. The mixture was concentrated in vacuo and the residue was purified by column chromatography on silica gel eluting first with a mixture of ethyl acetate and heptane (1:6), then with a mixture of ethyl acetate, heptane and formic acid (1:2:0.15). This afforded 0.256 g (43%) of 3-{4-[3-(3-trifluoro-methoxyphenyl)-1-(4-cyclohex-1-enylphenyl)ureidomethyl]benzoylamino}propionic acid methyl ester.

¹H NMR (CDCl₃): δ1.68 (2H, m), 1.80 (2H, m), 2.17 (2H, m), 2.22 (2H, m), 2.40 (2H, m), 2.68 (2H, t), 3.70 (5H, m), 3.44 (2H, q), 4.95 (2H, s), 6.20 (1H, s), 6.33 (1H, s), 6.85 (2H, m), 7.05 (2H, d), 7.11 (1H, d), 7.23 (1H, t), 7.35 (2H, d), 7.40 (3H, m), 7.70 (2H, d); HPLC-MS (Method A): m/z=596 (M+1); R$_t$=5.49 min.

Step C

Hydrolysis as described above afforded 0.19 g (47%) 3-{4-[3-(3-trifluoromethoxy-phenyl)-1-(4-cyclohex-1-enylphenyl)ureidomethyl]benzoylamino}propionic acid.

¹H NMR (DMSO-d₆): δ1.59 (2H, m), 1.70 (2H, m), 2.17 (2H, m), 2.33 (2H, m), 2.39 (2H, t), 3.41 (2H, q), 4.97 (2H, s), 6.17 (1H, m), 6.93 (1H, d), 7.3–7.4 (5H, m), 7.46 (1H, d), 7.60 (1H, s), 7.77 (2H, d), 8.50 (1H, s), 8.58 (1H, t); HPLC-MS (Method A): m/z=578 (M+1); $R_f$=5.02 min.

Example 4

General Procedure (B)

3-{4-[1-(4-Cyclohexylphenyl)-3-(3-fluoro-5-trifluoromethylphenyl)ureidomethyl]benzoylamino}propionic acid

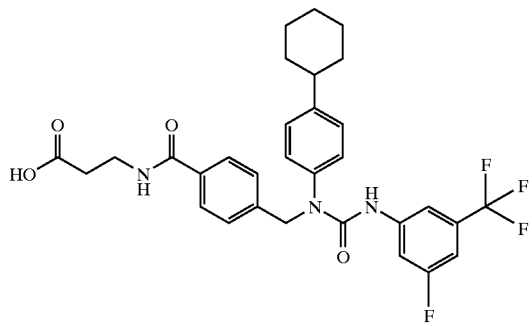

Step A: 3-{4-[(4-cyclohexylphenylamino)methyl]benzoylamino}propionic acid methyl ester 3-(4-Formylbenzoylamino)propionic acid methyl ester (10 g, 42.5 mmol) was dissolved in methanol (100 ml). With mechanical stirring 4-cyclohexylaniline (7.4 g, 42.5 mmol) was added in portions. Methanol (100 ml) was added and the resulting suspension was stirred under nitrogen at room temperature for 3 hours. Sodium cyano borohydride (4.01 g, 63.8 mmol) was added in portions and the resulting solution was stirred at room temperature for 4 days. Filtration and drying in vacuo of the formed crystals afforded 6.40 g (38%) of 3-{4-[(4-cyclohexylphenylamino)methyl]benzoylamino}propionic acid methyl ester as a solid. From the mother liquor a second crop of 2.49 g (15%) could be isolated by concentration in vacuo followed by washing with methanol.

HPLC-MS (Method A): m/z=395 (M+1); $R_f$=4.53 min.

Step B

Step B was performed using the di-tert-butyltricarbonate method as described above.

Data for the title compound:

$^1$H NMR (DMSO-d$_6$): δ1.3–1.5 (5H, m), 1.7–1.9 (5H, m), 2.55 (2H, m), 2.70 (2H, t), 3.72 (2H, q), 4.94 (2H, s), 6.44 (1H, s), 6.85 (1H, t), 6.93 (1H, d), 7.08 (3H, m), 7.18 (1H, s), 7.24–7.35 (3H, m), 7.52 (1H, d), 7.69 (2H, d); HPLC-MS (Method A): m/z=586 (M+1); $R_f$=5.31 min.

Example 5

General Procedure (B)

3-{4-[3-(3-Bromophenyl)-1-(4-Cyclohexylphenyl)ureidomethyl]benzoylamino}propionic acid

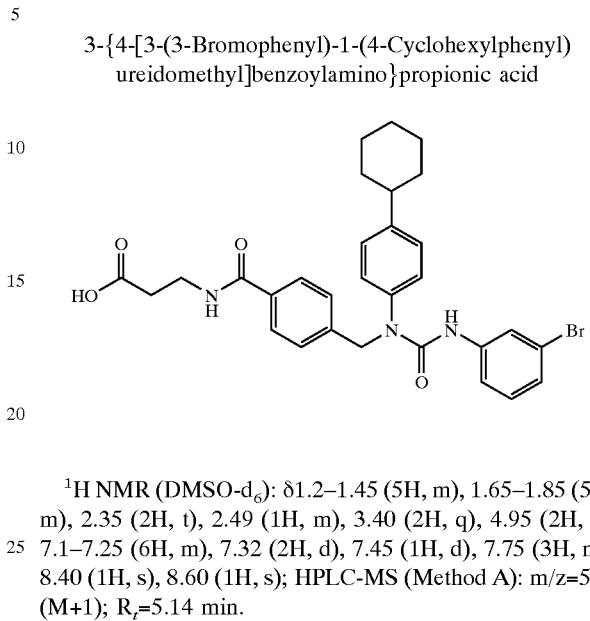

$^1$H NMR (DMSO-d$_6$): δ1.2–1.45 (5H, m), 1.65–1.85 (5H, m), 2.35 (2H, t), 2.49 (1H, m), 3.40 (2H, q), 4.95 (2H, s), 7.1–7.25 (6H, m), 7.32 (2H, d), 7.45 (1H, d), 7.75 (3H, m), 8.40 (1H, s), 8.60 (1H, s); HPLC-MS (Method A): m/z=578 (M+1); $R_f$=5.14 min.

Example 6

General Procedure (B)

3-{4-[1-(4-Cyclohexen-1-ylphenyl)-3-(3-methanesulfonyl-4-trifluoromethoxyphenyl)ureidomethyl]benzoylamino}propionic acid

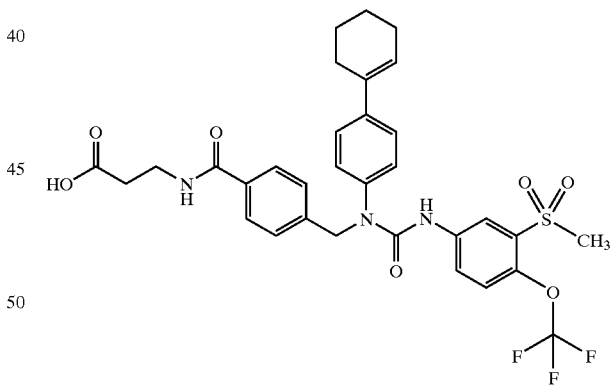

The synthesis of the intermediate 3-methylsulfonyl-4-trifluoromethoxyaniline and its conversion to the corresponding isocyanate was performed as described earlier in WO 00/69810.

$^1$H NMR (DMSO-d$_6$): δ1.59(2H, m), 1.70(2H m), 2.14 (2H, m), 2.50(2H, below DMSO signal), 3.26(3H, s), 3.43 (2H, m), 4.96(2H, s), 6.18(1H, t), 7.18 (2H, d), 7.32 (2H, d), 7.40 (2H, d) 7.54(1H, d), 7.54(2H, d), 7.98(1H, d), 8.16 (1H, s), 8.45 (1H, broad), 8.85 (1H, s), 12.2 (1H, bs); HPLC-MS (Method A): m/z=660 (M+1); $R_f$=7.47 min.

Example 7

General Procedure (B)

3-{4-[1-(4-Cyclohexylphenyl)-3-(3-trifluoromethylphenyl)ureidomethyl]benzoylamino}propionic acid

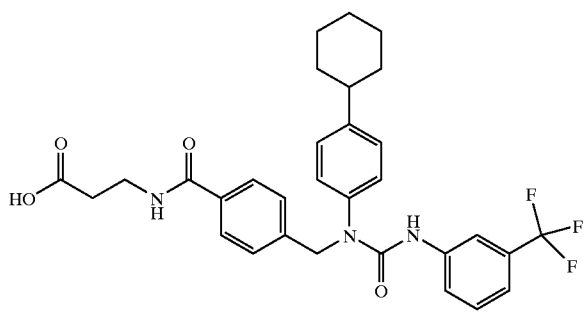

Prepared according to the di-tert-butyltricarbonate method.

$^1$H NMR (DMSO-d$_6$): δ1.13–1.42 (5H, m), 1.63–1.86 (5H, m), 2.50 (below DMSO-signal), 3.42 (2H, q), 4.95 (2H, s), 7.12–7.24 (4H, m), 7.28 (1H, d), 7.35 (2H, d), 7.45 (1H, d), 7.74 (3H, m), 7.90 (1H, s), 8.47 (1H, t), 8.56 (1H, s), 12.25 (1H, broad); HPLC-MS (Method B): m/z=568 (M+1); R$_t$=8.08 min.

Example 8

General Procedure (B)

3-{4-[3-(3-Cyano-5-trifluoromethylphenyl)-1-(4-cyclohexylphenyl)ureidomethyl]benzoylamino}propionic acid

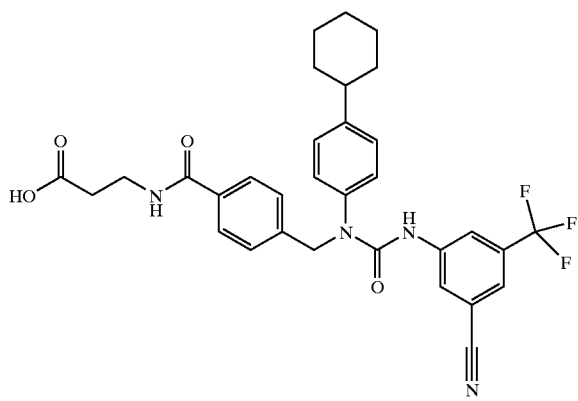

Prepared according to the di-tert-butyltricarbonate method.

$^1$H NMR (DMSO-d$_6$) selected: δ1.2–1.4 (5H, m), 1.6–1.8 (5H, m), 2.42 (2H, m), 4.95 (2H, s), 7.12 (2H, d), 7.22 (4H, dd), 7.28 (1H, d), 7.34 (2H, d), 7.75 (2H, d), 8.21 (1H, s), 8.53 (1H, t); HPLC-MS (Method B): m/z=593 (M+1); R$_t$=8.03 min.

Example 9

General Procedure (B)

3-{4-[3-(3-Cyano-5-trifluoromethylphenyl)-1-(4-cyclohex-1-enylphenyl)ureidomethyl]benzoylamino}propionic acid

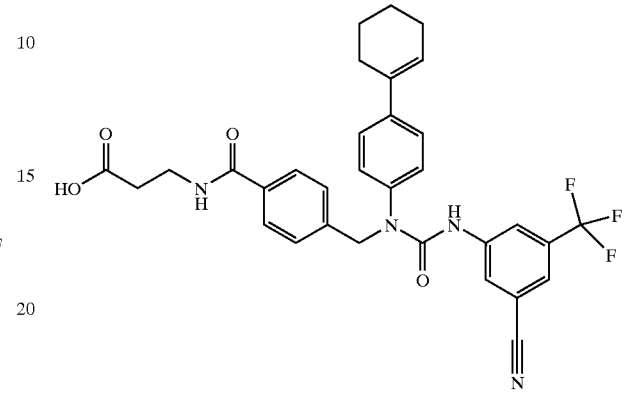

Prepared according to the di-tert-butyltricarbonate method.

$^1$H NMR (DMSO-d$_6$): δ1.60 (2H, m), 1.72 (2H, m), 2.20 (2H, m), 2.36 (2H, m), 2.50 (below DMSO-signal), 3.43 (2H, q), 4.97 (2H, s), 6.20 (1H, s), 7.21 (2H, d), 7.32 (2H, d), 7.41 (2H, d), 7.74 (2H, d), 7.87 (1H, s), 8.21 (1H, s), 8.27 (1H, s), 8.50 (1H, t), 8.83 (1H, s); HPLC-MS (Method B): m/z=591 (M+1); R$_t$=7.50 min.

Example 10

General Procedure (B)

3-{4-[1-(4-Cyclohexylphenyl)-3-(3-hydroxymethyl-4-trifluoromethoxyphenyl)ureidomethyl]benzoylamino}propionic acid

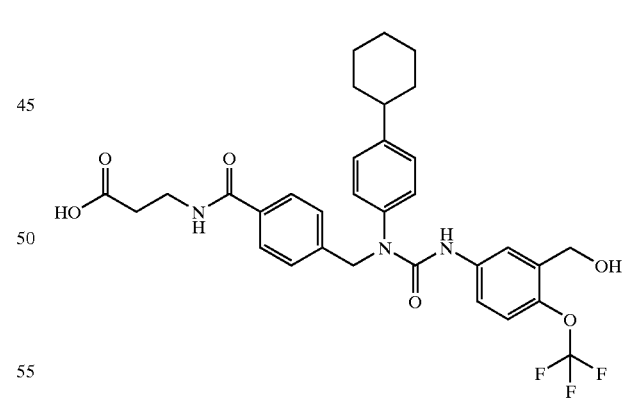

Prepared according to the di-tert-butyltricarbonate method.

Preparation of the intermediate (trimethylsilyl protected) 3-hydroxymethyl-4-trifluoromethoxyaniline was performed as described in WO 00/69810.

$^1$H NMR (DMSO-d$_6$): δ1.18–1.42 (5H, m), 1.66–1.84 (5H, m), 2.50 (below DMSO-signal), 3.44 (2H, q), 4.50 (2H, t), 4.95 (2H, s), 5.33 (1H, t), 7.1–7.2 (5H, m), 7.32 (2H, d), 7.50 (1H, d), 7.64 (1H, s), 7.75 (2H, d), 8.42 (1H, s), 8.49

(1H, t); HPLC-MS (Method B): m/z=614 (M+1); $R_t$=6.93 min. M.p. 167.5–168.5° C. Microanalysis: Calculated for $C_{32}H_{34}F_3N_3O_6$: C, 62.64%; H, 5.58%; N, 6.85%; Found: C, 62.11%; H, 5.72%; N, 6.71%.

Example 11

General Procedure (B)

3-{4-[1-(4-Cyclohex-1-enylphenyl)-3-(3-hydroxymethyl-4-trifluoromethoxyphenyl)ureidomethyl]benzoylamino}propionic acid

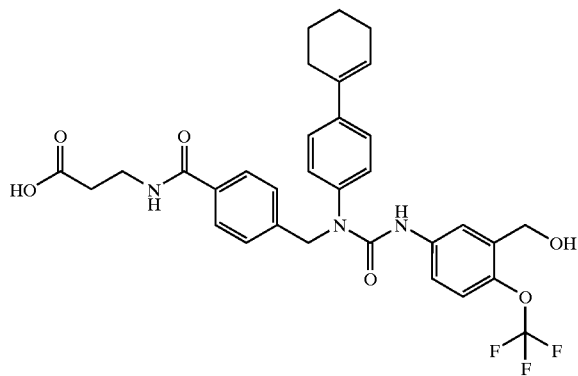

Prepared according to the di-tert-butyltricarbonate method.

$^1$H NMR (DMSO-$d_6$): δ1.60 (2H, m), 1.70 (2H, m), 2.17 (2H, m), 2.33 (2H, m), 2.50 (below DMSO-signal), 3.42 (2H, q), 4.50 (2H, t), 4.97 (2H, s), 5.33 (1H, t), 6.18 (1H, s), 7.17 (3H, m), 7.32 (2H, d), 7.40 (2H, d), 7.50 (1H, m), 7.64 (1H, s), 7.75 (2H, d), 8.47 (3H, m) 12.25 (1H, broad); HPLC-MS (Method B): m/z=612 (M+1); $R_t$=7.38 min.

Pharmacological Methods

In the following section binding assays as well as functional assays useful for evaluating the efficiency of the compounds of the invention are described.

Binding of compounds to the glucagon receptor may be determined in a competition binding assay using the cloned human glucagon receptor.

Antagonism may be determined as the ability of the compounds to inhibit the amount of cAMP formed in the presence of 5 nM glucagon.

Glucagon Binding Assay (I)

Receptor binding is assayed using cloned human receptor (Lok et al., Gene 140, 203–209 (1994)). The receptor is inserted in the pLJ6' expression vector using EcoRI/SSt1 restriction sites (Lok et al.) is expressed in a baby hamster kidney cell line (A3 BHK 570-25). Clones are selected in the presence of 0.5 mg/ml G-418 and are shown to be stable for more than 40 passages. The $K_d$ is shown to be 0.1 nM.

Plasma membranes are prepared by growing cells to confluence, detaching them from the surface and resuspending the cells in cold buffer (10 mM tris/HCl, pH 7.4 containing 30 mM NaCl, 1 mM dithiothreitol, 5 mg/l leupeptin (Sigma), 5 mg/l pepstatin (Sigma), 100 mg/l bacitracin (Sigma) and 15 mg/l recombinant aprotinin (Novo Nordisk A/S)), homogenization by two 10-s bursts using a Polytron PT 10-35 homogenizer (Kinematica), and centrifugation upon a layer of 41 w/v % sucrose at 95.000×g for 75 min. The white band located between the two layers is diluted in buffer and centrifuged at 40.000×g for 45 min. The precipitate containing the plasma membranes is suspended in buffer and stored at −80° C. until use.

Glucagon is iodinated according to the chloramine T method (Hunter and Greenwood, Nature 194, 495 (1962)) and purified using anion exchange chromatography (Jørgensen et al., Hormone and Metab. Res. 4, 223–224 (1972). The specific activity is 460 μCi/μg on the day of iodination. Tracer is stored at −18° C. in aliquots and are used immediately after thawing.

Binding assays are carried out in triplicate in filter microtiter plates (MADV N65, Millipore). The buffer used in this assay is 50 mM HEPES, 5 mM EGTA. 5 mM MgCl$_2$, 0.005% tween 20, pH 7.4. Glucagon is dissolved in 0.05 M HCl, added an equal amount (w/w) of human serum albumin and freeze-dried. On the day of use, it is dissolved in water and diluted in buffer to the desired concentrations.

Test compounds are dissolved and diluted in DMSO. 140 μl buffer, 25 μl glucagon or buffer, and 10 μl DMSO or test compound are added to each well. Tracer (50.000 cpm) is diluted in buffer and 25 μl are added to each well. 1–4 μg freshly thawed plasma membrane protein diluted in buffer is then added in aliquots of 25 μl to each well. Plates are incubated at 30° C. for 2 hours. Non-specific binding is determined with $10^{-6}$ M of glucagon. Bound tracer and unbound tracer are then separated by vacuum filtration (Millipore vacuum manifold). The plates are washed with 2×100 μl buffer/ well. The plates are air dried for a couple of hours, where-upon the filters are separated from the plates using a Millipore Puncher. The filters are counted in a gamma counter.

Functional Assay (I)

The functional assay is carried out in 96 well microtiter plates (tissue culture plates, Nunc). The resulting buffer concentrations in the assay are 50 mM tris/HCl, 1 mM EGTA, 1.5 mM MgSO$_4$, 1.7 mM ATP, 20 μM GTP, 2 mM IBMX, 0.02% tween-20 and 0.1% human serum albumin. pH is 7.4. Glucagon and proposed antagonist are added in aliquots of 35 μl diluted in 50 mM tris/HCl, 1 mM EGTA, 1.85 mM MgSO$_4$, 0.0222% tween-20 and 0.111% human serum albumin, pH 7.4.20 μl of 50 mM tris/HCl, 1 mM EGTA, 1.5 mM MgSO$_4$, 11.8 mM ATP, 0.14 mM GTP, 14 mM IBMX and 0.1% human serum albumin, pH 7.4 is added. GTP is dissolved immediately before the assay.

50 μl containing 5 μg of plasma membrane protein is added in a tris/HCl, EGTA, MgSO$_4$, human serum albumin buffer (the actual concentrations are dependent upon the concentration of protein in the stored plasma membranes).

The total assay volume is 140 μl. The plates are incubated for 2 hours at 37° C. with continuous shaking. Reaction is terminated by addition of 25 μl 0.5 N HCl. cAMP is measured by the use of a scintillation proximity kit (Amersham).

Glucagon Binding Assay (II)

BHK (baby hamster kidney cell line) cells are transfected with the human glucagon receptor and a membrane preparation of the cells is prepared. Wheat Germ Agglutinin derivatized SPA beads containing a scintillant (WGA beads) (Amersham) bound the membranes. $^{125}$I-glucagon bound to human glucagon receptor in the membranes and excited the scintillant in the WGA beads to light emission. Glucagon or samples binding to the receptor competed with $^{125}$I-glucagon.

All steps in the membrane preparation are kept on ice or performed at 4° C. BHK cells are harvested and centrifuged. The pellet is resuspended in homogenisation buffer (25 mM HEPES, pH=7.4, 2.5 mM CaCl$_2$, 1.0 mM MgCl$_2$, 250 mg/l bacitracin, 0, 1 mM Pefabloc), homogenised 2×10 sec using Polytron 10–35 homogenizer (Kinematica) and added the same amount of homogenisation buffer as used for resuspension. After centrifugation (15 min at 2000×g) the supernatant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM CaCl$_2$, 1.0 mM MgCl$_2$) and homogenised 2×10 sec. (Polytron). The protein concentration is normally around 1.75 mg/ml. Stabilisation buffer (25 mM HEPES, pH=7.4, 2.5 mM CaCl$_2$, 1.0 mM MgCl$_2$, 1% bovine serum albumin, 500 mg/l bacitracin, 2.5 M sucrose) is added and the membrane preparation is stored at −80° C.

The glucagon binding assay is carried out in opti plates (Polystyrene Microplates, Packard). 50 μL assay buffer (25 mM HEPES, pH=7.5, 2.5 mM CaCl$_2$, 1.0 mM MgCl$_2$, 0.003% Tween-20, 0.005% bacitracin, 0.05% sodium azide) and 5 μl glucagon or test compound (in DMSO) are added to each well. 50 μl tracer ($^{125}$I-porcine glucagon, 50.000 cpm) and 50 μl membranes (7.5 μg) containing the human glucagon receptor are then added to the wells. Finally 50 μl WGA beads containing 1 mg beads are transferred to the well. The opti plates are incubated for 4 hours on a shaker and then settled for 8–48 hours. The opti plates are counted in a Topcounter. Non-specific binding is determined with 500 nM of glucagon.

GIP Binding Assay

BHK (baby hamster kidney cell line) cells are transfected with the human GIP receptor and a membrane preparation of the cells is prepared. Wheat Germ Agglutinin derivatized SPA beads containing a scintillant (WGA beads) (Amersham) bound the membranes. $^{125}$I-GIP bound to human GIP receptor in the membranes and excited the scintillant in the WGA beads to light emission. GIP or samples binding to the receptor competed with $^{125}$I-GIP.

All steps in the membrane preparation are kept on ice or performed at 4° C. BHK cells are harvested and centrifuged. The pellet is resuspended in homogenisation buffer (25 mM HEPES, pH=7.4, 2.5 mM CaCl$_2$, 1.0 mM MgCl$_2$, 250 mg/l bacitracin, 0.1 mM Pefabloc), homogenised 2×10 sec using Polytron 10–35 homogenizer (Kinematica) and added the same amount of homogenisation buffer as used for resuspension. After centrifugation (15 min at 2000×g) the supernatant is transferred to cold centrifuge tubes and centrifuged for 45 min at 40.000×g. The pellet is resuspended in homogenisation buffer, homogenised 2×10 sec (Polytron) and additional homogenisation buffer is added. The suspension is centrifuged for 45 min at 40.000×g and the pellet is resuspended in resuspension buffer (25 mM HEPES, pH=7.4, 2.5 mM CaCl$_2$, 1.0 mM MgCl$_2$) and homogenised 2×10 sec. (Polytron). The protein concentration is normally around 1.75 mg/ml. Stabilisation buffer (25 mM HEPES, pH=7.4, 2.5 mM CaCl$_2$, 1.0 mM MgCl$_2$, 1% bovine serum albumin, 500 mg/l bacitracin, 2.5 M sucrose) is added and the membrane preparation is stored at −80° C.

The GIP binding assay is carried out in opti plates (Polystyrene Microplates, Packard). 50 μl assay buffer (25 mM HEPES, pH=7.5, 2.5 mM CaCl$_2$, 1.0 mM MgCl$_2$, 0.003% Tween-20, 0.005% bacitracin, 0.05% sodium azide) and 5 μl GIP or test compound (in DMSO) are added to each well. 50 μl tracer ($^{125}$I-porcine GIP, 50.000 cpm) and 50 μl membranes (20 μg) containing the human GIP receptor are then added to the wells. Finally 50 μl WGA beads containing 1 mg beads are transferred to the well. The opti plates are incubated for 3.5 hours on a shaker and then settled for 8–48 hours. The opti plates are counted in a Topcounter. Non-specific binding is determined with 500 nM of GIP.

The compounds according to the examples showed the following data when tested in the glucagon binding assay (II) and GIP binding assay, respectively:

| Example No | Glucagon binding assay (II), IC$_{50}$, nM | GIP binding assay, IC$_{50}$; nM |
|---|---|---|
| 1 | 64 | 644 |
| 2 | 53 | 198 |
| 3 | 25 | 34 |
| 4 | 29 | 90 |
| 5 | 42 | 265 |
| 6 | 9 | 177 |
| 7 | 29 | 82 |
| 8 | 35 | 76 |
| 9 | 42 | 122 |
| 10 | 49 | 107 |
| 11 | 64 | 152 |

What is claimed is:
1. A compound which is selected from

3-{4-[1-(4-cyclohexylphenyl)-3-(3-trifluoromethoxyphenyl)ureidomethyl]benzoylamino}propionic acid, 3-{4-[1-(4-cyclohex-1-enylphenyl)-3-(3-trifluoromethoxyphenyl)ureidomethyl]benzoylamino}propionic acid, 3-{4-[1-(4-cyclohexylcyclohexyl)-3-(3-trifluoromethoxyphenyl)ureidomethyl]benzoylamino}propionic acid, 3-{4-[1-(4-cyclohexylcyclohexyl)-3-(3-trifluoromethoxyphenyl)ureidomethyl]benzoylamino}propionic acid, 3-{4-[1-(4-cyclohexylphenyl)-3-(3-trifluoromethoxyphenyl)ureidomethyl]benzoylamino}propionic acid, 3-{4-[1-(4-cyclohexylphenyl)-3-(3-bromophenyl)ureidomethyl]benzoylamino}propionic acid, 3-{4-[1-(4-cyclohex-1-enylphenyl)-3-(3-bromophenyl)ureidomethyl]benzoylamino}propionic acid, 3-{4-[1-(4-cyclohexylphenyl)-3-(3-trifluoromethyl-5-fluorophenyl)ureidomethyl]benzoylamino}propionic acid, 3-{4-[1-(4-cyclohexylcyclohexyl)-3-(3-bromophenyl)ureidomethyl]benzoylamino}propionic acid, 3-{4-[1-(4-cyclohexylphenyl-3-(3-trifluoromethyl-5-fluorophenyl)ureidomethyl]benzoylamino}propionic acid, 3-{4-[1-(4-cyclohexylphenyl)-3-(3-trifluoromethyl-5-cyanophenyl)ureidomethyl]benzoylamino}propionic acid, 3-{4-[1-(4-cyclohexylphenyl)-3-(3-chlorophenyl)ureidomethyl]benzoylamino}propionic acid, 3-{4-[1-(4-cyclohexylcyclohexyl)-3-(3-trifluoromethyl-5-cyanophenyl)ureidomethyl]benzoylamino}propionic acid, 3-{4-[1-(4-cyclohexylcyclohexyl)-3-(3-chlorophenyl)ureidomethyl]benzoylamino}propionic acid,
3-{4-[1-(4-cyclohex1-enylphenyl)-3-(3-chlorophenyl)ureidomethyl]benzoylamino}propionic acid,
3-{4-[1-(4-cyclohexylphenyl)-3-(3-methylsulfonyl-4-trifluoromethoxyphenyl)ureidomethyl]benzoylamino}propionic acid,
3-{4-[1-(4-cyclohexylcyclohexyl)-3-(3-methylsulfonyl-4-trifluoromethoxyphenyl)ureidomethyl]benzoylamino}propionic acid,
3-{4-[1-(4-cyclohexylcyclohexyl)-3-(3-methylsulfonylphenyl)ureidomethyl]benzoylamino}propionic acid,
3-{4-[1-(4-cyclohex-1-enylphenyl)-3-(3-methylsulfonyl-4-trifluoromethoxyphenyl)ureidomethyl]benzoylamino}propionic acid,
3-{4-[1-(4-cyclohex-1-enylphenyl)-3-(3-methylsulfonylphenyl)ureidomethyl]benzoylamino}propionic acid,
3-{4-[1-(4-cyclohexylphenyl)-3-(3-tert-butylphenyl)ureidomethyl]benzoylamino}propionic acid,
3-{4-[1-(4-cyclohex-1-enylphenyl)-3-(3-tert-butylphenyl)ureidomethyl]benzoylamino}propionic acid,
3-{4-[1-(4-cyclohexylcyclohexyl)-3-(3-tert-butylphenyl)ureidomethyl]benzoylamino}propionic acid,
3-{4-[1-(4-cyclohexylcyclohexyl)-3-(3hydroxymethyl-4-trifluoromethoxyphenyl)ureidomethyl]benzoylamino}propionic acid,
3-{4-[1-(4-cyclohexylphenyl)-3-(3-hydroxymethyl-4-trifluoromethoxyphenyl)ureidomethyl]benzoylamino}propionic acid,
3-{4-[1-(4-cyclohex-1-enylphenyl)-3-(3-hydroxymethyl-4-trifluoromethoxyphenyl)ureidomethyl]benzoylamino}propionic acid,
3-{4-[1-(4-cyclohexylphenyl)-3-(3-methylthiophenyl)ureidomethyl]benzoylamino}propionic acid,
3-{4-[1-(4-cyclohex-1-enylphenyl)-3-(3-methylthiophenyl)ureidomethyl]benzoylamino}propionic acid,
3-{4-[1-(4-cyclohexylcyclohexyl)-3-(3-methylthiophenyl)ureidomethyl]benzoylamino}propionic acid,
3-{4-[1-(4-cyclohexylcyclohexyl)-3-(3-iodophenyl)ureidomethyl]benzoylamino}propionic acid,
3-{4-[1-(4-cyclohexylphenyl)-3-(3-iodophenyl)ureidomethyl]benzoylamino}propionic acid,
3-{4-[1-(4-cyclohex-1-enylphenyl)-3-(3-iodophenyl)ureidomethyl]benzoylamino}propionic acid,
3-{4-[1-(4-cyclohexylphenyl)-3-(3-methylsulfonyl-4-butoxyphenyl)ureidomethyl]benzoylamino}propionic acid,
3-{4-[1-(4-cyclohex-1-enylphenyl)-3-(3-methylsulfonyl-4-butoxyphenyl)ureidomethyl]benzoylamino}propionic acid,
3-{4-[1-(4-cyclohexylcyclohexyl)-3-(3-methylsulfonyl-4-butoxyphenyl)ureidomethyl]benzoylamino}propionic acid,
3-{4-[1-(4-cyclohexylcyclohexyl)-3-(2-butyl-1,3-dioxo-2,3-dihydro-1H-isoindol-5-yl)ureidomethyl]benzoylamino}propionic acid,
3-{4-[1-(4-cyclohex-1-enylphenyl)-3-(2-butyl-1,3-dioxo-2,3-dihydro-1H-isoindol-5-yl)ureidomethyl]benzoylamino}propionic acid,
3-{4-[1-(4-cyclohexylphenyl)-3-(3-isopropyl-[1,2,4]oxadiazol-5-ylphenyl)ureidomethyl]benzoylamino}propionic acid,
3-{4-[1-(4-cyclohex-1-enylphenyl)-3-(3-isopropyl-[1,2,4]-oxadiazol-5-ylphenyl)ureidomethyl]benzoylamino}propionic acid,
3-{4-[3-[1(S)-(4-chlorophenyl)ethyl]-1-(4-cyclohexylphenyl)ureidomethylbenzoylamino}propionic acid,
3-{4-[1-(4-cyclohexylcyclohexyl)-3-(3-isopropyl-[1,2,4]oxadiazol-5-ylphenyl)ureidomethyl]benzoylamino}propionic acid,
3-{4-[3-[1(S)-(4-chlorophenyl)ethyl]-1-(4-cyclohexylcyclohexyl)ureidomethylbenzoylamino}propionic acid,
3-{4-[3-[1(S)-(4-chlorophenyl)ethyl]-1-(4-cyclohex-1-enylphenyl)ureidomethylbenzoylamino}propionic acid,
3-{4-[1-(4-cyclohexylphenyl)-3-(3-methylphenylsulfamoylphenyl)ureidomethyl]benzoylamino}propionic acid,
3-{4-[1-(4-cyclohex-1-enylphenyl)-3-(3-methylphenylsulfamoylphenyl)ureidomethyl]benzoylamino}propionic acid,
3-{4-[1-(4-cyclohexylcyclohexyl)-3-(3-methylphenylsulfamoylphenyl)ureidomethyl]benzoylamino]propionic acid,
3-{4-[1-(4-cyclohexylcyclohexyl)-3-(3-ethylphenylsulfamoylphenyl)ureidomethyl]benzoylamino}propionic acid,
3-{4-[1-(4-cyclohex-1-enylphenyl)-3-(3-ethylphenylsulfamoylphenyl)ureidomethyl]benzoylamino}propionic acid,
3-{4-[1-(4-cyclohexylphenyl)-3-(3-methylphenylsulfamoyl-4-methylphenyl)ureidomethyl]benzoylamino}propionic acid,
3-{4-[1-(4-cyclohex-1-enylphenyl)-3-(3-methylphenylsulfamoyl-4-methylphenyl)ureidomethyl]benzoylamino}propionic acid,
3-{4-[1-(4-cyclohex-1-enylphenyl)-3-(2-isopropyl-1,3-dioxo-2,3-dihydro-1H-isoindol-5-yl)ureidomethyl]benzoylamino}propionic acid,
3-{4-[1-(4-cyclohexylcyclohexyl)-3-(3-methylphenylsulfamoyl-4-methylphenyl)ureidomethyl]benzoylamino}propionic acid,
3-{4-[1-(4-cyclohexylcyclohexyl)-3-(2-isopropyl-1,3-dioxo-2,3-dihydro-1H-isoindol-5-yl)ureidomethyl]benzoylamino}propionic acid,
3-{4-[1-(4-cyclohexylphenyl)-3-(3-ethylphenylsulfamoyl-4-methylphenyl)ureidomethyl]benzoylamino}propionic acid,
3-{4-[1-(4-cyclohex-1-enylphenyl)-3-(3-ethylphenylsulfamoyl-4-methylphenyl)ureidomethyl]benzoylamino}propionic acid,
3-{4-[1-(4-cyclohexylphenyl)-3-(2-[2,2,2-trifluoroethyl]-1,3-dioxo-2,3-dihydro-1H-isoindol-5-yl)ureidomethyl]benzoylamino}propionic acid,
3-{4-[1-(4-cyclohex-1-enylphenyl)-3-(2-[2,2,2-trifluoroethyl]-1,3-dioxo-2,3-dihydro-1H-isoindol-5-yl)ureidomethyl]benzoylamino}propionic acid,
3-{4-[1-(4-cyclohexylcyclohexyl)-3-(2-[2,2,2-trifluoroethyl]-1,3-dioxo-2,3-dihydro-1H-isoindol-5-yl)ureidomethyl]benzoylamino}propionic acid, 3-{4-[1-(4-cyclohexylcyclohexyl)-3-(5-methylsulfonylthiophen-2-yl)ureidomethyl]benzoylamino}propionic acid, 3-{4-[1-(4-cyclohexylphenyl)-3-(5-methylsulfonylthiophen-2-yl)ureidomethyl]benzoylamino}propionic acid, 3-{4-[1-(4-cyclohex-1-enylcyclohexyl)-3-(5-methylsulfonylthiophen-2-yl)ureidomethyl]benzoylamino}propionic acid, 3-{4-[3-biphenyl-2-ylmethyl-1-(4-cyclohexylphenyl)ureidomethyl]benzoylamino}propionic acid, 3-{4-[3-biphenyl-2-ylmethyl-1-(4-cyclohex-1-enylphenyl)ureidomethyl]benzoylamino}propionic acid, 3-{4-[1-(4-cyclohex-1-enylphenyl)-3-(3-trifluoromethyl-4-chlorophenyl)ureidomethyl]benzoylamino}propionic acid, 3-{4-[1-(4-cyclohexylphenyl)-3-(2,2,4,4-tetrafluorobenzo[1,3]dioxin-6-yl)ureidomethyl]benzoylamino}propionic acid, 3-{4-[1-(4-cyclohexylcyclohexyl-3-(3-trifluoromethyl-4-chlorophenyl)ureidomethyl]benzoylamino}propionic acid, 3-{4-[1-(4-cyclohexylcyclohexyl)-3-(2,2,4,4-tetrafluorobenzo[1,3]dioxin-6-yl)ureidomethyl]benzoylamino}propionic acid, 3-{4-[1-(4-cyclohex-1-enylphenyl)-3-(2,2,4,4-tetrafluorobenzo[1,3]dioxin-6-yl)ureidomethyl]benzoylamino}propionic acid, 3-{4-[1-(4-cyclohexylphenyl)-3-(3,3,4,4-tetrafluorobenzo[1,4]dioxin-6-yl)ureidomethyl]benzoylamino}propionic acid, 3-{4-[1-(4-cyclohex-1-enylphenyl)-3-(3,3,4,4-tetrafluorobenzo[1,4]dioxin-6-yl)ureidomethyl]benzoylamino}propionic acid, 3-{4-[1-(4-cyclohexylphenyl)-3-(3-benzothiazol-2-yl-4-trifluoromethoxyphenyl)ureidomethyl]benzoylamino}propionic acid, 3-{4-[1-(4-cyclohexylcyclohexyl)-3-(3,3,4,4-tetrafluorobenzo[1,4]dioxin-6-yl)ureidomethyl]benzoylamino}propionic acid, 3-{4-[1-(4-cyclohexylcyclohexyl)-3-(3-fluorophenyl)ureidomethyl]benzoylamino}propionic acid, 3-{4-[1-(4-cyclohexylphenyl)-3-(3-fluorophenyl)ureidomethyl]benzoylamino}propionic acid, 3-{4-[1-(4-cyclohex-1-enylphenyl)-3-(3-fluorophenyl)ureidomethyl]benzoylamino}propionic acid, 3-{4-[1-(4-cyclohexylphenyl)-3-(3-methylphenyl)ureidomethyl]benzoylamino}propionic acid, 3-{4-[1-(4-cyclohex-1-enylphenyl)-3-(3-methylphenyl)ureidomethyl]benzoylamino}propionic acid, 3-{4-[1-(4-cyclohexylcyclohexyl)-3-(3-methylphenyl)ureidomethyl]benzoylamino}propionic acid, 3-{4-[1-(4-cyclohexylcyclohexyl)-3-(3-ethylphenyl)ureidomethyl]benzoylamino}propionic acid, 3-{4-[1-(4-cyclohexylphenyl)-3-(3-ethylphenyl)ureidomethyl]benzoylamino}propionic acid, 3-{4-[1-(4-cyclohex-1-enylphenyl)-3-(3-ethylphenyl)ureidomethyl]benzoylamino}propionic acid, 3-{4-[1-(4-cyclohex-1-enylphenyl)-3-(3-nitrophenyl)ureidomethyl]benzoylamino}propionic acid, 3-{4-[1-(4-cyclohex-1-enylphenyl)-3-(3-nitro-4-methylphenyl)ureidomethyl]benzoylamino}propionic acid, 3-{4-[1-(4-cyclohexylcyclohexyl)-3-(3-nitrophenyl)ureidomethyl]benzoylamino}propionic acid, 3-{4-[1-(4-cyclohexylcyclohexyl)-3-(3-nitro-4-methylphenyl)ureidomethyl]benzoylamino}propionic acid, 3-{4-[1-(4-cyclohexylphenyl)-3-(3-nitro-4-methylphenyl)ureidomethyl]benzoylamino}propionic acid, 3-{4-[1-(4-cyclohexylphenyl)-3-(3-cyanophenyl)ureidomethyl]benzoylamino}propionic acid, 3-{4-[1-(4-cyclohex-1-enylphenyl)-3-(3-cyanophenyl)ureidomethyl]benzoylamino}propionic acid, 3-{4-[1-(4-cyclohexylphenyl)-3-(3-phenoxyphenyl)ureidomethyl]benzoylamino}propionic acid, 3-{4-[1-(4-cyclohexylcyclohexyl)-3-(3-cyanophenyl)ureidomethyl]benzoylamino}propionic acid, 3-{4-[1-(4-cyclohexylcyclohexyl)-3-(3-phenoxyphenyl)ureidomethyl]benzoylamino}propionic acid, 3-{4-[1-(4-cyclohex-1-enylphenyl)-3-(3-phenoxyphenyl)ureidomethyl]benzoylamino}propionic acid, 3-{4-[1-(4-cyclohexylphenyl)-3-(3,5-difluorophenyl)ureidomethyl]benzoylamino}propionic acid, 3-{4-[1-(4-cyclohex-1-enylphenyl)-3-(3,5-difluorophenyl)ureidomethyl]benzoylamino}propionic acid, 3-{4-[1-(4-cyclohexylcyclohexyl)-3-(3,5-difluorophenyl)ureidomethyl]benzoylamino}propionic acid, 3-{4-[1-(4-cyclohexylphenyl)-3-trifluoromethoxybenzothiazol-2-yl)ureidomethyl]benzoylamino}propionic acid, 3-{4-[1-(4-cyclohexy-1-enylphenyl)-3-(6-trifluoromethoxybenzothiazol-2-yl)ureidomethyl]benzoylamino}propionic acid, 3-{4-[1-(4-cyclohexylphenyl)-3-(5-trifluoromethoxybenzothiazol-2-yl)ureidomethyl]benzoylamino}propionic acid, 3-{4-[1-(4-cyclohex-1-enylphenyl)-3-(5-trifluoromethoxybenzothiazol-2-yl)ureidomethyl]benzoylamino}propionic acid, 3-{4-[1-(4-cyclohex-1-enylphenyl)-3-(5,7-dichlorobenzothiazol-2-yl)ureidomethyl]benzoylamino}propionic acid, 3-{4-[1-(4-cyclohexylphenyl)-3-(5,7-dichlorobenzothiazol-2-yl)ureidomethyl]benzoylamino}propionic acid, 3-{4-[1-(4-cyclohexylphenyl)-3-(4,6-dichlorobenzothiazol-2-yl)ureidomethyl]benzoylamino}propionic acid, 3-{4-[1-(4-cyclohexenylphenyl)-3-(5-fluoro-7-trifluoromethylbenzothiazol-2-yl)ureidomethyl]benzoylamino}propionic acid, 3-{4-[1-(4-cyclohex-1-enylphenyl)-3-(4,6-dichlorobenzothiazol-2-yl)ureidomethyl]benzoylamino}propionic acid, 3-{4-[1-(4-cyclohex-1-enylphenyl)-3-(5-trifluoromethyl-7-methoxybenzothiazol-2-yl)ureidomethyl]benzoylamino}propionic acid, 3-{4-[1-(4-cyclohex-1-enylphenyl)-3-(5-fluoro-7-trifluoromethylbenzothiazol-2-yl)ureidomethyl]benzoylamino}propionic acid, 3-{4-[1-(4-cyclohexenylphenyl)-3-(4-trifluoromethoxybenzothiazol-2-yl)ureidomethyl]benzoylamino}propionic acid, 3-{4-[1-(4-cyclohex-1-enylphenyl)-3-(4-trifluoromethoxybenzothiazol-2-yl)ureidomethyl]benzoylamino}propionic acid, 3-{4-[1-(4-cyclohexylphenyl)-3-(7-trifluoromethoxybenzothiazol-2-yl)ureidomethyl]benzoylamino}propionic acid, 3-{4-[1-(4-cyclohex-1-enylphenyl)-3-(7-trifluoromethoxybenzothiazol-2-yl)ureidomethyl]benzoylamino}propionic acid, 3-{4-[1-(4-cyclohexylphenyl)-3-(4-fluoro-6-trifluoromethylbenzothiazol-2-yl)ureidomethyl]benzoylamino}propionic acid, 3-{4-[1-(4-cyclohex-1-enylphenyl)-3-(4-fluoro-6-trifluoromethylbenzothiazol-2-yl)ureidomethyl]benzoylamino}propionic acid, 3-{4-[1-(4-cyclohexylphenyl)-3-(5,6-dichlorobenzothiazol-2-yl)ureidomethyl]benzoylamino}propionic acid, 3-{4-[1-(4-cyclohexylphenyl)-3-(5-bromobenzothiazol-2-yl)ureidomethyl]benzoylamino}propionic acid, 3-{4-[1-(4-cyclohexylphenyl)-3-(5-bromo-7-fluorobenzothiazol-2-yl)ureidomethyl]benzoylamino}propionic acid, 3-{4-[1-(4-cyclohex-1-enylphenyl)-3-(5-bromo-7-fluorobenzothiazol-2-yl)ureidomethyl]benzoylamino}propionic acid, 3-{4-[1-(4-cyclohex-1-enylphenyl)-3-(5-bromobenzothiazol-2-yl)ureidomethyl]benzoylamino}propionic acid, 3-{4-[1-(4-cyclohex-1-enylphenyl)-3-(5-trifluoromethylbenzothiazol-2-yl)ureidomethyl]benzoylamino}propionic acid, 3-{4-[1-(4-cyclohex-1-enylphenyl)-3-(5,7-bis(trifluoromethyl)benzothiazol-2-yl)ureidomethyl]benzoylamino}propionic acid, 3-{4-[1-(4-cyclohexylphenyl)-3-(5-trifluoromethylbenzothiazol-2-yl)ureidomethyl]benzoylamino}propionic acid, 3-{4-[1-(4-cyclohexylphenyl)-3-(5,7-bis(trifluoromethyl)benzothiazol-2-yl)ureidomethyl]benzoylamino}propionic acid, 3-{4-[1-(4-cyclohexylphenyl)-3-(6,6,8,8-tetrafluoro-6H-dioxino[5,4-f]benzothiazol-2-yl)ureidomethyl]benzoylamino}propionic acid, 3-{4-[1-(4-cyclohex-1-enylphenyl)-3-(6,6,8,8-tetrafluoro-6H-dioxino[5,4-f]benzothiazol-2-yl)ureidomethyl]benzoylamino}propionic acid, 3-{4-[1-(4-cyclohex-1-enylphenyl)-3-(5,6,-(tetrafluoroethylenedioxo)benzothiazol-2-yl)ureidomethyl]benzoylamino}propionic acid, 3-{4-[1-(4-cyclohex-1-enylphenyl)-3-(5-fluoro-6-trifluoroethylbenzothiazol-2-yl)ureidomethyl]benzoylamino}propionic acid, 3-{4-[1-(4-cyclohexylphenyl)-3-(5-fluoro-6-trifluoromethylbenzothiazol-2-yl)ureidomethyl]benzoylamino}propionic acid, 3-{4-[1-(4-cyclohexylphenyl)-3-(6,7-(tetrafluoroethylenedioxo)benzothiazol-2-yl)ureidomethyl]benzoylamino}propionic acid, 3-{4-[1-(4-cyclohex-1-enylphenyl)-3-(6,7-(tetrafluoroethylenedioxo)benzothiazol-2-yl)ureidomethyl]benzoylamino}propionic acid, 3-{4-[1-(4-cyclohex-1-enylphenyl)-3-(6-trifluoromethylthiobenzothiazol-2-yl)ureidomethyl]benzoylamino}propionic acid, 3-{4-[1-(4-cyclohexylphenyl)-3-(6-trifluoromethylthiobenzothiazol-2-yl)ureidomethyl]benzoylamino}propionic acid, 3-{4-[1-(4-cyclohexylphenyl)-3-(6,7-dichlorobenzothiazol-2-yl)ureidomethyl]benzoylamino}propionic acid, 3-{4-[1-(4-cyclohex-1-enylphenyl)-3-(6,7-dichlorobenzothiazol-2-yl)ureidomethyl]benzoylamino}propionic acid, 3-{4-[1-(4-cyclohexylphenyl)-3-(5-trifluoromethylthiobenzothiazol-2-yl)ureidomethyl]benzoylamino}propionic acid, 3-{4-[1-(4-cyclohex-1-enylphenyl)-3-(5-trifluoromethyl-6-cyanobenzothiazol-2-yl)ureidomethyl]benzoylamino}propionic acid, 3-{4-[1-(4-cyclohexylphenyl)-3-(5-trifluoromethyl-6-cyanobenzothiazol-2-yl)ureidomethyl]benzoylamino}propionic acid, 3-{4-[1-(4-cyclohexylphenyl)-3-(5-trifluoromethyl-7-methylbenzothiazol-2-yl)ureidomethyl]benzoylamino}propionic acid, 3-{4-[1-(4-cyclohex-1-enylphenyl)-3-(5-trifluoromethyl-7-methylbenzothiazol-2-yl)ureidomethyl]benzoylamino}propionic acid, 3-{4-[1-(4-cyclohex-1-enylphenyl)-3-(5-trifluoromethyl-7-cyanobenzothiazol-2-yl)ureidomethyl]benzoylamino}propionic acid, 3-{4-[1-(4-cyclohexylphenyl)-3-(5-trifluoromethyl-7-cyanobenzothiazol-2-yl)ureidomethyl]benzoylamino}propionic acid, 3-{4-[1-(4-cyclohexenylphenyl)-3-(5-trifluoromethyl-6-bromobenzothiazol-2-yl)ureidomethyl]benzoylamino}propionic acid, 3-{4-[1-(4-cyclohex-1-enylphenyl)-3-(5-trifluoromethyl-6-bromobenzothiazol-2-yl)ureidomethyl]benzoylamino}propionic acid, 3-{4-[1-(4-cyclohex-1-enylphenyl)-3-(5-tert-butylbenzothiazol-2-yl)ureidomethyl]benzoylamino}propionic acid, 3-{4-[1-(4-cyclohexylphenyl)-3-(5-tert-butylbenzothiazol-2-yl)ureidomethyl]benzoylamino}propionic acid, 3-{4-[1-(4-cyclohexylphenyl)-3-(5-trifluoromethyl-7-methoxybenzothiazol-2-yl)ureidomethyl]benzoylamino}propionic acid, 3-{4-[1-(4-cyclohexylphenyl)-3-(3-methylsulfonyl-4-methylphenyl)ureidomethyl]benzoylamino}propionic acid, 3-{4-[1-(4-cyclohex-1-enylphenyl)-3-(3-methylsulfonyl-4-methylphenyl)ureidomethyl]benzoylamino}propionic acid, 3-{4-[1-(4-cyclohexylphenyl)-3-(3-ethylthiophenyl)ureidomethyl]benzoylamino}propionic acid, 3-{4-[1-(4-cyclohex-1-enylphenyl)-3-(3-ethylthiophenyl)ureidomethyl]benzoylamino}propionic acid, 3-{4-[1-(4-cyclohexylphenyl)-3-(3-acetylphenyl)ureidomethyl]benzoylamino}propionic acid, 3-{4-[1-(4-cyclohex-1-enylphenyl)-3-(3-acetylphenyl)ureidomethyl]benzoylamino}propionic acid, 3-{4-[1-(4-cyclohexylphenyl)-3-(3-chloro-4-cyanophenyl)ureidomethyl]benzoylamino}propionic acid, 3-{4-[1-(4-cyclohex-1-enylphenyl)-3-(3-chloro-4-cyanophenyl)ureidomethyl]benzoylamino}propionic acid, 3-{4-[1-(4-cyclohexylphenyl)-3-(3-chloro-4-bromophenyl)ureidomethyl]benzoylamino}propionic acid, 3-{4-[1-(4-cyclohex-1-enylphenyl)-3-(3-chloro-4-bromophenyl)ureidomethyl]benzoylamino}propionic acid, 3-{4-[1-(4-cyclohexylphenyl)-3-(2-methyl-1,3-dioxo-2,3-dihydro-1H-isoindol-5-yl)ureidomethyl]benzoylamino}propionic acid, 3-{4-[1-(4-cyclohex-1-enylphenyl)-3-(2-methyl-1,3-dioxo-2,3-dihydro-1H-isoindol-5-yl)ureidomethyl]benzoylamino}propionic acid, 3-{4-[1-(4-cyclohexylphenyl)-3-(3-benzooxazol-2-yl-4-trifluoromethoxyphenyl)ureidomethyl]benzoylamino}propionic acid, 3-{4-[1-(4-cyclohex-1-enylphenyl)-3-(3-benzooxazol-2-yl-4-trifluoromethoxyphenyl)ureidomethyl]benzoylamino}propionic acid, 3-{4-[1-(4-cyclohexylphenyl)-3-(3-(2-methyl-2H-tetrazol-5-yl)phenyl)ureidomethyl]benzoylamino}propionic acid, 3-{4-[1-(4-cyclohex-1-enylphenyl)-3-(3-(2-methyl-2H-tetrazol-5-yl)phenyl)ureidomethyl]benzoylamino}propionic acid, and 3-{4-[3-(3-cyano-5-trifluoromethylphenyl)-1-(4-cyclohex-1-enylphenyl)ureidomethyl]benzoylamino}propionic acid or any optical or geometric isomer or tautomeric form thereof including mixtures of these or a pharmaceutically acceptable salt thereof.

2. A compound which is selected from

3-{4-[1-(4-cyclohexylphenyl)-3-(3-trifluoromethoxyphenyl)ureidomethyl]benzoylamino}propionic acid, 3-{4-[1-(4-cyclohex-1-enylphenyl)-3-(3-trifluoromethoxyphenyl)ureidomethyl]benzoylamino}propionic acid, 3-{4-[1-(4-cyclohexylphenyl)-3-(3-trifluoromethylphenyl)ureidomethyl]benzoylamino}propionic acid, 3-{4-[1-(4-cyclohexylphenyl)-3-(3-bromophenyl)ureidomethyl]benzoylamino}propionic acid, 3-{4-[1-(4-cyclohex-1-enylphenyl)-3-(3-bromophenyl)ureidomethyl]benzoylamino}propionic acid, 3-{4-[1-(4-cyclohexylphenyl)-3-(3-trifluoromethyl-5-fluorophenyl)ureidomethyl]benzoylamino}propionic acid, 3-{4-[1-(4-cyclohexylphenyl)-3-(3-trifluoromethyl-5-cyanophenyl)ureidomethyl]benzoylamino}propionic acid, 3-{4-[1-(4-cyclohex-1-enylphenyl)-3-(3-methylsulfonyl-4-trifluoromethoxyphenyl)ureidomethyl]benzoylamino}propionic acid, 3-{4-[1-(4-cyclohexylphenyl)-3-(3-hydroxymethyl-4-trifluoromethoxyphenyl)ureidomethyl]benzoylamino}propionic acid, 3-{4-[1-(4-cyclohex-1-enylphenyl)-3-(3-hydroxymethyl-4-trifluoromethoxyphenyl)ureidomethyl]benzoylamino}propionic acid, 3-{4-[1-(4-cyclohexylphenyl)-3-(3-methylthiophenyl)ureidomethyl]benzoylamino}propionic acid, 3-{4-[1-(4-cyclohex-1-enylphenyl)-3-(3-methylthiophenyl)ureidomethyl]benzoylamino}propionic acid, 3-{4-[3-[1(S)-(4-Chlorophenyl)ethyl]-1-(4cyclohexylphenyl)ureidomethyl]benzoylamino}propionic acid, 3-{4-[3-biphenyl-2-ylmethyl-1-(4-cyclohexylphenyl)ureidomethyl]benzoylamino}propionic acid, 3-{4-[1-(4-cyclohexylphenyl)-3-(2,2,4,4-tetrafluorobenzo[1,3]dioxin-6-yl)ureidomethyl]benzoylamino}propionic acid, 3-{4-[1-(4-cyclohex-1-enylphenyl)-3-(2,2,4,4-tetrafluorobenzo[1,3]dioxin-6-yl)ureidomethyl]benzoylamino}propionic acid, 3-{4-[1-(4-cyclohexylphenyl)-3-(3,3,4,4-tetrafluorobenzo[1,4]dioxin-6-yl)ureidomethyl]benzoylamino}propionic acid, 3-{4-[1-(4-cyclohex-1-enylphenyl)-3-(3,3,4,4-tetrafluorobenzo[1,4]dioxin-6-yl)ureidomethyl]benzoylamino}propionic acid, 3-{4-[1-(4-cyclohex-1-enylphenyl)-3-(6-trifluoromethoxybenzothiazol-2-yl)ureidomethyl]benzoylamino}propionic acid, 3-{4-[3-(3-cyano-5-trifluoromethylphenyl)-1-(4-cyclohex-1-enylphenyl)ureidomethyl]benzoylamino}propionic acid, or any optical or geometric isomer or tautomeric form thereof including mixtures of these or a pharmaceutically acceptable salt thereof.

3. A compound which is selected from

3-{4-[1-(4-cyclohexylphenyl)-3-(3-trifluoromethoxyphenyl)ureidomethyl]benzoylamino}propionic acid, 3-{4-[1-(4-cyclohex-1-enylphenyl)-3-(3-trifluoromethoxyphenyl)ureidomethyl]benzoylamino}propionic acid, 3-{4-[1-(4-cyclohexylcyclohexyl)-3-(3-trifluoromethoxyphenyl)ureidomethyl]benzoylamino}propionic acid, 3-{4-[1-(4-cyclohexylcyclohexyl)-3-(3-trifluoromethylphenyl)ureidomethyl]benzoylamino}propionic acid, 3-{4-[1-(4-cyclohexylphenyl)-3-(3-trifluoromethylphenyl)ureidomethyl]benzoylamino}propionic acid, 3-{4-[1-(4-cyclohexylphenyl)-3-(3-bromophenyl)ureidomethyl]benzoylamino}propionic acid, 3-{4-[1-(4-cyclohex-1-enylphenyl)-3-(3-bromophenyl)ureidomethyl]benzoylamino}propionic acid, 3-{4-[1-(4-cyclohexylphenyl)-3-(3-trifluoromethyl-5-fluorophenyl)ureidomethyl]benzoylamino}propionic acid, 3-{4-[1-(4-cyclohexylcyclohexyl)-3-(3-bromophenyl)ureidomethyl]benzoylamino}propionic acid, 3-{4-[1-(4-cyclohexylphenyl)-3-(3-trifluoromethyl-5-fluorophenyl)ureidomethyl]benzoylamino}propionic acid, 3-{4-[1-(4-cyclohexylphenyl)-3-(3-trifluoromethyl-5-cyanophenyl)ureidomethyl]benzoylamino}propionic acid, 3-{4-[1-(4-cyclohexylphenyl)-3-(3-chlorophenyl)ureidomethyl]benzoylamino}propionic acid, 3-{4-[1-(4-cyclohexylcyclohexyl)-3-(3-trifluoromethyl-5-cyanophenyl)ureidomethyl]benzoylamino}propionic acid, 3-{4-[1-(4-cyclohexylcyclohexyl)-3-(3-chlorophenyl)ureidomethyl]benzoylamino}propionic acid, 3-{4-[1-(4-cyclohex1-enylphenyl)-3-(3-chlorophenyl)ureidomethyl]benzoylamino}propionic acid, 3-{4-[1-(4-cyclohexylphenyl)-3-(3-methylsulfonyl-4-trifluoromethoxyphenyl)ureidomethyl]-benzoylamino}propionic acid, 3-{4-[1-(4-cyclohexylcyclohexyl)-3-(3-methylsulfonyl-4-trifluoromethoxyphenyl)ureidomethyl]-benzoylamino}propionic acid, 3-{4-[1-(4-cyclohexylcyclohexyl)-3-(3-methylsulfonylphenyl)ureidomethyl]benzoylamino}propionic acid, 3-{4-[1-(4-cyclohex-1-enylphenyl)-3-(3-methylsulfonyl-4-trifluoromethoxyphenyl)ureidomethyl]-benzoylamino}propionic acid, 3-{4-[1-(4-cyclohex-1-enylphenyl)-3-(3-methylsulfonylphenyl)ureidomethyl]benzoylamino}propionic acid, 3-{4-[1-(4-cyclohexylphenyl)-3-(3-tert-butylphenyl)ureidomethyl]benzoylamino}propionic acid, 3-{4-[1-(4-cyclohex-1-enylphenyl)-3-(3-tert-butylphenyl)ureidomethyl]benzoylamino}propionic acid, 3-{4-[1-(4-cyclohexylcyclohexyl)-3-(3-tert-butylphenyl)ureidomethyl]benzoylamino}propionic acid, 3-{4-[1-(4-cyclohexylcyclohexyl)-3-(3-hydroxymethyl-4-trifluoromethoxyphenyl)ureidomethyl]-benzoylamino}propionic acid, 3-{4-[1-(4-cyclohexylphenyl)-3-(3-hydroxymethyl-4-trifluoromethoxyphenyl)ureidomethyl]-benzoylamino}propionic acid, 3-{4-[1-(4-cyclohex-1-enylphenyl)-3-(3-hydroxymethyl-4-trifluoromethoxyphenyl)ureidomethyl]benzoylamino}propionic acid, 3-{4-[1-(4-cyclohexylphenyl)-3-(3-methylthiophenyl)ureidomethyl]benzoylamino}propionic acid, 3-[4-[1-(4-cyclohex-1-enylphenyl)-3-(3-methylthiophenyl)ureidomethyl]benzoylamino}propionic acid, 3-{4-[1-(4-cyclohexylcyclohexyl)-3-(3-methylthiophenyl)ureidomethyl]benzoylamino}propionic acid, 3-{4-[1-(4-cyclohexylcyclohexyl)-3-(3-iodophenyl)ureidomethyl]benzoylamino}propionic acid, 3-{4-[1-(4-cyclohexylphenyl)-3-(3-iodophenyl)ureidomethyl]benzoylamino}propionic acid, 3-{4-[1-(4-cyclohex-1-enylphenyl)-3-(3-iodophenyl)ureidomethyl]benzoylamino}propionic acid, 3-{4-[1-(4-cyclohexylphenyl)-3-(3-[methylsulfonyl] methylsulfonyl-4-butoxyphenyl)ureidomethyl]benzoylamino}propionic acid, 3-{4-[1-(4-cyclohex-1-enylphenyl)-3-(3-[methylsulfonyl] methylsulfonyl-4-butoxyphenyl)ureidomethyl]benzoylamino}propionic acid, 3-{4-[1-(4-cyclohexylcyclohexyl)-3-(3-[methylsulfonyl] methylsulfonyl -4-butoxyphenyl)ureidomethyl]benzoylamino}propionic acid, 3-[4-[1-(4-cyclohexylcyclohexyl)-3-(2-butyl-1,3-dioxo-2,3-dihydro-1H-isoindol-5-yl)ureidomethyl]benzoylamino}propionic acid, 3-{4-[1-(4-cyclohex-1-enylphenyl)-3-(2-butyl-1,3-dioxo-2,3-dihydro-1H-isoindol-5-yl)ureidomethyl]benzoylamino}propionic acid, 3-{4-[1-(4-cyclohexylphenyl)-3-(3-isopropyl-[1,2,4]oxadiazol-5-ylphenyl)ureidomethyl]benzoylamino}propionic acid, 3-{4-[1-(4-cyclohex-1-enylphenyl)-3-(3-isopropyl-[1,2,4]oxadiazol-5-ylphenyl)ureidomethyl]-benzoylamino}propionic acid, 3-{4-[3-[1(S)-(4-chlorophenyl)ethyl]-1-(4-cyclohexylphenyl)ureidomethylbenzoylamino}propionic acid, 3-{4-[1-(4-cyclohexylcyclohexyl)-3-(3-isopropyl-[1,2,4]oxadiazol-5-ylphenyl)ureidomethyl]benzoylamino}propionic acid, 3-{4-[3-[1(S)-(4-chlorophenyl)ethyl]-1-(4-cyclohexylcyclohexyl)ureidomethylbenzoylamino}propionic acid, 3-{4-[3-[1(S)-(4-chlorophenyl)ethyl]-1-(4-cyclohex-1-enylphenyl)ureidomethylbenzoylamino}propionic acid, 3-{4-[1-(4-cyclohexylphenyl)-3-(3-methylphenylsulfamoylphenyl)ureidomethyl]benzoylamino}propionic acid, 3-{4-[1-(4-cyclohex-1-enylphenyl)-3-(3-methylphenylsulfamoylphenyl)ureidomethyl]benzoylamino}propionic acid, 3-{4-[1-(4-cyclohexylphenyl)-3-(3-ethylphenylsulfamoylphenyl)ureidomethyl]benzoylamino}propionic acid, 3-{4-[1-(4-cyclohexylcyclohexyl)-3-(3-methylphenylsulfamoylphenyl)ureidomethyl]benzoylamino}propionic acid, 3-{4-[1-(4-cyclohexylcyclohexyl)-3-(3-ethylphenylsulfamoylphenyl)ureidomethyl]benzoylamino}propionic acid, 3-{4-[1-(4-cyclohex-1-enylphenyl)-3-(3-ethylphenylsulfamoylphenyl)ureidomethyl]benzoylamino}propionic acid, 3-{4-[1-(4-cyclohexylphenyl)-3-(3-methylphenylsulfamoyl-4-methylphenyl)ureidomethyl]benzoylamino}propionic acid, 3-{4-[1-(4-cyclohex-1-enylphenyl)-3-(3-methylphenylsulfamoyl-4-methylphenyl)ureidomethyl]benzoylamino}propionic acid, 3-{4-[1-(4-cyclohex-1-enylphenyl)-3-(2-isopropyl-1,3-dioxo-2,3-dihydro-1H-isoindol-5-yl)ureidomethyl]benzoylamino}propionic acid, 3-{4-[1-(4-cyclohexylcyclohexyl)-3-(3-methylphenylsulfamoyl-4-methylphenyl)ureidomethyl]benzoylamino}propionic acid, 3-{4-[1-(4-cyclohexylcyclohexyl)-3-(2-isopropyl-1,3-dioxo-2,3-dihydro-1H-isoindol-5-yl)ureidomethyl]benzoylamino}propionic acid, 3-{4-[1-(4-cyclohexylphenyl)-3-(3-ethylphenylsulfamoyl-4-methylphenyl)ureidomethyl]benzoylamino}propionic acid, 3-{4-[1-(4-cyclohex-1-enylphenyl)-3-(3-ethylphenylsulfamoyl-4-methylphenyl)ureidomethyl]benzoylamino}propionic acid, 3-{4-[1-(4-cyclohexylphenyl)-3(2-[2,2,2-trifluoroethyl]-1,3-dioxo-2,3-dihydro-1H-isoindol-5-yl)-ureidomethyl]benzoylamino}propionic acid, 3-{4-[1-(4-cyclohex-1-enylphenyl)-3-(2-(2,2,2-trifluoroethyl)-1,3-dioxo-2,3-dihydro-1H-isoindol-5-yl)ureidomethyl]benzoylamino}propionic acid, 3-{4-[1-(4-cyclohexylcyclohexyl)-3(2-[2,2,2trifluoroethyl]-1,3-dioxo-2,3-dihydro-1H-isoindol-5-yl)ureidomethyl]benzoylamino}propionic acid, 3-{4-[1(4-cyclohexylcyclohexyl)-3(5-methylsulfonylthiophen-2-yl)ureidomethyl]benzoylamino}propionic acid, 3-{4-[1-(4-cyclohexylphenyl)-3-(5-methylsulfonylthiophen-2-yl)ureidomethyl]benzoylamino}propionic acid, 3-{4-[1-(4-cyclohex-1-enylcyclohexyl)-3-(5-methylsulfonylthiophen-2-yl)ureidomethyl]benzoylamino}propionic acid, 3-{4-[3-biphenyl-2-ylmethyl-1-(4-cyclohexylphenyl)ureidomethyl]benzoylamino}propionic acid, 3-{4-[3-biphenyl-2-ylmethyl-1-(4-cyclohex-1-enylphenyl)ureidomethyl]benzoylamino}propionic acid, 3-{4-[1-(4-cyclohex-1-enylphenyl)-3-(3-trifluoromethyl-4-chlorophenyl)ureidomethyl]benzoylamino}propionic acid, 3-{4-[1-(4-cyclohexylphenyl)-3-(2,2,4,4-tetrafluorobenzo[1,3]dioxin-6-yl)ureidomethyl]benzoylamino}propionic acid, 3-{4-[1-(4-cyclohexylcyclohexyl)-3-(3-trifluoromethyl-4-chlorophenyl)ureidomethyl]benzoylamino}propionic acid, 3-{4-[1-(4-cyclohexylcyclohexyl)-3-(2,2,4,4-tetrafluorobenzo[1,3]dioxin-6-yl)ureidomethyl]benzoylamino}propionic acid, 3-{4-[1-(4-cyclohex-1-enylphenyl)-3-(2,2,4,4-tetrafluorobenzo[1,3]dioxin-6-yl)ureidomethyl]benzoylamino}propionic acid, 3-{4-[1-(4-cyclohexylphenyl)-3-(3,3,4,4,-tetrafluorobenzo[1,4]dioxin-6-yl)ureidomethyl]benzoylamino}propionic acid, 3-{4-[1-(4-cyclohex-1-enylphenyl)-3-(3,3,4,4-tetrafluorobenzo[1,4]dioxin-6-yl)ureidomethyl]benzoylamino}propionic acid, 3-{4-[1-(4-cyclohexylphenyl)-3-(3-benzothiazol 2-yl-4-trifluoromethoxyphenyl)ureidomethyl]benzoylamino}propionic acid, 3-{4-[1-(4-cyclohexylcyclohexyl)-3-(3,3,4,4-tetrafluorobenzo[1,4]dioxin-6-yl)ureidomethyl]benzoylamino}propionic acid, 3-{4-[1-(4-cyclohexylcyclohexyl)-3-(3-fluorophenyl)ureidomethyl]benzoylamino}propionic acid, 3-{4-[1-(4-cyclohexylphenyl)-3-(3-fluorophenyl)ureidomethyl]benzoylamino}propionic acid, 3-{4-[1-(4-cyclohex-1-enylphenyl)-3-(3-fluorophenyl)ureidomethyl]benzoylamino}propionic acid, 3-{4-[1-(4-cyclohexylphenyl)-3-(3-methylphenyl)ureidomethyl]benzoylamino}propionic acid, 3-{4-[1-(4-cyclohex-1-enylphenyl)-3-(3-methylphenyl)ureidomethyl]benzoylamino}propionic acid, 3-{4-[1-(4-cyclohexylcyclohexyl)-3-(3-methylphenyl)ureidomethyl]benzoylamino}propionic acid, 3-{4-[1-(4-cyclohexylcyclohexyl)-3-(3-ethylphenyl)ureidomethyl]benzoylamino}propionic acid, 3-{4-[1-(4-cyclohexylphenyl)-3-(3-ethylphenyl)ureidomethyl]benzoylamino}propionic acid, 3-{4-[1-(4-cyclohex-1-enylphenyl)-3-(3-ethylphenyl)ureidomethyl]benzoylamino}propionic acid, 3-{4-[1-(4-cyclohex-1-enylphenyl)-3-(3-nitrophenyl)ureidomethyl]benzoylamino}propionic acid, 3-{4-[1-(4-cyclohex-1-enylphenyl)-3-(3-nitro-4-methylphenyl)ureidomethyl]benzoylamino}propionic acid, 3-{4-[1-(4-cyclohexylcyclohexyl)-3-(3-nitrophenyl)ureidomethyl]benzoylamino}propionic acid, 3-{4-[1-(4-cyclohexylcyclohexyl)-3-(3-nitro-4-methylphenyl)ureidomethyl]benzoylamino}propionic acid, 3-{4-[1-(4-cyclohexylphenyl)-3-(3-nitro-4-methylphenyl)ureidomethyl]benzoylamino}propionic acid, 3-{4-[1-(4-cyclohexylphenyl)-3-(3-cyanophenyl)ureidomethyl]benzoylamino}propionic acid, 3-{4-[1-(4-cyclohex-1-enylphenyl)-3-(3-cyanophenyl)ureidomethyl]benzoylamino}propionic acid, 3-{4-[1-(4-cyclohexylphenyl)-3-(3-phenoxyphenyl)ureidomethyl]benzoylamino}propionic acid, 3-{4-[1-(4-cyclohexylcyclohexyl)-3-(3-cyanophenyl)ureidomethyl]benzoylamino}propionic acid, 3-{4-[1-(4-cyclohexylcyclohexyl)-3-(3-phenoxyphenyl)ureidomethyl]benzoylamino}propionic acid, 3-{4-[1-(4-cyclohex-1-enylphenyl)-3-(3-phenoxyphenyl)ureidomethyl]benzoylamino}propionic acid, 3-{4-[1-(4-cyclohexylphenyl)-3-(3,5-difluorophenyl)ureidomethyl]benzoylamino}propionic acid, 3-{4-[1-(4-cyclohex-1-enylphenyl)-3-(3,5-difluorophenyl)ureidomethyl]benzoylamino}propionic acid, 3-{4-[1-(4-cyclohexylcyclohexyl)-3-(3,5-difluorophenyl)ureidomethyl]benzoylamino}propionic acid, 3-{4-[1-(4-cyclohexylphenyl)-3-(6-trifluoromethoxybenzothiazol-2-yl)ureidomethyl]benzoylamino}propionic acid, 3-{4-[1-(4-cyclohex-1-enylphenyl)-3-(6-trifluoromethoxybenzothiazol-2-yl)ureidomethyl]benzoylamino}propionic acid, 3-{4-[1-(4-cyclohexylphenyl)-3-(5-trifluoromethoxybenzothiazol-2-yl)ureidomethyl]benzoylamino}propionic acid, 3-{4-[1-(4-cyclohex-1-enylphenyl)-3-(5-trifluoromethoxybenzothiazol-2-yl)ureidomethyl]benzoylamino}propionic acid, 3-{4-[1-(4-cyclohex-1-enylphenyl)-3-(5,7-dichlorobenzothiazol-2-yl)ureidomethyl]benzoylamino}propionic acid, 3-{4-[1-(4-cyclohexylphenyl)-3-(5,7-dichlorobenzothiazol-2-yl)ureidomethyl]benzoylamino}propionic acid, 3-{4-[1-(4-cyclohexylphenyl)-3-(4,6-dichlorobenzothiazol-2-yl)ureidomethyl]benzoylamino}propionic acid, 3-{4-[1-(4-cyclohexylphenyl)-3-(5-fluoro-7-trifluoromethylbenzothiazol-2-yl)ureidomethyl]benzoylamino}propionic acid, 3-{4-[1-(4-cyclohex-1-enylphenyl)-3-(4,6-dichlorobenzothiazol-2-yl)ureidomethyl]benzoylamino}propionic acid, 3-{4-[1-(4-cyclohex-1-enylphenyl)-3-(5-trifluoromethyl-7-methoxybenzothiazol-2-yl)ureidomethyl]benzoylamino}propionic acid, 3-{4-[1-(4-cyclohex-1-enylphenyl)-3-(5-fluoro-7-trifluoromethylbenzothiazol-2-yl)ureidomethyl]benzoylamino}propionic acid, 3-{4-[1-(4-cyclohexylphenyl)-3-(4-trifluoromethoxybenzothiazol-2-yl)ureidomethyl]benzoylamino}propionic acid, 3-{4-[1-(4-cyclohex-1-enylphenyl)-3-(4-trifluoromethoxybenzothiazol-2-yl)ureidomethyl]benzoylamino}propionic acid, 3-{4-[1-(4-cyclohexylphenyl)-3-(7-trifluoromethoxybenzothiazol-2-yl)ureidomethyl]benzoylamino}propionic acid, 3-{4-[1-(4-cyclohex-1-enylphenyl)-3-(7-trifluoromethoxybenzothiazol-2-yl)ureidomethyl]benzoylamino}propionic acid, 3-{4-[1-(4-cyclohexylphenyl)-3-(4-fluoro-6-trifluoromethylbenzothiazol-2-yl)ureidomethyl[benzoylamino}propionic acid, 3-{4-[1-(4-cyclohex-1-enylphenyl)-3-(4-fluoro-6-trifluoromethylbenzothiazol-2-yl)ureidomethyl]benzoylamino}propionic acid, 3-{4-[1-(4-cyclohexylphenyl)-3-(5,6-dichlorobenzothiazol-2-yl)ureidomethyl]benzoylamino}propionic acid, 3-{4-[1-(4-cyclohexylphenyl)-3-(5-bromobenzothiazol-2-yl)ureidomethyl]benzoylamino}propionic acid, 3-{4-[1-(4-cyclohexylphenyl)-3-(5-bromo-7-fluorobenzothiazol-2-yl)ureidomethyl]benzoylamino}propionic acid, 3-{4-[1-(4-cyclohex-1-enylphenyl)-3-(5-bromo-7-fluorobenzothiazol-2-yl)ureidomethyl]benzoylamino}propionic acid, 3-{4-[1-(4-cyclohex-1-enylphenyl)-3-(5-bromobenzothiazol-2-yl)ureidomethyl]benzoylamino}propionic acid, 3-{4-[1-(4-cyclohex-1-enylphenyl)-3-(5-trifluoromethylbenzothiazol-2-yl)ureidomethyl]benzoylamino}propionic acid, 3-{4-[1-(4-cyclohex-1-enylphenyl)-3-(5,7-bis(trifluoromethyl)benzothiazol-2-yl)ureidomethyl]benzoylamino}propionic acid, 3-{4-[1-(4-cyclohexylphenyl)-3-(5-trifluoromethylbenzothiazol-2-yl)ureidomethyl]benzoylamino}propionic acid, 3-{4-[1-(4-cyclohexylphenyl)-3-(5,7-bis(trifluoromethyl)benzothiazol-2-yl)ureidomethyl]benzoylamino}propionic acid, 3-{4-[1-(4-cyclohexylphenyl)-3-(6,6,8,8-tetrafluoro-6H-dioxino[5,4-f]benzothiazol-2-yl)ureidomethyl]benzoylamino}propionic acid, 3-{4-[1-(4-cyclohex-1-enylphenyl)-3-(6,6,8,8-tetrafluoro-6H-dioxino[5,4-f]benzothiazol-2-yl)ureidomethyl]benzoylamino}propionic acid, 3-{4-[1-(4-cyclohex-1-enylphenyl)-3-(5,6-(tetrafluoroethylenedioxo)benzothiazol-2-yl)ureidomethyl]benzoylamino}propionic acid, 3-{4-[1-(4-cyclohex-1-enylphenyl)-3-(5-fluoro-6-trifluoromethylbenzothiazol-2-yl)ureidomethyl]benzoylamino}propionic acid, 3-{4-[1-(4-cyclohexylphenyl)-3-(5-fluoro-6-trifluoromethylbenzothiazol-2-yl)ureidomethyl]benzoylamino}propionic acid, 3-{4-[1-(4-cyclohexylphenyl)-3-(6,7-(tetrafluoroethylenedioxo)benzothiazol-2-yl)ureidomethyl]benzoylamino}propionic acid, 3-{4-[1-(4-cyclohex-1-enylphenyl)-3-(6,7-(tetrafluoroethylenedioxo)benzothiazol-2-yl)ureidomethyl]benzoylamino}propionic acid, 3-{4-[1-(4-cyclohex-1-enylphenyl)-3-(6-trifluoromethylthiobenzothiazol-2-yl)ureidomethyl]benzoylamino}propionic acid, 3-{4-[1-(4-cyclohexylphenyl)-3-(6-trifluoromethylthiobenzothiazol-2-yl)ureidomethyl]benzoylamino}propionic acid, 3-{4-[1-(4-cyclohexylphenyl)-3-(6,7-dichlorobenzothiazol-2-yl)ureidomethyl]benzoylamino}propionic acid, 3-{4-[1-(4-cyclohex-1-enylphenyl)-3-(6,7-dichlorobenzothiazol-2-yl)ureidomethyl]benzoylamino}propionic acid, 3-{4-[1-(4-cyclohexylphenyl)-3-(5-trifluoromethylthiobenzothiazol-2-yl)ureidomethyl]benzoylamino}propionic acid, 3-{4-[1-(4-cyclohex-1-enylphenyl)-3-(5-trifluoromethyl-6-cyanobenzothiazol-2-yl)ureidomethyl]benzoylamino}propionic acid, 3-{4-[1-(4-cyclohexylphenyl)-3-(5-trifluoromethyl-6-cyanobenzothiazol-2-yl)ureidomethyl]benzoylamino}propionic acid, 3-{4-[1-(4-cyclohexylphenyl)-3-(5-trifluoromethyl-7-methylbenzothiazol-2-yl)ureidomethyl]benzoylamino}propionic acid, 3-{4-[1-(4-cyclohex-1-enylphenyl)-3-(5-trifluoromethyl-7-methylbenzothiazol-2-yl)ureidomethyl]benzoylamino}propionic acid, 3-{4-[1-(4-cyclohex-1-enylphenyl)-3-(5-trifluoromethyl-7-cyanobenzothiazol-2-yl)ureidomethyl]benzoylamino}propionic acid, 3-{4-[1-(4-cyclohexylphenyl)-3-(5-trifluoromethyl-7-cyanobenzothiazol-2-yl)ureidomethyl]benzoylamino}propionic acid, 3-{4-[1-(4-cyclohexylphenyl)-3-(5-trifluoromethyl-6-bromobenzothiazol-2-yl)ureidomethyl]benzoylamino}propionic acid, 3-{4-[1-(4-cyclohex-1-enylphenyl)-3-(5-trifluoromethyl-6-bromobenzothiazol-2-yl)ureidomethyl]benzoylamino}propionic acid, 3-{4-[1-(4-cyclohex-1-enylphenyl)-3-(5-tert-butylbenzothiazol-2-yl)ureidomethyl]benzoylamino}propionic acid, 3-{4-[1-(4-cyclohexylphenyl)-3-(5-tert-butylbenzothiazol-2-yl)ureidomethyl]benzoylamino}propionic acid, 3-{4-[1-(4-cyclohexylphenyl)-3-(5-trifluoromethyl-7-methoxybenzothiazol-2-yl)ureidomethyl]benzoylamino}propionic acid, 3-{4-[1-(4-cyclohexylphenyl)-3-(3-methylsulfonyl-4-methylphenyl)ureidomethyl]benzoylamino}propionic acid, 3-{4-[1-(4-cyclohex-1-enylphenyl)-3-(3-methylsulfonyl-4-methylphenyl)ureidomethyl]benzoylamino}propionic acid, 3-{4-[1-(4-cyclohexylphenyl)-3-(3-ethylthiophenyl)ureidomethyl]benzoylamino}propionic acid, 3-{4-[1-(4-cyclohex-1-enylphenyl)-3-(3-ethylthiophenyl)ureidomethyl]benzoylamino}propionic acid, 3-{4-[1-(4-cyclohexylphenyl)-3-(3-acetylphenyl)ureidomethyl]benzoylamino}propionic acid, 3-{4-[1-(4-cyclohex-1-enylphenyl)-3-(3-acetylphenyl)ureidomethyl]benzoylamino}propionic acid, 3-{4-[1-(4-cyclohexylphenyl)-3-(3-chloro-4-cyanophenyl)ureidomethyl]benzoylamino}propionic acid, 3-{4-[1-(4-cyclohex-1-enylphenyl)-3-(3-chloro-4-cyanophenyl)ureidomethyl]benzoylamino}propionic acid, 3-{4-[1-(4-cyclohexylphenyl)-3-(3-chloro-4-bromophenyl)ureidomethyl]benzoylamino}propionic acid, 3-{4-[1-(4-cyclohex-1-enylphenyl)-3-(3-chloro-4-bromophenyl)ureidomethyl]benzoylamino}propionic acid, 3-{4-[1-(4-cyclohexylphenyl)-3-(2-methyl-1,3-dioxo-2,3-dihydro-1H-isoindol-5-yl)ureidomethyl]benzoylamino}propionic acid, 3-{4-[1-(4-cyclohex-1-enylphenyl-3-(2-methyl-1,3-dioxo-2,3-dihydro-1H-isoindol -5-yl)ureidomethyl]benzoylamino}propionic acid, 3-{4-[1-(4-cyclohexylphenyl)-3-(3-benzooxazol-2-yl-4-trifluoromethoxyphenyl)ureidomethyl]benzoylamino}propionic acid, 3-{4-[1-(4-cyclohex-1-enylphenyl)-3-(3-benzooxazol-2-yl-4-trifluoromethoxyphenyl)ureidomethyl]benzoylamino}propionic acid, 3-{4-[1-(4-cyclohexylphenyl)-3-(3-(2-methyl-2H-tetrazol-5-yl)phenyl)ureidomethyl]benzoylamino}propionic acid, 3-{4-[1-(4-cyclohex-1-enylphenyl)-3-(3-(2-methyl-2H-tetrazol-5-yl)phenyl)ureidomethyl]benzoylamino}propionic acid, and 3-{4-[3-(3-cyano-5-trifluoromethylphenyl)-1-(4-cyclohex-1-enylphenyl)ureidomethyl]benzoylamino}propionic acid or any optical or geometric isomer or tautomeric form thereof including mixtures of these or a pharmaceutically acceptable salt thereof.

4. A pharmaceutical composition according to claim 3 in unit dosage form, said composition comprising from about 0.05 mg to about 1000 mg of said compound.

5. A pharmaceutical composition according to claim 3 in unit dosage form, said composition comprising from about 0.1 mg to about 500 mg of said compound.

6. A pharmaceutical composition according to claim 3 in unit dosage form, said composition comprising from about 0.5 mg to about 200 mg of said compound.

* * * * *

UNITED STATES PATENT AND TRADEMARK OFFICE
CERTIFICATE OF CORRECTION

| | | |
|---|---|---|
| PATENT NO. | : 6,706,744 B2 | Page 1 of 1 |
| APPLICATION NO. | : 09/996023 | |
| DATED | : March 16, 2004 | |
| INVENTOR(S) | : Madsen et al. | |

It is certified that error appears in the above-identified patent and that said Letters Patent is hereby corrected as shown below:

Title Page, item (74) Attorney, Agent or Firm – Change "Richard W. Boak" to --Richard W. Bork--

Signed and Sealed this

Seventh Day of August, 2007

JON W. DUDAS
*Director of the United States Patent and Trademark Office*

UNITED STATES PATENT AND TRADEMARK OFFICE
CERTIFICATE OF CORRECTION

PATENT NO. : 6,706,744 B2
APPLICATION NO. : 09/996023
DATED : March 16, 2004
INVENTOR(S) : Madsen et al.

It is certified that error appears in the above-identified patent and that said Letters Patent is hereby corrected as shown below:

Column 74, lines 40 - 41, Claim 1 – Change "3-trifluoromethoxyphenyl" to --3-trifluoromethylphenyl--

Column 74, lines 44 - 45, Claim 1 – Change "3-trifluoromethoxyphenyl" to --3-trifluoromethylphenyl--

Column 78, line 30 - 31, Claim 1 – Change "3-trifluoromethoxybenzothiazol-2-yl)" to --3-(6-trifluoromethoxybenzothiazol-2-yl)--

Delete Column 82, line 28 through Column 90, line 10 and replace with --3. A pharmaceutical composition comprising at least one compound according to claim 1 together with one or more pharmaceutically acceptable carriers or excipients.--

Signed and Sealed this

Sixteenth Day of October, 2007

JON W. DUDAS
*Director of the United States Patent and Trademark Office*